United States Patent
Yamamoto et al.

(10) Patent No.: US 12,006,358 B2
(45) Date of Patent: Jun. 11, 2024

(54) ANTIBODY AGAINST ADVANCED GLYCATION END PRODUCTS AND USE THEREOF

(71) Applicant: Bloom Technology Corporation, Kumamoto (JP)

(72) Inventors: Tetsuro Yamamoto, Kumamoto (JP); Shota Tsuchida, Kumamoto (JP); Tomoaki Shigeta, Kumamoto (JP); Kazumi Sasamoto, Kumamoto (JP); Mami Chirifu, Kumamoto (JP)

(73) Assignee: BLOOM TECHNOLOGY CORPORATION, Kumamoto (JP)

(*) Notice: Subject to any disclaimer, the term of this patent is extended or adjusted under 35 U.S.C. 154(b) by 704 days.

(21) Appl. No.: 17/271,381

(22) PCT Filed: Aug. 30, 2019

(86) PCT No.: PCT/JP2019/034195
§ 371 (c)(1),
(2) Date: Feb. 25, 2021

(87) PCT Pub. No.: WO2020/045646
PCT Pub. Date: Mar. 5, 2020

(65) Prior Publication Data
US 2021/0221879 A1     Jul. 22, 2021

(30) Foreign Application Priority Data

Aug. 31, 2018   (JP) ................. 2018-163668
Dec. 28, 2018   (JP) ................. 2018-248166

(51) Int. Cl.
C07K 16/18   (2006.01)
C07D 241/12  (2006.01)

(52) U.S. Cl.
CPC ............ *C07K 16/18* (2013.01); *C07D 241/12* (2013.01); *C07K 2317/92* (2013.01)

(58) Field of Classification Search
None
See application file for complete search history.

(56) References Cited

U.S. PATENT DOCUMENTS

2018/0298087 A1   10/2018   Gruber

FOREIGN PATENT DOCUMENTS

| JP | 2001-316389 A | 11/2001 |
|---|---|---|
| JP | 2003-300961 A | 10/2003 |
| JP | 2004-250404 A | 9/2004 |
| JP | 2006-312621 A | 11/2006 |
| JP | 6050654 B2 | 12/2016 |

(Continued)

OTHER PUBLICATIONS

Japanese OA issued on Aug. 29, 2023 for corresponding JP patent application No. 2020-539638 with English Translation.

(Continued)

*Primary Examiner* — Karl J Puttlitz
(74) *Attorney, Agent, or Firm* — BROWDY AND NEIMARK, PLLC

(57) ABSTRACT

The present invention is directed to providing a monoclonal antibody having high selectivity and affinity for AGEs, particularly, AGEs derived from glyceraldehyde or AGEs derived from glycolaldehyde, and an analysis method utilizing the same. Another object of the present invention is to provide methods for diagnosing, treating and preventing a disease using the monoclonal antibody.

2 Claims, 22 Drawing Sheets
Specification includes a Sequence Listing.

(56) References Cited

FOREIGN PATENT DOCUMENTS

| | | |
|---|---|---|
| JP | 2017-043595 A | 3/2017 |
| JP | 2019-041668 A | 3/2019 |

OTHER PUBLICATIONS

Munesue et al., "Low Molecular Weight of Japanese Soy Sauce Act as a RAGE Antagonist via Inhibition of RAGE Trafficking to Lipid Rafts", Journal of Food and Function, 2013, vol. 4, No. 12, pp. 1835-1842.
Takeuchi M., Journal of Kanazawa Medical University, 37 (4): 141-161, 2012.
Takeuchi M., et al., Journal of Kanazawa Medical University, 40 (2/3): 95-103, 2015.
Takeuchi M., Diagnostics 6 (2), 23, 2016; doi: 10.3390.
Takeuchi M., et al., Molecular Medicine, 6 (2): 114-125, 2000.
Jinno M., et al., Human Reproduction, 26 (3), 604-610, 2011.
Sakai A., et al., The journal of Japan Mibyo System Association, 21 (1): 93-96, 2015.
Matsui T., et al., Immunology Letters 167 (2), 141-146, 2015.
Usui T., et al., Biosci. Biotechnol. Biochem. 67 (4), 930-932, 2003.
Hofmann T., et al., J. Agric. Food Chem. 47(2), 379-390, 1999.
Hayashi T., et al., J. Agric. Food Chem. 25(6), 1282-1287, 1977.
Hayashi T., et Agric. Biol. Chem. 49 (11), 3131-3137, 1985.
Tessier F.J., et al., Biochem. J. 369(3), 705-719, 2003.
He W., et al., Biomed. Res. Int. 684242, 2015.
Pardali E., et al., Int. J. Mol. Sci. 2017, 18, 2157; doi:10.3390/ijms18102157.
Wondrak G.T., et al., Free Radic. Biol. Med. 29(6), 557-567, 2000.
International Search Report dated Oct. 8, 2019, issued in corresponding International Appl. No. PCT/JP2019/034195.
Takeuchi et al., "Assessment of the Concentrations of Various Advanced Glycation End-Products in Beverages and Foods That Are Commonly Consumed in Japan", Plos One, vol. 10, No. 3, 2015, p. 1-16.
Takeuchi et al., "Involvement of Toxic AGEs (TAGE) in the Pathogenesis of Diabetic Vascular Complications and Alzheimer's Disease", Journal of Alzheimer's Disease, vol. 16, No. 4, 2009, p. 845-858.
Rudikoff et al., "Single amino acid substitution altering antigen-binding specificity", National Academy of Sciences, vol. 79, 1982. p. 1979-1983.
Partial European Search Report of EP19855041.0 dated Nov. 24, 2022.
Japanese Office Action issued on Feb. 20, 2024, in corresponding JP patent application No. 2020-539638 with English Translation.

Competitive reaction between Glycer-AGEs-BSA and SJ-5 antibody

Fig. 11

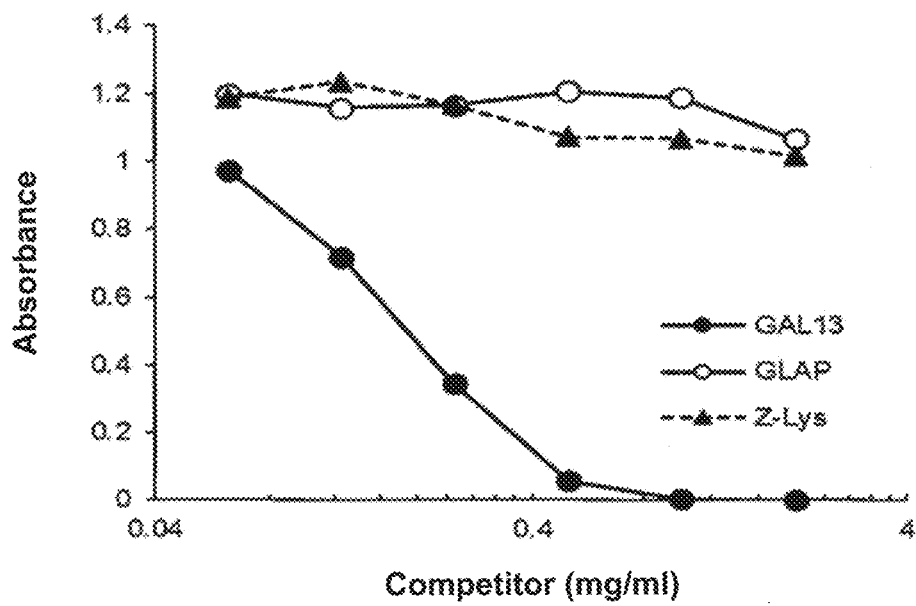

Fig. 12

Amino acid sequence of SJ-5 VH variable region:

EVMLVESGGGLVKPGGSLKLSCAASGFTFSSYGMSWVRQTPEKRLEWVATISGGGSTYYPDSVKGRFTI
SRDNVKNNLYLQMSSLRSEDTALYYCARRGAYGDYGWFAYWGQGTLVTVSA

Amino acid sequence of SJ-5 VL variable region:

DIVLTQSPATLSVTPGDSVSLSCRASQSINNNLHWYQQKSHESPRLLIKCASQSISGIPSRFSGSGSGTD
FTLSINSVETEDFGMYFCQQSNSWPLTFGAGTKLELK

*Underlined: CDR sequence

Fig. 24

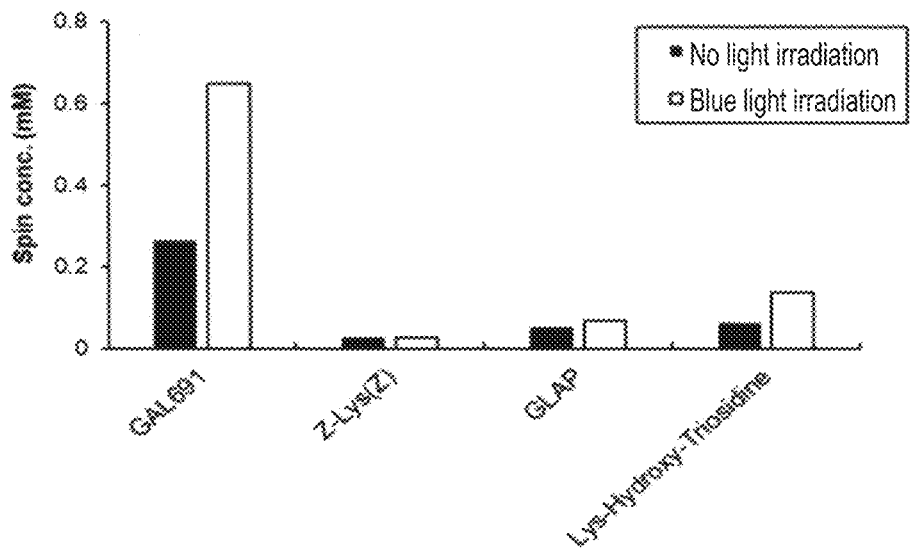

Fig. 25

P B - 1  Amino acid sequence of PB-1 VH variable region:
EVRLQQSGPELVKPGTSVKISCKAS<u>GYSFTGYYMH</u>
WVKQSPVKSLEWIG<u>RIIPYNGATSYNQNFKD</u>KASL
TVDKSSRTAYMDLHSLTSEDSAVYYCAR<u>SRYYGRA</u>
<u>PYYFDY</u>WGQGTTLTVSS P B - 1  Amino acid sequence of PB-1 VL variable region:
DVVVTQTPLSLPVSLGDQASISC<u>RSSQSIVHSNGN</u>
<u>TYLE</u>WYLQKPGQSPKLLIY<u>KVSNRFS</u>GVPDRISGS
GSGTDFTLKISRVEAGDLGVYSC<u>FQGSHVPFT</u>FGS
GTKLEIK

*Underlined: CDR sequence

ANTIBODY AGAINST ADVANCED GLYCATION END PRODUCTS AND USE THEREOF

TECHNICAL FIELD

The present invention relates to a monoclonal antibody or antigen binding fragment thereof that binds to an epitope in advanced glycation end products (AGEs), particularly, AGEs derived from glyceraldehyde or AGEs derived from glycolaldehyde.

BACKGROUND ART

Advanced glycation end products (AGEs) are a generic name for substances that are produced in vivo by the non-enzymatic modification of an amino group of an amino acid, typically, lysine, with reducing sugar, followed by complicated reactions such as oxidation, dehydration and condensation. It is considered that AGEs produced by aging or in a hyperglycemic state are related to lifestyle diseases such as diabetic complications or arteriosclerosis. Particularly, AGEs derived from a sugar metabolism intermediate glyceraldehyde (Glycer-AGEs) are receiving attention as biomarkers useful in diagnosis or prevention (NPLs 1 to 3).

Some structures contained in AGEs have been identified. One of them is carboxymethyllysine ($N^\varepsilon$-(carboxymethyl) lysine, CML) which has been identified as a substance that is produced together with erythronic acid by the oxidative cleavage, in the presence of a transition metal, of the sugar moiety of an Amadori compound produced through the reaction of glucose with lysine. In the history of research on AGEs, the quantification of CML, which has been structurally revealed, have been used as an alternative to the quantification of AGEs. It is considered that the in vitro main production pathway of CML is based on the oxidative cleavage of a Schiff base or an Amadori compound. It is also known that CML is also produced through the intramolecular Cannizzaro reaction of glyoxal (GO) and glycolaldehyde as precursors or the autooxidation of glucose. CML in a protein is stable against acid hydrolysis and can therefore be quantified by high-performance liquid chromatography (HPLC) or gas chromatography/mass spectrometry (GC/MS) (NPL 1). Some reports have been made on structures contained in AGEs (PTLs 1 to 3).

The quantification of AGEs by enzyme immunoassay (EIA) had originated in competitive enzyme-linked immunosorbent assay (ELISA) using anti-AGEs-BSA antibodies directed to AGEs prepared using bovine serum albumin (BSA) (bovine serum albumin containing AGEs, AGEs-BSA) as antigens, and these antibodies have later been found to be anti-CML antibodies directed to a CML structure as an epitope (NPL 1). Meanwhile, it has been reported that non-CML-binding fractions were obtained by adding glyceraldehyde, glycolaldehyde, methylglyoxal, or glyoxal to rabbit serum albumin (RSA), preparing antisera with the respectively prepared AGEs as antigens, and purifying the obtained antisera (NPL 4). ELISA assay using polyclonal antibodies obtained as these fractions has been conducted and utilized as a method for quantifying AGEs instead of CML (NPLs 5 and 6).

For example, research has been made on the correlation of the success or failure of fertility treatment with AGEs derived from glyceraldehyde (Glycer-AGEs). It has been reported that high levels of Glycer-AGEs in blood lead to poor ongoing pregnancy rates (NPLs 1 to 3, 5 and 6). It has also been reported that: AGEs induce endothelial-to-mesenchymal transition; and endothelial-to-mesenchymal transition is involved in the development of cardiovascular disease or fibrous disease (NPLs 13 and 14). In such research, ELISA assay using anti-glyceraldehyde-derived AGEs antibodies among the polyclonal antibodies mentioned above is utilized (NPLs 5 and 6). Some reports have been made on antibodies having binding activity against AGEs (PTLs 4 to 6).

Many reports have been made on the specific chemical structures of various AGEs (e.g., NPLs 8 to 12 and 15). Also, a report has been made on the preparation of monoclonal antibodies directed to AGEs derived from glyceraldehyde as antigens (NPL 7).

CITATION LIST

Patent Literature

PTL 1: Japanese Unexamined Patent Application Publication No. 2001-316389
PTL 2: Japanese Unexamined Patent Application Publication No. 2003-300961
PTL 3: Japanese Unexamined Patent Application Publication No. 2004-250404
PTL 4: Japanese Unexamined Patent Application Publication No. 2006-312621
PTL 5: Japanese Unexamined Patent Application Publication No. 2017-043595
PTL 6: Japanese Unexamined Patent Application Publication No. 2019-041668

Non Patent Literature

NPL 1: Journal of Kanazawa Medical University, 37 (4): 141-161, 2012
NPL 2: Journal of Kanazawa Medical University, 40 (2/3); 95-103, 2015
NPL 3: Diagnostics 6 (2), 23, 2016; doi; 10.3390
NPL 4: Molecular Medicine, 6 (2): 114-125, 2000
NPL 5: Human Reproduction, 26 (3), 604-610, 2011
NPL 6: The journal of Japan Mibyo System Association, 21 (1): 93-96, 2015
NPL 7: Immunology Letters 167 (2), 141-146, 2015
NPL 8: Biosci. Biotechnol. Biochem. 67 (4), 930-932, 2003
NPL 9: J. Agric. Food Chem. 47(2), 379-390, 1999
NPL 10: J. Agric. Food Chem. 25(6), 1282-1287, 1977
NPL 1: Agric. Biol. Chem. 49 (11), 3131-3137
NPL 12: Biochem. J. 369(3), 705-719, 2003
NPL 13: Biomed. Res. Int. 684242, 2015
NPL 14: Int. J. Mol. Sci. 18(10), 2017
NPL 15: Free Radic. Biol. Med. 29(6), 557-567, 2000

SUMMARY OF INVENTION

Technical Problem

An object of the present invention is to provide a monoclonal antibody having high selectivity and affinity for AGEs, particularly, AGEs derived from glyceraldehyde or AGEs derived from glycolaldehyde, and an analysis method utilizing the same. Another object of the present invention is to provide a monoclonal antibody directed to a chemical structure contained in AGEs that damage organisms or cause diseases as an epitope, and an analysis method utilizing the same. A further object of the present invention is to provide methods for diagnosing, treating and preventing a disease, particularly, methods for diagnosing, treating and preventing infertility or an eye disease, using the monoclonal antibody.

Solution to Problem

As a result of research, the present inventors have completed the present invention by finding that a particular monoclonal antibody has favorable selectivity for and high binding activity against an antigen and is utilizable in an analysis method, a diagnosis method, a treatment method and a prevention method.

The following inventions are provided according to the present invention.

[A1] A monoclonal antibody or antigen binding fragment thereof, wherein the antibody or the fragment binds to an epitope in AGEs derived from glyceraldehyde or AGEs derived from glycolaldehyde, which is:
1) a monoclonal antibody or antigen-binding fragment thereof, wherein complementarity determining regions in a heavy-chain variable region (VH CDR1, VH CDR2, and VH CDR3) and a light chain variable region (VL CDR 1, VL CDR2, and VL CDR3) comprise:
  (a) VH CDR1: the amino acid sequence of SEQ ID NO 1, or an amino acid sequence substantially equivalent thereto;
  (b) VH CDR2: the amino acid sequence of SEQ ID NO 2, or an amino acid sequence substantially equivalent thereto;
  (c) VH CDR3: the amino acid sequence of SEQ ID NO 3, or an amino acid sequence substantially equivalent thereto;
  (d) VL CDR1: the amino acid sequence of SEQ ID NO 5, or an amino acid sequence substantially equivalent thereto;
  (e) VL CDR2: the amino acid sequence of SEQ ID NO 6, or an amino acid sequence substantially equivalent thereto;
  (f) VL CDR3: the amino acid sequence of SEQ ID NO 7, or an amino acid sequence substantially equivalent thereto; or
2) an antibody or antigen-binding fragment thereof that cross-competes with said antibody or antigen-binding fragment thereof for binding to the epitope in AGEs derived from glyceraldehyde or AGEs derived from glycolaldehyde.

[A2] The monoclonal antibody or antigen-binding fragment thereof, which binds to a compound represented by formula (I) or (II):

[Chemical Formula 1]

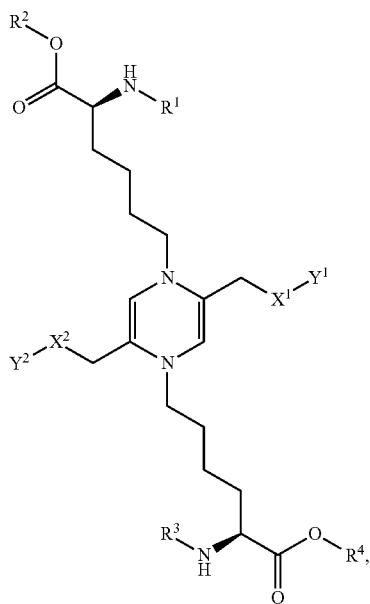

(I)

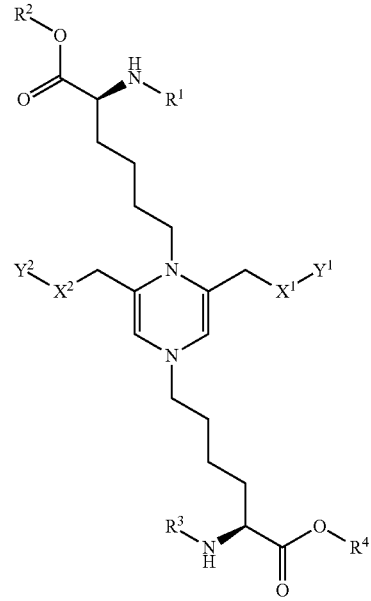

(II)

wherein $R^1$, $R^2$, $R^3$ and $R^4$ are each independently selected form a hydrogen atom, a protecting group, and a peptide group having 1 to 1000 amino acid residues,
$X^1$ and $X^2$ represent —O— or —NH—;
$Y^1$ and $Y^2$ represent a hydrogen atom, a protecting group, or a group:

[Chemical Formula 2]

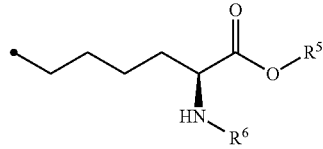

$R^5$ and $R^6$ are each independently selected from a hydrogen atom, a protecting group, and a peptide group having 1 to 1000 amino acid residues;
or a cationic radical thereof, or a dication thereof.

[A3] The monoclonal antibody or the antigen binding fragment thereof according to [A1], which is
1) an antibody or an antigen binding fragment thereof, wherein the amino acid sequences of the heavy-chain variable region and the light-chain variable region are the amino acid sequence of SEQ ID NO 4 or an amino acid sequence substantially equivalent thereto; and the amino acid sequence of SEQ ID NO 8 or an amino acid sequence substantially equivalent thereto; or
2) an antibody or antigen-binding fragment thereof cross-competes with said antibody or its antigen-binding fragment for binding to an epitope in AGEs derived from glyceraldehyde or AGEs derived from glycolaldehyde.

[A4] The monoclonal antibody or the antigen binding fragment thereof according to any one of [A1] to [A3], wherein the epitope is an epitope in AGEs derived from glyceraldehyde.

[A5] The monoclonal antibody or the antigen binding fragment thereof according to any of [A1] to [A4], which is an full-length antibody, Fab, Fab', F(ab')$_2$, Fv, scFv, dsFv, diabody, or sc(Fv)$_2$.

[A6] The monoclonal antibody or the antigen binding fragment thereof according to any of [A1] to [A5], which is a mouse antibody, a humanized antibody, a human antibody, a chimeric antibody, or an antigen binding fragment thereof.

[A7] The monoclonal antibody or the antigen binding fragment thereof according to any of [A1] to [A6], which binds to an epitope of AGEs derived from glyceraldehyde or AGEs derived from glycolaldehyde with a dissociation constant (Kd value) of $1\times10^{-5}$ M or less.

[A8] A pharmaceutical composition comprising the monoclonal antibody or the antigen binding fragment thereof as defined in any of [A1] to [A7].

[A9] The pharmaceutical composition according to [A8], for use in diagnosis, treatment or prevention of a disease selected from obesity, diabetes mellitus, diabetic retinopathy, diabetic cataract, diabetic neuropathy, diabetic cardiomyopathy, diabetic vascular complications, diabetic nephropathy, diabetic renal disease, diabetic foot, diabetic ketoacidosis, periodontal disease, age-related macular degeneration, pulmonary fibrosis, idiopathic pulmonary fibrosis, peribronchiolar fibrosis, interstitial lung disease, lung cancer, cancer fibrous lung disease, chronic obstructive pulmonary disease, acute lower limb artery embolism, peripheral arterial disease, peripheral airway disease, pulmonary emphysema, pyelonephritis, glomerulosclerosis, glomerulonephritis, mesangial proliferative glomerulonephritis, diabetic nephropathy, nephrogenic systemic fibrosis, chronic renal disease, idiopathic retroperitoneal fibrosis, renal disease, scleroderma, renal interstitial fibrosis, female infertility, polycystic ovarian syndrome, ovarian dysfunction, early ovarian dysfunction, ovarian cancer, breast cancer, uterine body cancer, prostate cancer, male infertility, liver disease, cirrhosis, non-alcoholic steatohepatitis, liver cancer, atherothrombotic cerebral infarct, atherosclerosis, internal carotid artery stenosis, aortic valve stenosis, aortic insufficiency, cardiovascular disease, angina pectoris, congestive heart failure, acute heart failure, chronic heart failure, ischemic heart disease, dilated cardiomyopathy, cardiac sarcoidosis, hypertension, pulmonary arterial hypertension, cor pulmonale, myocarditis, vascular-stenosing cardiofibrosis, cardiofibrosis after myocardial infarction, left ventricular hypertrophy after myocardial infarction, rheumatoid arthritis, lifestyle diseases, dyslipidemia, Alzheimer's disease, vascular dementia, cerebral infarction, brain tumor, cerebrovascular disorder, uveitis, endocrine disease, osteoporosis, tongue cancer, oral cancer, pharyngeal cancer, esophageal cancer, stomach cancer, colorectal cancer, rectal cancer, and pancreatic cancer.

[A10] The pharmaceutical composition according to [A8] for use in diagnosis, treatment or prevention of a disease selected from diabetes mellitus, glucose intolerance, retinopathy, nephropathy, complications associated with diabetes mellitus, peripheral neuropathy, leg gangrene, arteriosclerosis, thrombosis, non-alcoholic fatty liver disease, non-alcoholic steatohepatitis, cancer, infertility, polycystic ovarian syndrome, ovarian dysfunction, central nervous disorder, and neurodegenerative disease including Alzheimer's disease.

[A11] The pharmaceutical composition according to [A8], wherein the disease is cancer selected from melanoma, lung cancer, and liver cancer.

[A12] A nucleic acid encoding a monoclonal antibody or antigen-binding fragment thereof as defined in any of [A1] to [A7].

[A13] An expression vector comprising the nucleic acid as defined in [A12].

[A14] A host cell containing the expression vector as defined in [A13].

[A15] A compound represented by formula (I) or (II):

[Chemical Formula 3]

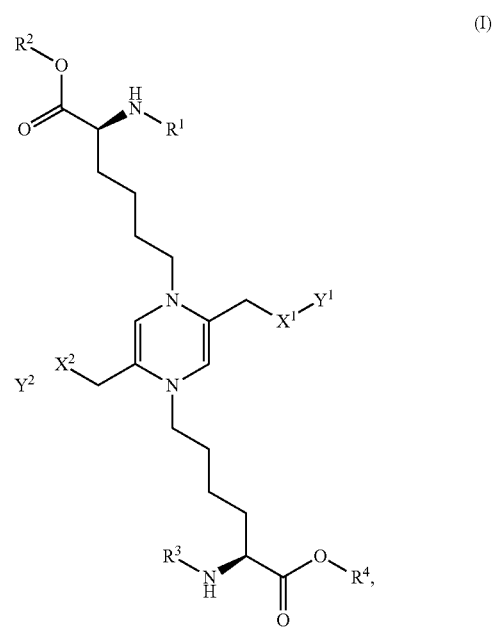

(I)

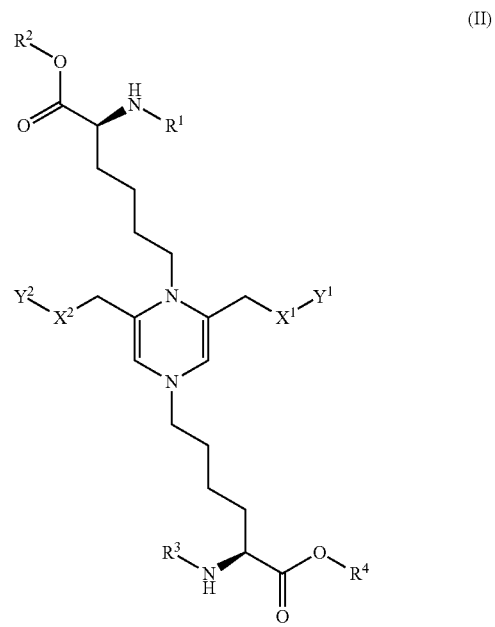

(II)

wherein $R^1$, $R^2$, $R^3$ and $R^4$ are each independently selected from a hydrogen atom, a protecting group, and a peptide group having 1 to 1000 amino acid residues, $X^1$ and $X^2$ represent —O— or —NH—;

$Y^1$ and $Y^2$ are a hydrogen atom, a protecting group, or a group:

[Chemical Formula 4]

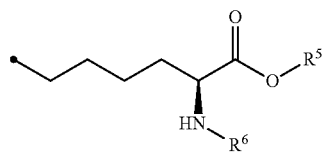

$R^5$ and $R^6$ are each independently selected from a hydrogen atom, a protecting group, and a peptide group having 1 to 1000 amino acid residues;

or a cationic radical thereof, or a dication thereof or a salt thereof.

[A16] A method for preparing an antibody, which comprises:

1) reacting lysine in which an amino group at α-position is protected and glyceraldehyde to obtain a reaction mixture;

2) fractionating the reaction mixture to obtain a fraction containing a compound represented by formula (Ia), (Ib), (IIa), or (IIb):

[Chemical Formula 5]

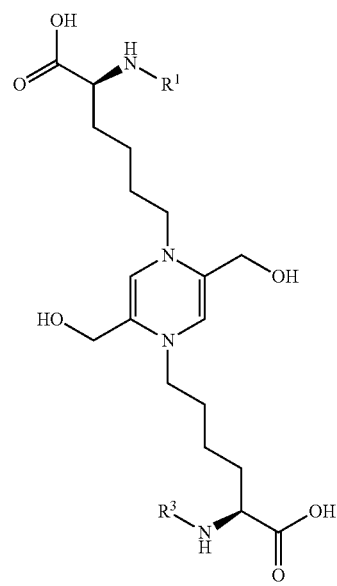

(Ia)

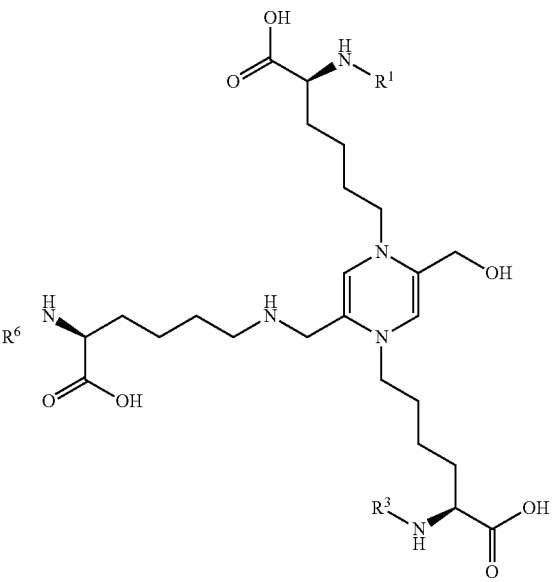

(Ib)

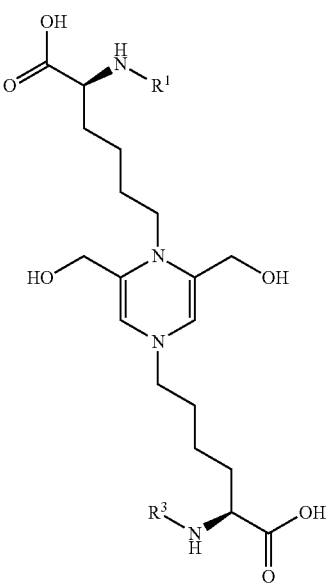

(IIa)

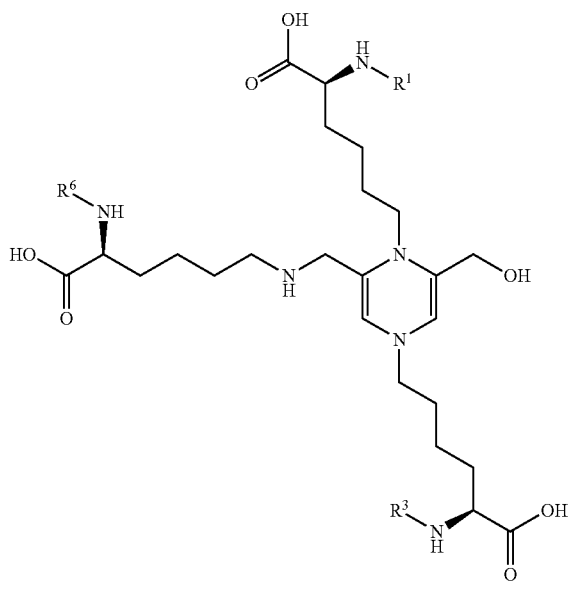

(IIb)

wherein R, R³, and R are protecting groups 3) immunizing an animal using the fraction as an antigen to obtain an antibody.

[B1] A monoclonal antibody or antigen binding fragment thereof, wherein the antibody or the fragment binds to a compound represented by formula (XI) or (XII):

[Chemical Formula 6]

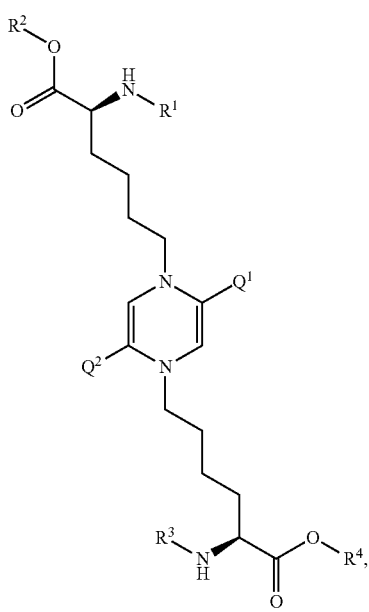

(XI)

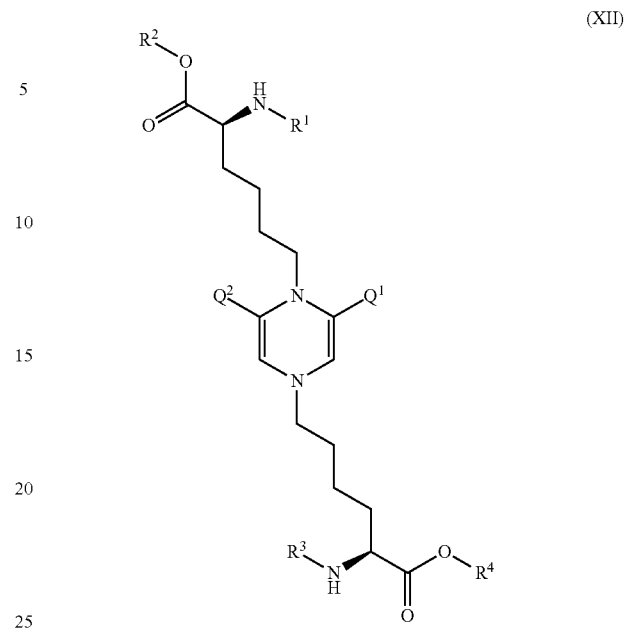

(XII)

wherein $R^1$, $R^2$, $R^3$ and $R^4$ are each independently selected from a hydrogen atom, a protecting group, and a peptide group having 1 to 1000 amino acid residues, $Q^1$ represents a hydrogen atom or a group —$CH_2$—$X^1$—$Y^1$;

$Q^2$ represents a hydrogen atom or a group —$CH_2$—$X^2$—$Y^2$;

$X^1$ and $X^2$ represent —O— or —NH—;

$Y^1$ and $Y^2$ represent a hydrogen atom, a protecting group, or a group:

[Chemical Formula 7]

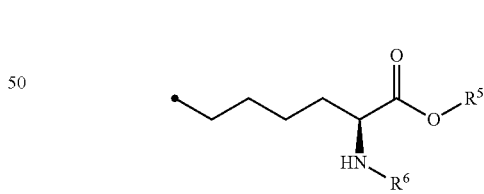

$R^5$ and $R^6$ are each independently selected from a hydrogen atom, a protecting group, and a peptide group having 1 to 1000 amino acid residues;

or a cationic radical thereof, or a dication thereof.

[B2] The antibody or the antigen-binding fragment thereof according to [B1], which binds to a compound represented by formula (I) or (II):

[Chemical Formula 8]

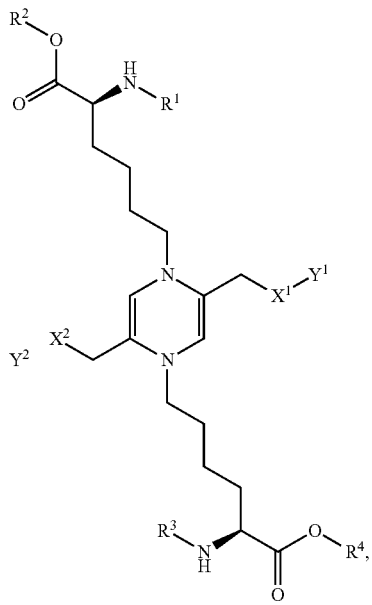

(I)

wherein $R^1$, $R^2$, $R^3$ and $R^4$ are each independently selected form a hydrogen atom, a protecting group, and a peptide group having 1 to 1000 amino acid residues, $X^1$ and $X^2$ represent —O— or —NH—;

$Y^1$ and $Y^2$ represent a hydrogen atom, a protecting group, or a group:

[Chemical Formula 9]

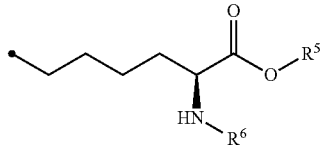

$R^5$ and $R^6$ are each independently selected from a hydrogen atom, a protecting group, and a peptide group having 1 to 1000 amino acid residues;

or a cationic radical thereof, or a dication thereof.

[B3] A monoclonal antibody or antigen binding fragment thereof, wherein the antibody or the fragment binds to an epitope contained in AGEs derived from glyceraldehyde or AGEs derived from glycolaldehyde, which is:

(1) a monoclonal antibody or antigen binding fragment thereof, wherein complementarity determining regions in a heavy-chain variable region (VH CDR1, VH CDR2, and VH CDR3) or a light-chain variable region (VL CDR1, VL CDR2, and VL CDR3) comprise:

(1-1H)
(a) VH CDR1: the amino acid sequence of SEQ ID NO 1, or an amino acid sequence substantially equivalent thereto;
(b) VH CDR2: the amino acid sequence of SEQ ID NO 2, or an amino acid sequence substantially equivalent thereto; and
(c) VH CDR3: the amino acid sequence of SEQ ID NO 3, or an amino acid sequence substantially equivalent thereto;

(1-1L)
(d) VL CDR1: the amino acid sequence of SEQ ID NO 5, or an amino acid sequence substantially equivalent thereto;
(e) VL CDR2: the amino acid sequence of SEQ ID NO 6, or an amino acid sequence substantially equivalent thereto; and
(f) VL CDR3: the amino acid sequence of SEQ ID NO 7, or an amino acid sequence substantially equivalent thereto;

(1-2H)
(g) VH CDR 1: the amino acid sequence of SEQ ID NO 15, or an amino acid sequence substantially equivalent thereto;
(h) VH CDR2: the amino acid sequence of SEQ ID NO 16, or an amino acid sequence substantially equivalent thereto; and
(i) VH CDR3: the amino acid sequence of SEQ ID NO 17, or an amino acid sequence substantially equivalent thereto; or (1-2L)
(j) VL CDR1: the amino acid sequence of SEQ ID NO 19, or an amino acid sequence substantially equivalent thereto;
(k) VL CDR2: the amino acid sequence of SEQ ID NO 20, or an amino acid sequence substantially equivalent thereto; and
(l) VL CDR3: the amino acid sequence of SEQ ID NO 21, or an amino acid sequence substantially equivalent thereto; or (2) a monoclonal antibody or antigen binding fragment thereof that cross-competes with said monoclonal antibody or antigen binding fragment thereof of (1) for binding to the epitope in AGEs derived from glyceraldehyde or AGEs derived from glycolaldehyde.

[B4] The monoclonal antibody or the antigen binding fragment thereof according to any of [B1] to [B3], wherein the antibody or the fragment is capable of binding to an epitope contained in AGEs derived from glyceraldehyde or AGEs derived from glycolaldehyde, which is:
(1) a monoclonal antibody or antigen binding fragment thereof, wherein complementarity determining regions in a heavy-chain variable region (VH CDR1, VH CDR2, and VH CDR3) and a light-chain variable region (VL CDR1, VL CDR2, and VL CDR3) comprise:
(1-1)
(a) VH CDR 1: the amino acid sequence of SEQ ID NO 1, or an amino acid sequence substantially equivalent thereto;
(b) VH CDR2: the amino acid sequence of SEQ ID NO 2, or an amino acid sequence substantially equivalent thereto;
(c) VH CDR3: the amino acid sequence of SEQ ID NO 3, or an amino acid sequence substantially equivalent thereto;
(d) VL CDR1: the amino acid sequence of SEQ ID NO 5, or an amino acid sequence substantially equivalent thereto;
(e) VL CDR2: the amino acid sequence of SEQ ID NO 6, or an amino acid sequence substantially equivalent thereto; and
(f) VL CDR3: the amino acid sequence of SEQ ID NO 7, or an amino acid sequence substantially equivalent thereto; or
(1-2)
(g) VH CDR 1: the amino acid sequence of SEQ ID NO 15, or an amino acid sequence substantially equivalent thereto;
(h) VH CDR2: the amino acid sequence of SEQ ID NO 16, or an amino acid sequence substantially equivalent thereto;
(i) VH CDR3: the amino acid sequence of SEQ ID NO 17, or an amino acid sequence substantially equivalent thereto;
(j) VL CDR1: the amino acid sequence of SEQ ID NO 19, or an amino acid sequence substantially equivalent thereto;
(k) VL CDR2; the amino acid sequence of SEQ ID NO 20, or an amino acid sequence substantially equivalent thereto; and
(l) VL CDR3: the amino acid sequence of SEQ ID NO 21, or an amino acid sequence substantially equivalent thereto; or
(2) a monoclonal antibody or antigen binding fragment thereof that cross-competes with said monoclonal antibody or antigen binding fragment thereof of (1) for binding to the epitope in AGEs derived from glyceraldehyde or AGEs derived from glycolaldehyde.

[B5] The monoclonal antibody or the antigen binding fragment thereof according to any one of [B1] to [B4], wherein the antibody or the fragment is capable of binding to an epitope contained in AGEs derived from glyceraldehyde or AGEs derived from glycolaldehyde, which is:
(1) an antibody or an antigen binding fragment thereof, wherein the amino acid sequences of the heavy-chain variable region and the light-chain variable region are the amino acid sequence of SEQ ID NO 4 or an amino acid sequence substantially equivalent thereto, and/or the amino acid sequence of SEQ ID NO 8 or an amino acid sequence substantially equivalent thereto; or
the amino acid sequence of SEQ ID NO 18 or an amino acid sequence substantially equivalent thereto, and/or the amino acid sequence of SEQ ID NO 22 or an amino acid sequence substantially equivalent thereto; or
(2) an antibody or antigen binding fragment thereof cross-competes with said antibody or antigen binding fragment thereof of (1) for binding to the epitope in AGEs derived from glyceraldehyde or AGEs derived from glycolaldehyde.

[B6] The monoclonal antibody or the antigen binding fragment thereof according to any one of [B1] to [B5], which binds to an epitope contained in AGEs derived from glyceraldehyde.

[B7] The monoclonal antibody or the antigen binding fragment thereof according to any of [B1] to [B6], which is a full-length antibody, Fab, Fab', F(ab')$_2$, Fv, scFv, dsFv, diabody, or sc(Fv)$_2$.

[B8] The monoclonal antibody or the antigen binding fragment thereof according to any of [B1] to [B7], which is a mouse antibody, a humanized antibody, a human antibody, a chimeric antibody, or an antigen binding fragment thereof.

[B9] The monoclonal antibody or the antigen binding fragment thereof according to any of [B1] to [B8], which binds to an epitope of AGEs derived from glyceraldehyde or AGEs derived from glycolaldehyde with a dissociation constant ($K_d$ value) of $1 \times 10^{-5}$ M or less.

[B10] A pharmaceutical composition comprising the monoclonal antibody or the antigen binding fragment thereof as defined in any of [B1] to [B9].

[B11] The pharmaceutical composition according to [B10], for use in diagnosis, treatment or prevention of a disease selected from obesity, diabetes mellitus, diabetic retinopathy, diabetic cataract, diabetic neuropathy, diabetic cardiomyopathy, diabetic vascular complications, diabetic nephropathy, diabetic renal disease, diabetic foot, diabetic ketoacidosis, periodontal disease, age-related macular degeneration, pulmonary fibrosis, idiopathic pulmonary fibrosis, peribronchiolar fibrosis, interstitial lung disease, lung cancer, cancer fibrous lung disease, chronic obstructive pulmonary disease, acute lower limb artery embolism, peripheral arterial disease, peripheral airway disease, pulmonary emphysema, pyelonephritis, glomerulosclerosis, glomerulonephritis, mesangial proliferative glomerulonephritis, diabetic nephropathy, nephrogenic systemic fibrosis, chronic renal disease, idiopathic retroperitoneal fibrosis, renal disease, scleroderma, renal interstitial fibrosis, female infertility, polycystic ovarian syndrome, ovarian dysfunction, early ovarian dysfunction, ovarian cancer, breast cancer, uterine body cancer, prostate cancer, male infertility, liver disease, cirrhosis, non-alcoholic steatohepatitis, liver cancer, atherothrombotic cerebral infarct, atherosclerosis, internal carotid artery stenosis, aortic valve stenosis, aortic insufficiency, cardiovascular disease, angina pectoris, congestive heart failure, acute heart failure, chronic heart failure, ischemic heart disease, dilated cardiomyopathy, cardiac sarcoidosis, hypertension, pulmonary arterial hypertension, cor pulmonale, myocarditis, vascular-stenosing cardiofibrosis, cardiofibrosis after myocardial infarction, left ventricular hypertrophy after myocardial infarction, rheumatoid arthritis, lifestyle diseases, dyslipidemia, Alzheimer's disease, vascular dementia, cerebral infarction, brain tumor, cerebrovascular disorder, uveitis, endocrine disease, osteoporosis, tongue cancer, oral cancer, pharyngeal cancer, esophageal cancer, stomach cancer, colorectal cancer, rectal cancer, pancreatic cancer, retinitis pigmentosa, amaurosis congenita of Leber, Stargardt disease, Usher syndrome, choroideremia, cone-rod dystrophy, cone dystrophy, progressive retinal atrophy, macular dystrophy, choroidal sclerosis, total choroidal vascular atrophy, cystoid macular edema, uveitis, retinal detachment, macular hole, macular telangiectasia, glaucoma, optic neuropathy, ischemic retinal disease, retinopathy of prematurity, retinal vascular occlusion, and retinal microaneurysms.

[B12] The pharmaceutical composition according to [B10], for use in diagnosis, treatment or prevention of a disease selected from diabetes mellitus, glucose intolerance, retinopathy, nephropathy, complications associated with diabetes mellitus, peripheral neuropathy, leg gangrene, arteriosclerosis, thrombosis, non-alcoholic fatty liver disease, non-alcoholic steatohepatitis, cancer, infertility, polycystic ovarian syndrome, ovarian dysfunction, central nervous disorder, and neurodegenerative disease including Alzheimer's disease.

[B13] The pharmaceutical composition according to [B12], wherein the disease is cancer selected from melanoma, lung cancer, and liver cancer.

[B14] The pharmaceutical composition according to [B10], for use in diagnosis, treatment or prevention of an eye disease.

[B15] The pharmaceutical composition according to [B14], wherein the eye disease is selected from diabetic retinopathy, diabetic cataract, retinitis pigmentosa, diabetic macular edema, amaurosis congenita of Leber, Stargardt disease, Usher syndrome, choroideremia, cone-rod dystrophy, cone dystrophy, progressive retinal atrophy, age-related macular degeneration, macular dystrophy, choroidal sclerosis, total choroidal vascular atrophy, cystoid macular edema, uveitis, retinal detachment, macular hole, macular telangiectasia, glaucoma, optic neuropathy, ischemic retinal disease, retinopathy of prematurity, retinal vascular occlusion, and retinal microaneurysms.

[B16] A nucleic acid encoding a monoclonal antibody or antigen binding fragment thereof as defined in any one of [B1] to [B9].

[B17] An expression vector comprising the nucleic acid as defined in [B16].

[B18] A host cell containing the expression vector as defined in [B17].

[B19] A compound represented by formula (I) or (II):

[Chemical Formula 10]

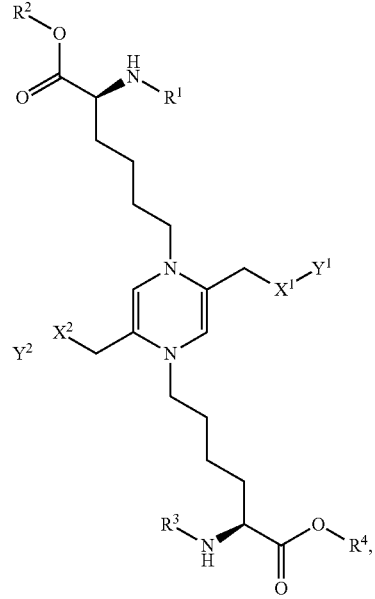

(I)

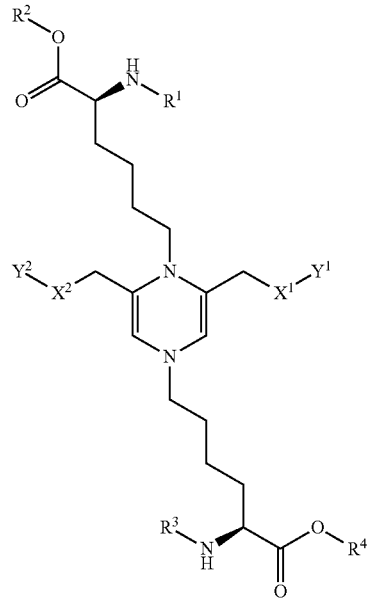

(II)

wherein $R^1$, $R^2$, $R^3$ and $R^4$ are each independently selected from a hydrogen atom, a protecting group, and a peptide group having 1 to 1000 amino acid residues,
$X^1$ and $X^2$ represent —O— or —NH—;
$Y^1$ and $Y^2$ represent a hydrogen atom, a protecting group, or a group:

[Chemical Formula 11]

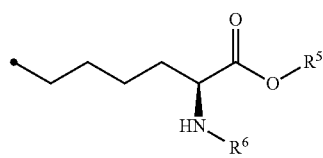

$R^5$ and $R^6$ are each independently selected from a hydrogen atom, a protecting group, and a peptide group having 1 to 1000 amino acid residues;

or a cationic radical thereof, a dication thereof, or a salt thereof.

[B20] A method for preparing an antibody, which comprises:

1) reacting lysine in which an amino group at α-position is protected and glyceraldehyde to obtain a reaction mixture;
2) fractionating the reaction mixture to obtain a fraction containing a compound represented by formula (Ia), (Ib), (IIa), or (IIb):

[Chemical Formula 12]

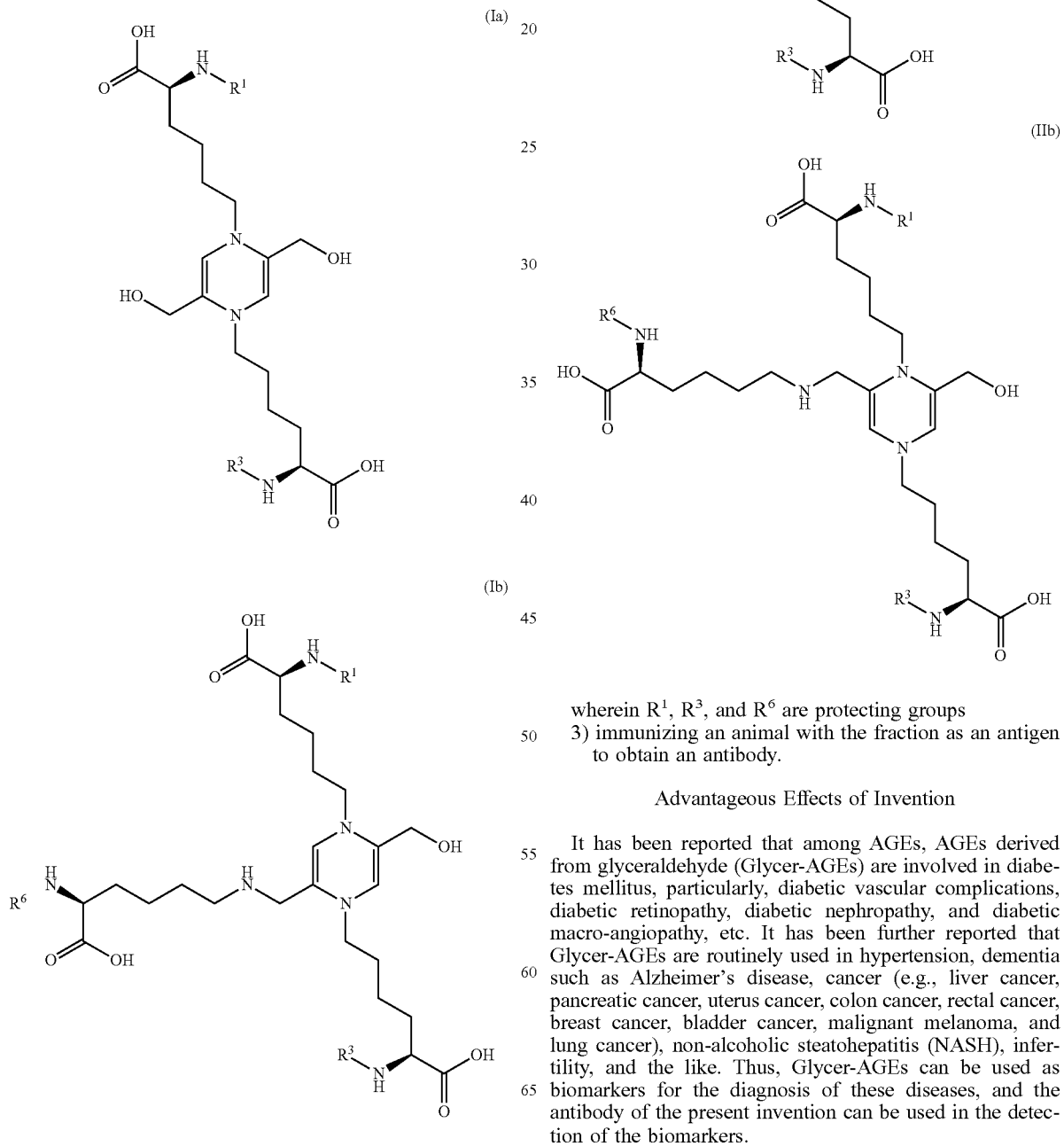

wherein $R^1$, $R^3$, and $R^6$ are protecting groups 3) immunizing an animal with the fraction as an antigen to obtain an antibody.

Advantageous Effects of Invention

It has been reported that among AGEs, AGEs derived from glyceraldehyde (Glycer-AGEs) are involved in diabetes mellitus, particularly, diabetic vascular complications, diabetic retinopathy, diabetic nephropathy, and diabetic macro-angiopathy, etc. It has been further reported that Glycer-AGEs are routinely used in hypertension, dementia such as Alzheimer's disease, cancer (e.g., liver cancer, pancreatic cancer, uterus cancer, colon cancer, rectal cancer, breast cancer, bladder cancer, malignant melanoma, and lung cancer), non-alcoholic steatohepatitis (NASH), infertility, and the like. Thus, Glycer-AGEs can be used as biomarkers for the diagnosis of these diseases, and the antibody of the present invention can be used in the detection of the biomarkers.

Furthermore, the antibody according to the present invention can be used for neutralizing the effects of Glycer-AGEs in organisms and can also be used in the treatment or the like of diseases.

BRIEF DESCRIPTION OF DRAWINGS

FIG. 11 is a graph showing results of a reactivity evaluation test of the SJ-5 antibody with GLAP by competitive ELISA.

FIG. 12 is a diagram showing the amino acid sequences of a heavy-chain variable region and a light-chain variable region of the novel monoclonal antibody SJ-5. CDRs are underlined.

FIG. 24 is a graph showing results of a test for confirming the formation of a superoxide anion through the photosensitizing effect of GAL691 in Example 23.

FIG. 25 is a diagram showing the amino acid sequences of variable regions of a monoclonal antibody PB-1. CDR sequences are underlined.

DESCRIPTION OF EMBODIMENTS

Figure 1:
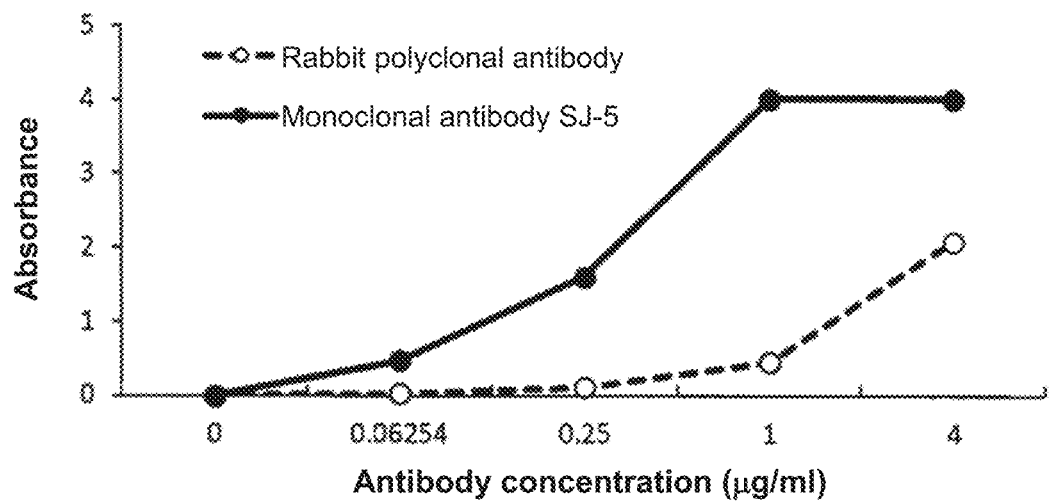
FIG. 1 is a graph showing results of a reactivity comparison test of a novel monoclonal antibody (SJ-5) and an anti-glyceraldehyde-derived AGEs polyclonal antibody by direct ELISA.

In one aspect of the present invention, the antibody of the present invention is an isolated antibody. The isolated antibody excludes a naturally occurring antibody that has not undergone any external operation (artificial operation), i.e., an antibody that has been produced in the body of a certain individual and is in a state remaining therein. The antibody of the present invention is typically a monoclonal antibody or antigen binding fragment thereof.

One embodiment of the present invention provides an antibody which binds to a compound represented by formula (XI) or (XII).

[Chemical Formula 13]

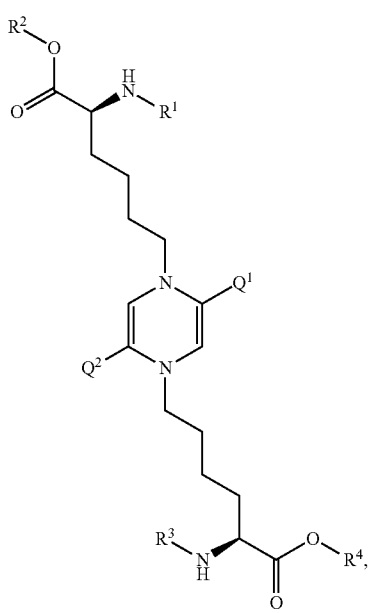
(XI)

[Chemical Formula 14]

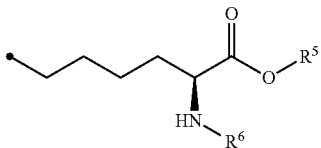

$R^5$ and $R^6$ are each independently selected from a hydrogen atom, a protecting group, and a peptide group having 1 to 1000 amino acid residues;

or a cationic radical thereof, a dication thereof, or a salt thereof.

Another embodiment of the present invention provides an antibody which binds to a compound represented by formula (I) or (II):

[Chemical Formula 15]

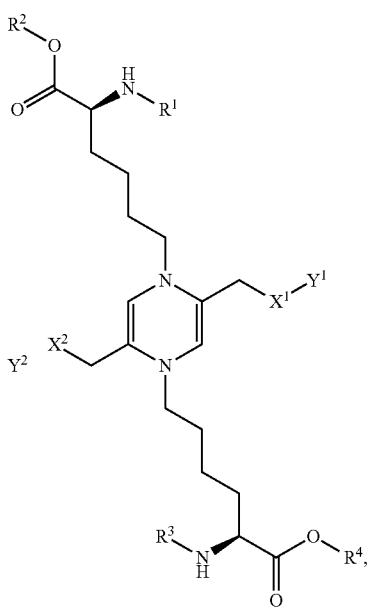
(I)

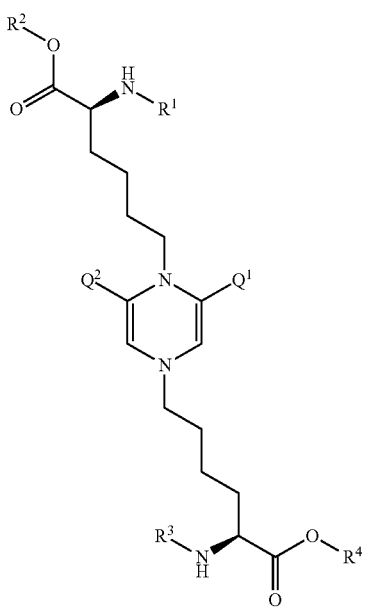
(XII)

wherein $R^1$, $R^2$, $R^3$ and $R^4$ are each independently selected from a hydrogen atom, a protecting group, and a peptide group having 1 to 1000 amino acid residues, $Q^1$ represents a hydrogen atom or a group —$CH_2$—$X^1$—$Y^1$;

$Q^2$ represents a hydrogen atom or a group —$CH_2$—$X^2$—$Y^2$;

$X^1$ and $X^2$ represent —O— or —NH—;

$Y^1$ and $Y^2$ represent a hydrogen atom, a protecting group, or a group:

-continued (II)

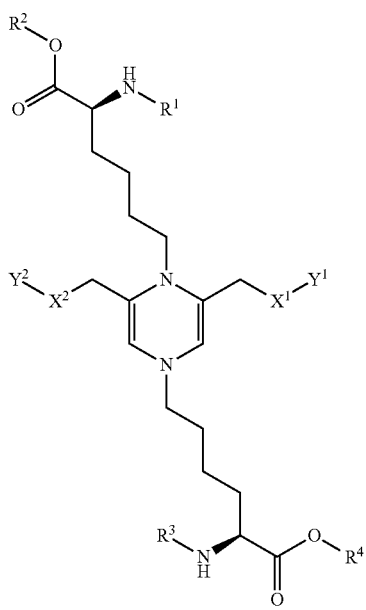

wherein $R^1$, $R^2$, $R^3$ and $R^4$ are each independently selected from a hydrogen atom, a protecting group, and a peptide group having 1 to 1000 amino acid residues,
$X^1$ and $X^2$ represent —O— or —NH—;
$Y^1$ and $Y^2$ are a hydrogen atom, a protecting group, or a group:

[Chemical Formula 16]

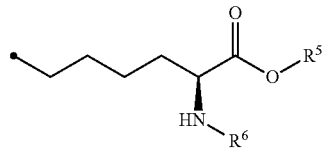

$R^5$ and $R^6$ are each independently selected from a hydrogen atom, a protecting group, and a peptide group having 1 to 1000 amino acid residues;
or a cationic radical thereof, a dication thereof, or a salt thereof.

When $R^1$, $R^2$, $R^3$, $R^4$, $R^5$ and $R^6$ are a protecting group, $R^1$, $R^3$ and $R^6$ are a protecting group for the amino group, and $R^2$, $R^4$ and $R^5$ are a protecting group for the hydroxy group.

When $X^1$ or $X^2$ is —O—, $Y^1$ or $Y^2$ may be a protecting group for the hydroxy group. When $X^1$ or $X^2$ is —NH—, $Y^1$ or $Y^2$ may be a protecting group for the amino group.

Examples of the protecting group for hydroxy include $C_{1-6}$ alkyl, $C_{1-6}$ alkoxy $C_{1-6}$alkyl, aryl $C_{1-6}$alkyl, heteroaryl $C_{1-6}$alkyl, ((amino $C_{1-6}$alkyl)carbonyloxy)$C_{1-6}$alkyl, unsaturated heterocyclylcarbonyloxy $C_{1-6}$ alkyl, aryl di($C_{1-6}$alkyl)silyl, and tri($C_{1-6}$ alkyl)silyl. Preferred examples of the protecting group for hydroxy include $C_{1-6}$ alkyl.

Examples of the protecting group for amino include $C_{1-6}$ alkylcarbonyl, aryl $C_{1-6}$alkylcarbonyl, arylcarbonyl, heteroarylcarbonyl, $C_{1-6}$ alkoxycarbonyl, $C_{1-6}$alkylaminocarbonyl, di($C_{1-6}$alkyl)aminocarbonyl, aryl $C_{1-6}$alkyl, heteroaryl $C_{1-6}$alkyl, and (aryl $C_{1-6}$ alkyl)aminocarbonyl. Preferred examples of the protecting group for amino include benzyloxycarbonyl, t-butoxycarbonyl, and 9-fluorenylmethoxycarbonyl. Also, amino may be protected to thereby form a saturated or unsaturated heterocyclic group such as phthalimide, succinimide, glutarimide, or 1-pyrrolyl.

The peptide group herein is not particularly limited and means, for example, a peptide group having 1 to 10000, 1 to 5000, 1 to 3000, 1 to 2000, 1 to 1000, 1 to 500, or 1 to 100 amino acid residues. The amino acid residues are selected from natural amino acids.

The compound represented by formula (I) or (II) can be prepared using lysine having a protected amino group of a side chain. The structural formula range represented by formula (I) or (II) includes compounds represented by the following formulas:

[Chemical Formula 17]

(Ia)

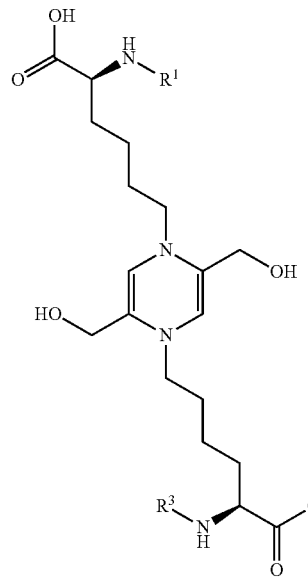

(Ib)

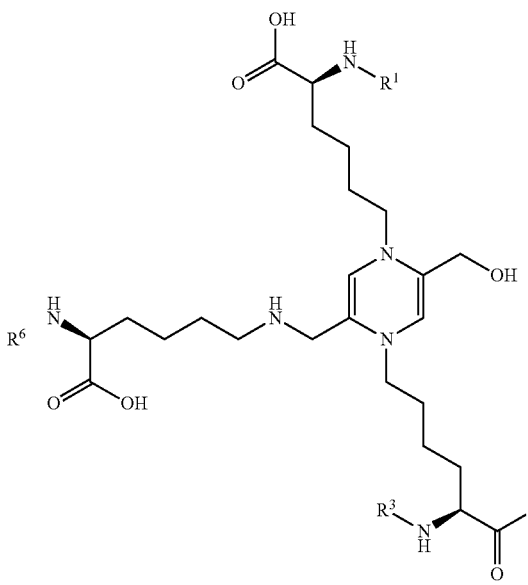

-continued
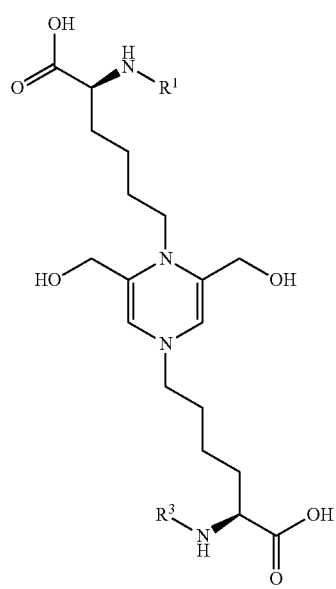
(IIa)
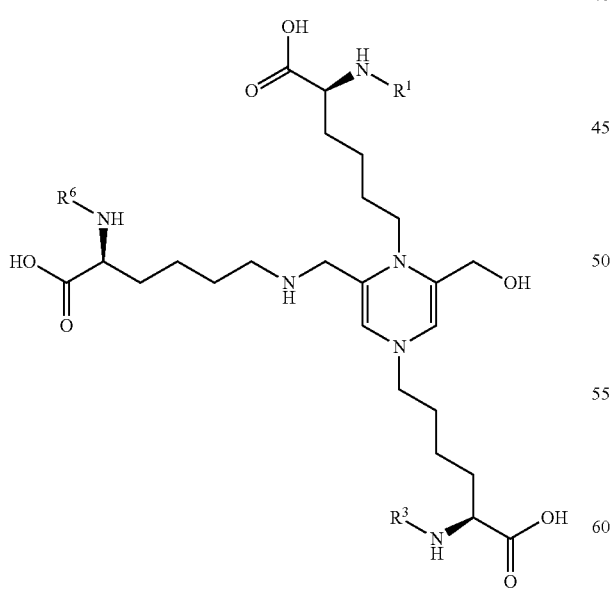
(IIb)
In the formulas, $R^1$, $R^3$, and $R^5$ are a protecting group for the amino group. For example, in the formulas described above, $R^1$, $R^3$, and $R^6$ are benzyloxycarbonyl.
The cationic radicals of the compounds represented by formula (T) and formula (I1) are represented by the following formula (III) and formula (IV):
[Chemical Formula 19]
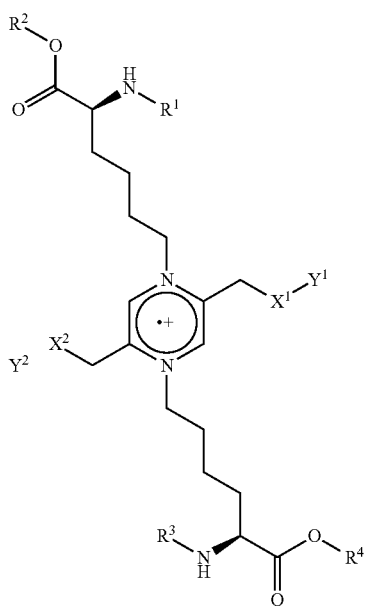
(III)
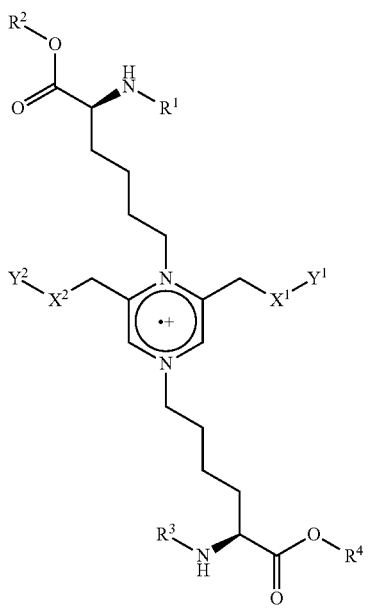
(IV)

In the formulas, Rt, $R^2$, $R^3$, $R^4$, XI, $X^2$, $Y^1$, and $Y^2$ are as defined in formula (I) and formula (II). Formula (III) and formula (IV) include cationic radicals represented by the following formulas:
[Chemical Formula 20]
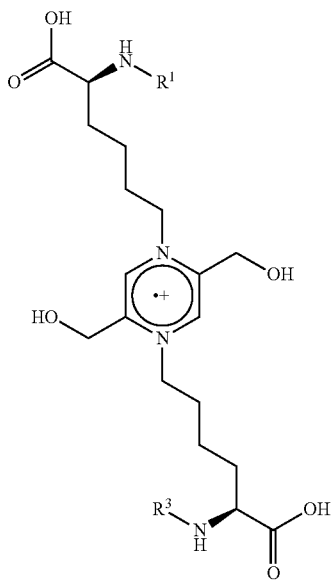
(IIIa)
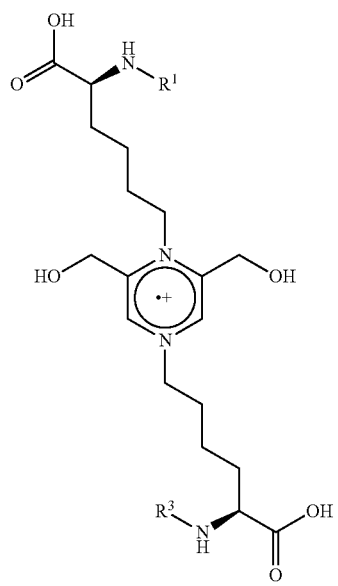
(IVa)
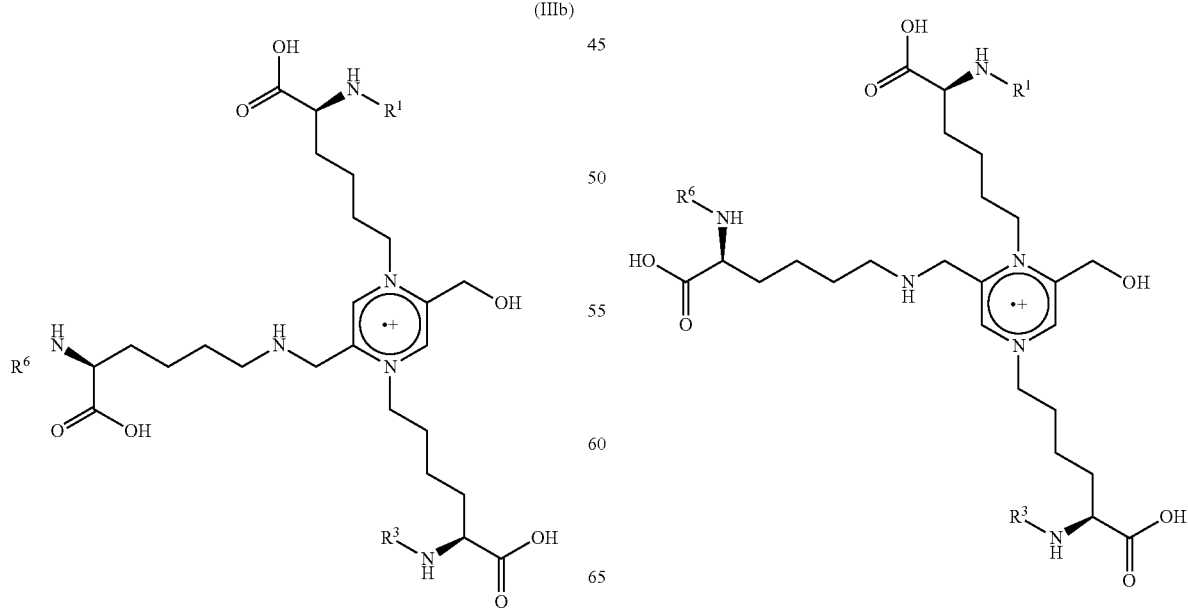

The dications of the compounds represented by formula (I) and formula (II) are represented by the following formula (V) and formula (VI):
[Chemical Formula 21]
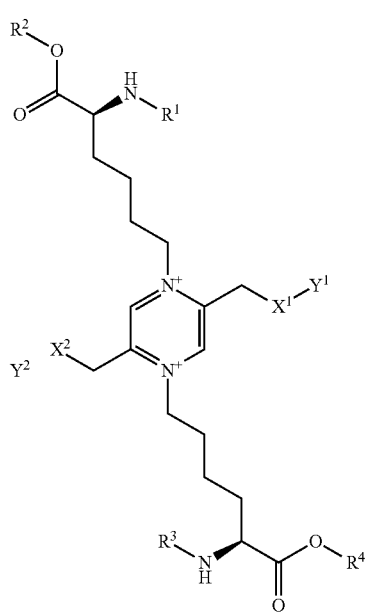
(V)
In the formulas, $R^1$, $R^2$, $R^3$, $R^4$, $X^1$, $X^2$, $Y^1$, and $Y^2$ are as defined in formula (I) and formula (II). Formula (V) and formula (VI) include dications represented by the following formulas:
[Chemical Formula 22]
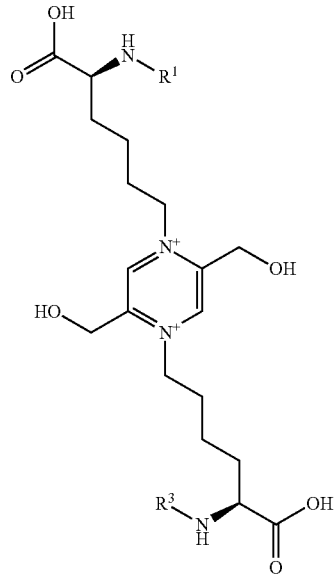
(Va)
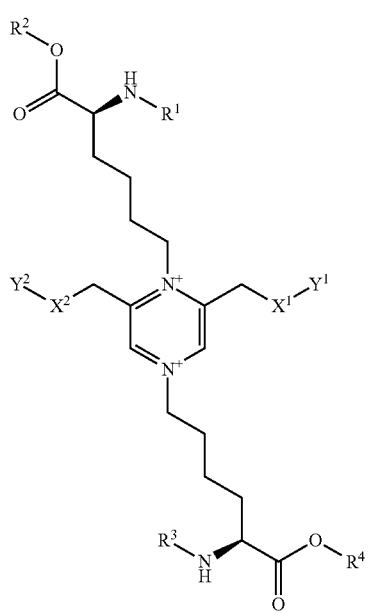
(VI)
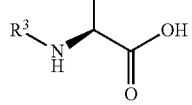
(Vb)

-continued

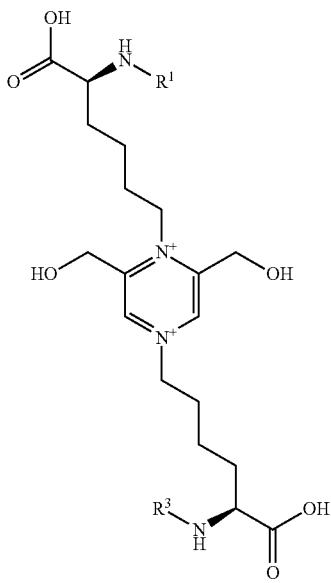
(VIa)

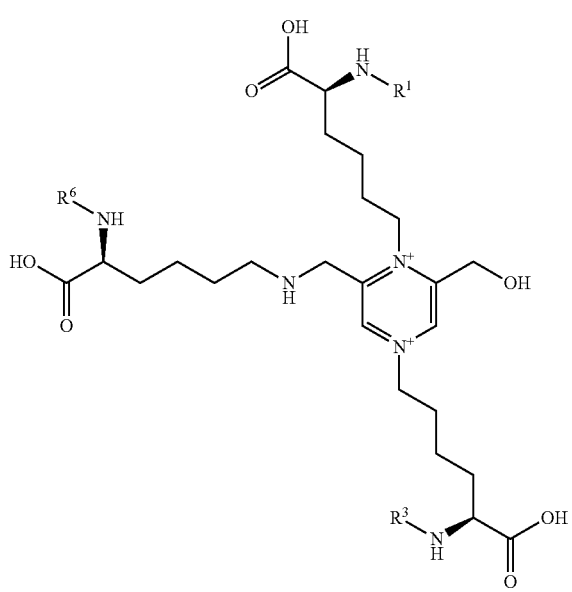
(VIb)

The salt of the compound represented by formula (I) or (II) specifically includes a salt formed at the carboxy group of the compound, and a salt formed at the peptide group thereof.

The cationic radicals of the compounds represented by formula (XI) and formula (XII) are represented by the following formula (XIII) and formula (XIV):

[Chemical Formula 23]

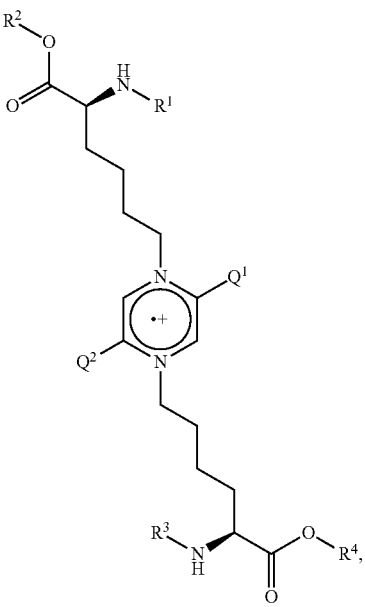
(XIII)

(XIV)

In the formulas, Rt, $R^2$, $R^3$, $R^4$, $Q^1$, and $Q^2$ are as defined in formula (XI) and formula (XII).

The dications of the compounds represented by formula (XI) and formula (XII) are represented by the following formula (XV) and formula (XVI):

[Chemical Formula 24]

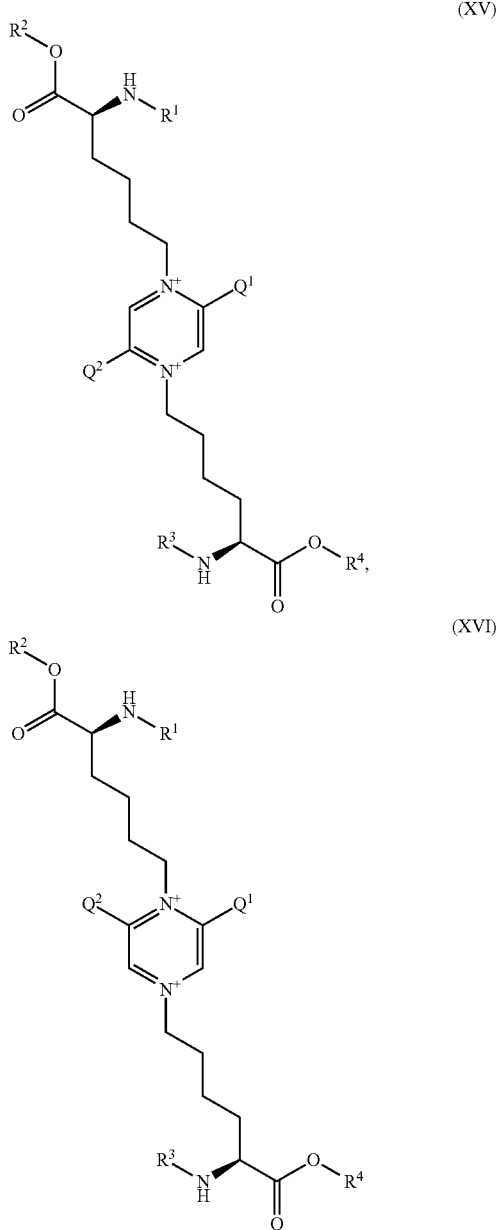

In the formulas, $R^1$, $R^2$, $R^3$, $R^4$, $Q^1$, and $Q^2$ are as defined in formula (XI) and formula (XII).

The salt of the compound represented by formula (XI) or (XII) specifically includes a salt formed at the carboxy group of the compound, and a salt formed at the peptide group thereof. The cation radical and the dication described herein may contain an appropriate anion.

The term "substantially equivalent" used as to an amino acid sequence means that difference in sequence between two amino acid sequences to be compared is relatively small, and the difference in sequence has no substantial influence on specific binding activity against an antigen. The substantially equivalent amino acid sequence may contain a partial alteration of the amino acid sequence. For example, the amino acid sequence may be altered by the deletion or substitution of one to several (e.g., 1 to 3) amino acids constituting the amino acid sequence, or the addition or insertion of one to several (e.g., 1 to 3) amino acids, or a combination thereof. The position of the variation in the amino acid sequence is not particularly limited, and variations may occur at a plurality of positions. The number of amino acids to be altered in the amino acid sequence is the number corresponding to, for example, within 10% of all amino acids indicated, preferably the number corresponding to within 5% of all amino acids, more preferably the number corresponding to within 1% of all amino acids.

In the case of substituting an amino acid, the amino acid to be substituted can be substituted with an amino acid having a side chain similar in biochemical property to the side chain thereof (conservative amino acid substitution). In one embodiment, the substantially equivalent amino acid sequence may contain, for example, one or more conservative substitutions. The conservative amino acid substitution is known to those skilled in the art, and examples thereof include those listed in the following table (e.g., WO2010/146550).

TABLE 1

| Original residue | Conservative substitution | Exemplary substitution |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val: Met: Ala; Phe; norleucine |
| Leu (L) | Ile | norleucine; Ile; Val; Met; Ala: Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu: Met; Phe; Ala; norleucine |

In one embodiment, two amino acid sequences having 80% or higher, 85% or higher, 90% or higher or 95% or higher identity are substantially equivalent. In another embodiment, two amino acid sequences having 80% or higher, 85% or higher, 90% or higher or 95% or higher identity are substantially equivalent when the substitution is a substitution using an amino acid listed in the conservative substitution or exemplary substitution shown in the table described above. In a further alternative embodiment, two amino acid sequences having 80% or higher, 85% or higher, 90% or higher or 95% or higher identity are substantially equivalent when the substitution is a substitution using an amino acid listed in the conservative substitution shown in the table described above.

Naturally occurring amino acids are classified on the basis of common side chain properties into the following groups;
(1) non-polar: norleucine, Met, Ala, Val, Leu, and Ile;
(2) polar, uncharged: Cys, Ser, Thr, Asn, and Gln;

(3) acidic (negatively charged): Asp and Glu;
(4) basic (positively charged): Lys, Arg, and His;
(5) residues influencing the orientation of a chain: Gly and Pro; and
(6) aromatic: Trp, Tyr, and Phe.

In one embodiment, the amino acid to be substituted may be substituted using an amino acid belonging to the same group thereas.

In one embodiment, two amino acid sequences having 80% or higher, 85% or higher, 90% or higher or 95% or higher identity are substantially equivalent. In another embodiment, two amino acid sequences having 80% or higher, 85% or higher, 90% or higher or 95% or higher identity are substantially equivalent when the substitution is a substitution using an amino acid belonging to the same group as that of the amino acid in the groups described above.

Whether or not two amino acid sequences are substantially equivalent can be determined by comparing binding specificity for an antigen between antibodies respectively comprising the amino acid sequences (the sequences of the other regions are identical). For example, when the dissociation constant ($K_d$ value) of a reference antibody for an antigen in a physiological saline environment is defined as A, substantial identity can be certified provided that the $K_d$ value of an antibody to be compared is in the range of $A \times 10^{-1}$ to $A \times 10$.

The nucleic acid according to the present invention is typically an isolated nucleic acid. In the case of, for example, a nucleic acid, such as a cDNA molecule, which is produced by a gene recombination technique, the "isolated nucleic acid" preferably refers to a nucleic acid in a state substantially free from a cellular component, a culture solution, and the like. Likewise, in the case of a nucleic acid that is produced by chemical synthesis, the "isolated nucleic acid" preferably refers to a nucleic acid in a state substantially free from a precursor (raw material) such as dNTP, a chemical substance used in the course of synthesis, and the like.

The term "nucleic acid" herein includes DNA (including cDNA and genomic DNA), RNA (including mRNA), DNA analogs, and RNA analogs. The form of the nucleic acid of the present invention is not limited, i.e., may be any of a single strand and a double strand. Double-stranded DNA is preferred. Also, codon degeneracy is taken into consideration. Specifically, in the case of a nucleic acid encoding a protein, it may have an arbitrary nucleotide sequence as long as the protein is obtained as an expression product thereof.

AGEs are formed through the glycation reaction of a protein. A reducing sugar such as glucose or fructose reacts non-enzymatically with a free amino group of a protein so that an Amadori compound is produced from a Schiff base, followed by repetitions of reactions such as irreversible dehydration, condensation, oxidation, and reduction, leading to the production of yellow-brown complicated substances AGEs having unique fluorescence. On the other hand, compounds obtained through the reaction of an amino acid residue such as lysine with a sugar have been identified as the structures of AGEs, and pyrraline, $N^\varepsilon$-carboxymethyllysine (CML), $N^\varepsilon$-carboxyethyllysine (CEL), and $N^\omega$-carboxymethylarginine (CMA), etc. having no fluorescence are also known as AGEs. In addition, compounds having an aromatic ring, such as argpyrimidine, pentosidine, crossline, GA-pyridine, vesperlysine, and pyrropyridine have been identified as AGEs. Peptides or proteins containing these compounds as amino acid residues are also included in AGEs.

It is assumed that a substrate of the protein glycation reaction to form AGEs is a reducing sugar such as glucose or fructose as well as glyceraldehyde, glycolaldehyde, methylglyoxal, glyoxal, and 3-deoxyglucosone, etc. which are produced by in vivo sugar metabolism or the like. Attempts have been made to form AGEs through the reactions of proteins such as BSA using such reducing sugars and aldehydes. Among various AGEs thus prepared, such as AGEs derived from glyceraldehyde (Glycer-AGEs), AGEs derived from glucose (Glu-AGEs), AGEs derived from glycolaldehyde (Glycol-AGEs), AGEs derived from fructose (Fru-AGEs), AGEs derived from methylglyoxal (MGO-AGEs), AGEs derived from glyoxal (GO-AGEs), and AGEs derived from 3-deoxyglucosone (3-DG-AGEs), AGEs derived from glyceraldehyde are reportedly involved in various diseases such as diabetes mellitus, and an approach of measuring the concentrations of Glycer-AGEs in blood using polyclonal antibodies directed to AGEs derived from glyceraldehyde as antigens is known.

The monoclonal antibody of the present invention can be prepared using, as an antigen, a particular fraction obtained by reacting lysine in which an amino group at α-position is protected with a protecting group (Z group), and glyceraldehyde, and fractionating the resulting AGEs (Glycer-AGEs-Z-Lys). The monoclonal antibody of the present invention has a property of specifically binding to AGEs derived from glyceraldehyde (Glycer-AGEs) and AGEs derived from glycolaldehyde (Glycol-AGEs).

In one aspect, the present invention provides a monoclonal antibody or antigen binding fragment thereof that binds to an epitope in AGEs derived from glyceraldehyde (Glycer-AGEs) and/or AGEs derived from glycolaldehyde (Glycol-AGEs), and does not bind to one or more AGEs selected from AGEs derived from glucose (Glu-AGEs), AGEs derived from fructose (Fru-AGEs), AGEs derived from methylglyoxal (MGO-AGEs), AGEs derived from glyoxal (GO-AGEs), and AGEs derived from 3-deoxyglucosone (3-DG-AGEs). More specifically, there is provided a monoclonal antibody or antigen binding fragment thereof that binds to an epitope in AGEs derived from glyceraldehyde (Glycer-AGEs) and AGEs derived from glycolaldehyde (Glycol-AGEs), and does not bind to AGEs derived from glucose (Glu-AGEs), AGEs derived from fructose (Fru-AGEs), AGEs derived from methylglyoxal (MGO-AGEs), AGEs derived from glyoxal (GO-AGEs), and AGEs derived from 3-deoxyglucosone (3-DG-AGEs). Further specifically, there is provided a monoclonal antibody or antigen binding fragment thereof that binds to an epitope in AGEs derived from glyceraldehyde and AGEs derived from glycolaldehyde, and does not bind to AGEs derived from glucose (Glu-AGEs), AGEs derived from fructose (Fru-AGEs), AGEs derived from methylglyoxal (MGO-AGEs), AGEs derived from glyoxal (GO-AGEs), AGEs derived from 3-deoxyglucosone (3-DG-AGEs), $N^\varepsilon$-carboxymethyllysine (CML), and $N^\varepsilon$-carboxyethyllysine (CEL).

In one aspect, the present invention provides a monoclonal antibody or antigen binding fragment thereof that binds to an epitope in AGEs derived from glyceraldehyde or AGEs derived from glycolaldehyde. In this context, the AGEs derived from glyceraldehyde and the AGEs derived from glycolaldehyde are AGEs resulting from the glycation reaction of a protein such as BSA or mouse serum albumin (MSA) in the presence of glyceraldehyde or glycolaldehyde, and are proteins comprising AGEs. A feature of the monoclonal antibody of the present invention and the antigen binding fragment thereof is that they are directed to a chemical structure resulting from protein glycation reaction as an epitope. In a preferred embodiment, the antibody of the present invention and the antigen binding fragment thereof do not bind to reducing sugars and aldehydes resulting from sugar metabolism or the like, particularly, AGEs derived from glucose, AGEs derived from fructose, AGEs derived from methylglyoxal, AGEs derived from glyoxal, and AGEs derived from 3-deoxyglucosone. These AGEs are prepared by adding each reducing sugar or aldehyde to a protein such as BSA, followed by protein glycation reaction. The binding specificity of the antibody can be identified by an approach known in the art, for example, competitive ELISA.

The present invention provides a monoclonal antibody or antigen binding fragment thereof that binds to an epitope in AGEs derived from glyceraldehyde or AGEs derived from glycolaldehyde. The antibody or the fragment can be used in the treatment, prevention and/or diagnosis of diseases involving AGEs. The antibody that can be used in the present invention can assume a plurality of forms, as described herein. The present invention provides an antibody structure comprising a set of six CDRs (including amino acid sequences substantially equivalent thereto, for example, sequences containing the deletion, substitution, or addition of 1 to 3 amino acid residues), as defined herein.

Conventional antibody structural units typically comprise tetramers. Each tetramer is typically composed of two identical polypeptide chain pairs. Each pair has one "light" chain (typically having a molecular weight of approximately 25 kDa) and one "heavy" chain (typically having a molecular weight of approximately 50 to 70 kDa). Human light chains are classified into κ light chain and λ light chain. Heavy chains are classified into μ, δ, γ, α and ε, and antibody isotypes are defined as IgM, IgD, IgG, IgA and IgE, respectively. IgG has a plurality of subclasses. Examples of the subclasses include, but are not limited to, IgG1, IgG2, IgG3, and IgG4. IgM has subclasses including, but are not limited to, IgM1 and IgM2. Thus, the "isotype" used herein means an arbitrary subclass of an immunoglobulin defined according to the chemical and antigenic features of its constant regions. Known human immunoglobulin isotypes are IgG1, IgG2, IgG3, IgG4, IgA1, IgA2, IgM1, IgM2, IgD and IgE. Therapeutic antibodies also include hybrids of isotypes and/or subclasses. In one embodiment, the antibody of the present invention is IgG, IgA, IgM, IgD or IgE and is preferably IgG.

Each chain contains a variable region of approximately 100 to 110 or more amino acids involved mainly in antigen recognition. In the variable region, three loops are assembled in each of heavy-chain and light-chain V domains to form an antigen binding site. Each loop is also called complementarity determining region (hereinafter, also referred to as "CDR"), and a variation in the amino acid sequence of this moiety is most marked. "Variable" means the fact that a particular segment of the variable region differs in a wide range among antibody sequences. The variability within the variable region is not uniformly distributed. Instead, the V region is composed of relatively invariable stretches of 15 to 30 amino acids, called framework regions (FRs), separated by extremely variable short regions of 9 to 15 amino acids or more in length, called "hypervariable regions".

VH and VL are each composed of three hypervariable regions ("complementarity determining regions", "CDRs") and four FRs, which are arranged from the amino terminus to the carboxy terminus in the following order: FR1-CDR1-FR2-CDR2-FR3-CDR3-FR4. The hypervariable regions generally include about amino acid residues 24 to 34 (VL CDR1; "VL" means a variable region of a light chain), about amino acid residues 50 to 56 (VL CDR2) and about amino acid residues 89 to 97 (VL CDR3) in a light-chain variable region and about amino acid residues 31 to 35 (VH CDR1; "VH" means a variable region of a heavy chain), about amino acid residues 50 to 65 (VH CDR2) and about amino acid residues 95 to 102 (VH CDR3) in a heavy-chain variable region; Kabat et al., SEQUENCES OF PROTEINS OF IMMUNOLOGICAL INTEREST, 5th Ed. Public Health Service, National Institutes of Health, Bethesda, Md. (1991), and/or residues thereof forming hypervariable loops (e.g., residues 26 to 32 (VL CDR1), 50 to 52 (VL CDR2) and 91 to 96 (VL CDR3) in a light-chain variable region and residues 26 to 32 (VH CDR1), 53 to 55 (VH CDR2) and 96 to 101 (VH CDR3) in a heavy-chain variable region; Chothia and Lesk (1987) J. Mol. Biol. 196: 901-917).

When the residues of variable domains (about residues 1 to 107 of a light-chain variable region and about residues 1 to 113 of a heavy-chain variable region) are mentioned herein, the EU numbering system for use in Fc regions as well as the Kabat numbering system is usually used (e.g., Kabat et al., supra (1991)). The identification of CDRs by the Kabat numbering can be performed using generally available software (e.g., abYsis (http://www.abysis.org/).

CDRs contribute to the formation of antigen binding and more specifically contribute to the formation of an epitope binding site of an antibody. The "epitope" means a determinant that interacts with a specific antigen binding site (paratope) in the variable regions of an antibody molecule. Epitopes are divided into groups of molecules such as amino acids and sugar side chains and usually have specific structural properties and specific charge properties. As shown herein, the antibody according to the present invention, called "SJ-5" or "PB-1" herein, is considered to bind to an antigen with a portion or the whole of the structure represented by formula (XI) or (XII), or formula (I) or (I) described above as an epitope.

Various AGEs can be prepared by mixing and reacting a protein (e.g., bovine serum albumin (BSA), mouse serum albumin (MSA), and rabbit serum albumin (RSA)) with an aldehyde or a reducing sugar. For example, BSA containing AGEs derived from glyceraldehyde can be prepared by reacting glyceraldehyde with BSA, and this can be used as a preparation of AGEs. The antibody of the present invention against AGEs derived from glyceraldehyde can be prepared, for example, by selecting an antibody that has binding activity against BSA containing AGEs derived from glyceraldehyde, and does not have binding activity against BSA. In one aspect of the present invention, the epitope to which the antibody of the present invention binds contains a structure produced through non-enzymatic reaction from glyceraldehyde and a protein.

In one aspect, the present invention provides an antibody or antigen binding fragment thereof comprising amino acid sequences defined in the following (1-1) and (1-2) in the complementarity determining regions of a heavy-chain variable region and a light-chain variable region:

(1-1)
(a) VH CDR 1: the amino acid sequence of SEQ ID NO 1, or an amino acid sequence substantially equivalent thereto;
(b) VH CDR2: the amino acid sequence of SEQ ID NO 2, or an amino acid sequence substantially equivalent thereto;
(c) VH CDR3: the amino acid sequence of SEQ ID NO 3, or an amino acid sequence substantially equivalent thereto;

(d) VL CDR1: the amino acid sequence of SEQ ID NO 5, or an amino acid sequence substantially equivalent thereto;
(e) VL CDR2: the amino acid sequence of SEQ ID NO 6, or an amino acid sequence substantially equivalent thereto; and
(f) VL CDR3: the amino acid sequence of SEQ ID NO 7, or an amino acid sequence substantially equivalent thereto; or
(1-2)
(g) VH CDR 1: the amino acid sequence of SEQ ID NO 15, or an amino acid sequence substantially equivalent thereto;
(h) VH CDR2: the amino acid sequence of SEQ ID NO 16, or an amino acid sequence substantially equivalent thereto;
(i) VH CDR3: the amino acid sequence of SEQ ID NO 17, or an amino acid sequence substantially equivalent thereto;
(j) VL CDR1: the amino acid sequence of SEQ ID NO 19, or an amino acid sequence substantially equivalent thereto;
(k) VL CDR2: the amino acid sequence of SEQ ID NO 20, or an amino acid sequence substantially equivalent thereto; and
(l) VL CDR3: the amino acid sequence of SEQ ID NO 21, or an amino acid sequence substantially equivalent thereto.

In one aspect, the present invention provides a monoclonal antibody or an antigen binding fragment thereof, wherein the amino acid sequence of the heavy-chain variable region is the amino acid sequence of SEQ ID NO 4 or an amino acid sequence substantially equivalent thereto, and the amino acid sequence of the light-chain variable region is the amino acid sequence of SEQ ID NO 8 or an amino acid sequence substantially equivalent thereto. In a specific embodiment thereof, the present invention includes the monoclonal antibody SJ-5 described herein. In another aspect, the present invention provides a monoclonal antibody or an antigen binding fragment thereof, wherein the amino acid sequence of the heavy-chain variable region is the amino acid sequence of SEQ ID NO 18 or an amino acid sequence substantially equivalent thereto, and the amino acid sequence of the light-chain variable region is the amino acid sequence of SEQ ID NO 22 or an amino acid sequence substantially equivalent thereto. In a specific embodiment thereof, the present invention includes the monoclonal antibody PB-1 described herein.

In one aspect of the present invention, such an antibody is a mouse-derived antibody and has constant regions of a mouse antibody in addition to the heavy-chain variable region and the light-chain variable region of SEQ ID NOs described above. Examples of the amino acid sequence substantially equivalent to the heavy-chain variable region or the light-chain variable region of SEQ ID NO described above include a sequence in which one or two amino acids are added to the N terminus or the C terminus. Examples of the amino acid sequence substantially equivalent to the heavy-chain variable region of SEQ ID NO described above include a sequence in which one or two amino acids (e.g., amino acids selected from natural amino acids), more specifically, one amino acid selected from Glu and Gln, are added to the N terminus or the C terminus.

In one aspect, the present invention provides an antibody or antigen binding fragment thereof that cross-competes with a reference antibody (the reference antibody is an antibody or antigen binding fragment thereof defined by the above-described heavy-chain variable region and light-chain variable region or their CDRs) for binding to the epitope in AGEs derived from glyceraldehyde or AGEs derived from glycolaldehyde. In one embodiment, the present invention provides an antibody or antigen binding fragment thereof that cross-competes with the monoclonal antibody SJ-5 as a reference antibody for binding to the epitope in AGEs derived from glyceraldehyde or AGEs derived from glycolaldehyde.

The cross-competitive properties of the antibody of the present invention can be confirmed, for example, by standard binding assay to Glycer-AGEs or Glycol-AGEs with the monoclonal antibody SJ-5 as a reference antibody. The cross-competition can be confirmed by, for example, flow cytometry or cross-competitive ELISA assay.

In one aspect, the present invention provides a pharmaceutical composition for treatment, prevention or diagnosis of a disease, comprising the above-described antibody or antigen binding fragment thereof. The target disease is not particularly limited as long as the disease involves Glycer-AGEs or Glycol-AGEs. Examples thereof include diabetes mellitus, diabetic micro-vascular complications (diabetic retinopathy, diabetic nephropathy, and diabetic neuropathy), and diabetic macro-angiopathy, hypertension, dementia such as Alzheimer's disease, cancer (e.g., liver cancer, pancreatic cancer, uterus cancer, colon cancer, rectal cancer, breast cancer, bladder cancer, malignant melanoma, and lung cancer), non-alcoholic steatohepatitis (NASH), and infertility. In another embodiment of the present invention, examples of the disease include diabetes mellitus, glucose intolerance, retinopathy, nephropathy, peripheral neuropathy, leg gangrene, arteriosclerosis, thrombosis, non-alcoholic fatty liver disease, non-alcoholic steatohepatitis, cancer (e.g., melanoma, lung cancer, and liver cancer), polycystic ovarian syndrome, ovarian dysfunction, central nervous disorder, and Alzheimer's disease.

In one aspect of the present invention, the pharmaceutical composition of the present invention can be used for treatment, prevention or diagnosis of a disease caused by endothelial-to-mesenchymal transition promoted by AGEs. Examples of the target disease include cancer (e.g., ovarian cancer, breast cancer, uterine body cancer, prostate cancer, tongue cancer, oral cancer, pharyngeal cancer, esophageal cancer, stomach cancer, colorectal cancer, rectal cancer, pancreatic cancer, lung cancer, liver cancer, and brain tumor), obesity, diabetes mellitus, diabetic disease (e.g., diabetic retinopathy, diabetic cataract, diabetic neuropathy, diabetic cardiomyopathy, diabetic vascular complications, diabetic nephropathy, diabetic renal disease, diabetic foot, diabetic ketoacidosis, and diabetic nephropathy), periodontal disease, age-related macular degeneration, lung disease or respiratory system disease (e.g., pulmonary fibrosis, idiopathic pulmonary fibrosis, peribronchiolar fibrosis, interstitial lung disease, cancer fibrous lung disease, chronic obstructive pulmonary disease, peripheral airway disease, and pulmonary emphysema), renal disease (pyelonephritis, glomerulosclerosis, glomerulonephritis, mesangial proliferative glomerulonephritis, nephrogenic systemic fibrosis, renal interstitial fibrosis, chronic renal disease, etc.), idiopathic retroperitoneal fibrosis, scleroderma, female infertility, polycystic ovarian syndrome, ovarian dysfunction, early ovarian dysfunction, male infertility, liver disease (e.g., cirrhosis and non-alcoholic steatohepatitis), cardiovascular disease (e.g., acute lower limb artery embolism, peripheral arterial disease, atherothrombotic cerebral infarct, atherosclerosis, internal carotid artery stenosis, aortic valve stenosis, aortic insufficiency, angina pectoris, congestive heart failure, acute heart failure, chronic heart failure, ischemic heart disease, dilated cardiomyopathy, cardiac sarcoidosis, hypertension, pulmonary arterial hypertension, cor pulmonale, myocarditis, vascular-stenosing cardiofibrosis, cardiofibrosis after myocardial infarction, left ventricular hypertrophy after myocardial infarction, cerebral infarction, and cerebrovascular disorder), rheumatoid arthritis, lifestyle diseases, dyslipidemia, Alzheimers disease, vascular dementia, uveitis, endocrine disease, and osteoporosis. More specific examples thereof include diabetic retinopathy, diabetic nephropathy, atherothrombotic cerebral infarct, atherosclerosis, chronic renal disease, chronic heart failure and ischemic heart disease.

The pharmaceutical composition of the present invention can be used for diagnosis, treatment, and/or prevention of an eye disease. In one embodiment, the pharmaceutical composition can be used for confirmation of the degree of progression of an eye disease, or estimation of the risk of developing an eye disease. In another embodiment, the pharmaceutical composition can be used for treatment for preventing or delaying the progression of a developed eye disease, and can be administered on a regular basis over a long period, for example. In a further alternative embodiment, the pharmaceutical composition can be preventively administered to a subject having a high risk of developing a disease. In a further alternative embodiment, the pharmaceutical composition can be used for treatment for recovering a development site of a developed eye disease.

Examples of the eye disease suitable for use of the pharmaceutical composition of the present invention include diabetic retinopathy, diabetic cataract, retinitis pigmentosa, diabetic macular edema, amaurosis congenita of Leber, Stargardt disease, Usher syndrome, choroideremia, cone-rod dystrophy, cone dystrophy, progressive retinal atrophy, age-related macular degeneration, macular dystrophy, choroidal sclerosis, total choroidal vascular atrophy, cystoid macular edema, uveitis, retinal detachment, macular hole, macular telangiectasia, glaucoma, optic neuropathy, ischemic retinal disease, retinopathy of prematurity, retinal vascular occlusion, and retinal microaneurysms. Examples of a more suitable eye disease include diabetic retinopathy, diabetic macular edema, retinitis pigmentosa and age-related macular degeneration.

The pharmaceutical composition of the present invention is effective for reducing or eliminating the effect of suppressing the lumen formation of vascular endothelial cells by AGEs and further for suppressing or inhibiting the endothelial-to-mesenchymal transition of vascular endothelial cells induced by AGEs. Such effects reduce or eliminate increased vascular permeability ascribable to the inhibition of lumen formation and suppresses cancer metastasis. Thus, in one embodiment, the pharmaceutical composition of the present invention can be used for prevention or suppression of cancer metastasis.

In one aspect, the present invention provides a method for diagnosing a disease, comprising the step of measuring the amounts of Glycer-AGEs and Glycol-AGEs present in a target tissue (e.g., blood) using the antibody of the present invention or the antigen binding fragment thereof. In this context, the diagnosis is as already described. In another embodiment, the present invention provides a method for analyzing a sample (e.g., a blood sample obtained by blood collection), comprising the step of measuring the amounts of Glycer-AGEs and Glycol-AGEs present in the sample using the antibody of the present invention or the antigen binding fragment thereof.

The antigen binding fragment of the antibody of the present invention is, for example, Fab, Fab', F(ab')$_2$, Fv, scFv, dsFv, diabody, or sc(Fv)$_2$. The antibody of the present invention is, for example, a mouse antibody, a humanized antibody, a human antibody, or a chimeric antibody. These antibodies or antigen binding fragments thereof can be prepared by methods known to those skilled in the art.

The antigen binding fragment of the antibody of the present invention binds to an epitope in AGEs derived from glyceraldehyde or AGEs derived from glycolaldehyde, with equilibrium dissociation constant $K_d$ of, for example, $1\times10^{-4}$ M or less, specifically $1\times10^{-5}$ M or less, more specifically $1\times10^{-6}$ M or less, further specifically $1\times10^{-7}$ M or less, preferably $1\times10^{-8}$ M or less. The $K_d$ value of the antibody can be determined by use of a method sufficiently established in the art. The method for determining the $K_d$ value of the antibody is preferably based on use of surface plasmon resonance, preferably use of a biosensor system such as Biacore® system.

In one aspect, the present invention provides a method for preparing a monoclonal antibody or antigen binding fragment thereof that binds to an epitope in AGEs derived from glyceraldehyde or AGEs derived from glycolaldehyde. The method comprises the step of culturing a host cell transfected with a nucleic acid encoding the antibody of the present invention and can be carried out by various methods on the basis of a well-known technique.

In one aspect, the present invention provides a nucleic acid encoding the antibody of the present invention. Such a polynucleotide encodes, for example, both the respective variable regions and constant regions of a heavy chain and a light chain. The polynucleotide may be in the form of RNA or may be in the form of DNA. A coding sequence encoding a polypeptide may contain redundancy or degeneracy of a genetic code.

In some embodiments, one or more nucleic acids encoding the antibody of the present invention are incorporated in an expression vector. The expression vector can be designed so as to reside outside the chromosome of a host cell for introduction or to be integrated in the genome thereof. The expression vector can comprise arbitrary numbers of appropriate control sequences (examples thereof include, but are not limited to, transcriptional and translational regulatory sequences, a promoter, a ribosomal binding site, an enhancer, and a replication origin) or other factors (selection gene, etc.), and all of these are operably linked as well known in the art. In some cases, two nucleic acids are used and can be respectively placed in different expression vectors (e.g., a nucleic acid encoding a heavy chain in the first expression vector and a nucleic acid encoding a light chain in the second expression vector) or can be placed in the same expression vector. The design of one or more expression vectors, including the selection of control sequences, can depend on factors such as the selection of a host cell and the expression level of the desired protein.

In general, one or more nucleic acids are introduced to a nucleic acid and/or a host cell suitable for expression by use of an arbitrary method (e.g., transformation, transfection, electroporation, and infection) suitable for the selected host cell so as to be operably linked to one or more expression regulation factors (e.g., in a vector, in a construct prepared by a process in a cell, or to be integrated in the genome of the host cell), to prepare a recombinant host cell. The obtained recombinant host cell can be maintained under conditions suitable for expression (e.g., in the presence of an inducer, in a suitable non-human animal, or in a medium supplemented with a suitable salt, growth factor, antibiotic, nutritious supplement, and the like) to prepare one or more polypeptides encoded thereby. In some cases, a heavy chain is prepared in one cell, and a light chain is prepared in another cell.

A mammal cell line utilizable as a host for expression is known in the art and includes many immortalized cell lines available from American Type Culture Collection (ATCC), Manassas, VA. Examples thereof include, but are not limited to, Chinese hamster ovary (CHO) cells, HEK 293 cells, NSO cells, HeLa cells, baby hamster kidney (BHK) cells, monkey kidney cells (COS), human liver cancer cells (e.g., Hep G2), and a large number of other cell lines. A recombinant antibody can also be expressed using a non-mammal (including, but not limited to, bacteria, yeasts, insects and plants) cell. In some embodiments, the antibody can be prepared in a transgenic animal such as cattle or a chicken.

In one aspect, the present invention provides a method for preparing an antibody by immunizing an animal with a compound of formula (XI) or formula (XII), or formula (I) or formula (II) as an antigen. The method for preparing the compound of formula (XI) or formula (XII), or formula (I) or formula (II) is not particularly limited. For example, it can be prepared by purifying a reaction mixture obtained by reacting lysine in which an amino group at α-position is protected and glyceraldehyde. For example, among fractions obtained by fractionating the reaction mixture described above, a fraction containing a compound represented by formula (Ia) or formula (Ib) can be used as the antigen for use in immunization. The fractionation can be performed by a usual method. For example, a fraction containing a particular peak according to HPLC fractionation can be used.

The immunization can employ a method that is usually performed in antibody preparation. A non-human mammal, for example, a mouse, a rat, a rabbit, a dog, a pig, or a hamster, can be used as the animal.

EXAMPLES

[Example 1] Preparation of AGEs

AGEs can be prepared by a method known in the art (NPL 5 and NPL 6, etc.). Specifically, various AGEs were prepared by the following methods.

(1) Bovine Serum Albumin Containing AGEs Derived from Glyceraldehyde (Glycer-AGEs-BSA)

Bovine serum albumin (BSA, Sigma-Aldrich Co. LLC), DL-glyceraldehyde (DL-GLA, Nacalai Tesque, Inc.), and diethylenetriamine-N,N,N',N'',N''-pentaacetic acid (DTPA, Dojindo Laboratories) were obtained by purchase.

DL-GLA (180 mg) and DTPA (39 mg) were weighed and transferred to a 50 mL tube for culture. A phosphate buffer solution (0.2 M, pH 7.4, 20 mL) was added to the tube and stirred with a vortex mixer until DL-GLA was dissolved. Then, BSA (500 mg) was added thereto and stirred until dissolved (concentration of BSA in the solution: 25 mg/mL).

The obtained mixture was passed through a 0.2 pm filter in a clean bench to prepare an aseptic solution. The cap of the tube was hermetically sealed with a film such as Parafilm™ so as not to evaporate the liquid in the tube, followed by incubation at 37° C. for 1 week.

The obtained reaction solution (2.5 mL/column) was applied to PD-10 columns (GE Healthcare Japan Corp., 8 columns) and eluted with phosphate-buffered saline (PBS) (pH 7.4, 3.5 mL/column) according to the protocol of the PD-10 columns.

The eluates (a total of 14 mL) from 4 columns were collected and placed in dialysis tubes (Spectra/Por Dialysis Membrane, width: 23 mm) with a molecular weight cutoff of 6 to 8 kDa, and two tubes of 14 mL were placed in 2 L of PBS cooled in advance, stirred, and dialyzed. The dialysis was performed in a low-temperature chamber (5° C.), and performed for 3 days with the dialysis solution (PBS) replaced every 24 hours.

After the completion of the dialysis, the liquids in the two dialysis tubes were combined and placed in a 50 mL tube for culture, and the amount of a protein as BSA containing AGEs derived from glyceraldehyde (Glycer-AGEs-BSA) was measured and adjusted to a necessary protein concentration with PBS for culture.

Control BSA was prepared by the same approach as in Example 1 except that DL-GLA was not added.

(2) Mouse Serum Albumin Containing AGEs Derived from Glyceraldehyde (Glycer-AGEs-MSA) and Rabbit Serum Albumin Containing AGEs Derived from Glyceraldehyde (Glycer-AGEs-RSA)

A solution containing 25 mg/mL mouse serum albumin (MSA, Sigma-Aldrich Co. LLC) or rabbit serum albumin (RSA, Sigma-Aldrich Co. LLC), DL-glyceraldehyde (0.1 M, Nacalai Tesque, Inc.), and diethylenetriaminepentaacetic acid (5 mM, DTPA, Dojindo Laboratories) was prepared in a 0.2 M phosphate buffer solution (pH 7.4). The solution was rendered aseptic by sterilization through a 0.2 pm filter and incubated at 37° C. for 1 week. Low-molecular-weight unreacted matter or the like was removed using a PD-10 gel filtration column (GE Healthcare Japan Corp.), and dialysis was further performed for 3 days (during which PBS was replaced everyday) with PBS (phosphate-buffered saline) in a low-temperature chamber (5° C.).

(3) BSA Containing AGEs Derived from Glucose (Glu-AGEs-BSA) and BSA Containing AGEs Derived from Fructose (Fru-AGEs-BSA)

A solution containing 25 mg/mL bovine serum albumin (BSA, Sigma-Aldrich Co. LLC), D-glucose (0.5 M, FUJIFILM Wako Pure Chemical Corp.) or D-fructose (0.5 M, FUJIFILM Wako Pure Chemical Corp.), and DTPA (5 mM, Dojindo Laboratories) was prepared in a 0.2 M phosphate buffer solution (pH 7.4), and the solution was rendered aseptic by sterilization through a 0.2 pm filter and incubated at 37° C. for 8 weeks. Low-molecular-weight unreacted matter or the like was removed using a PD-10 gel filtration column, and dialysis was further performed for 3 days (during which PBS was replaced everyday) with PBS in a low-temperature chamber (5° C.).

(4) BSA Containing AGEs Derived from Glycolaldehyde (Glycol-AGEs-BSA), BSA Containing AGEs Derived from Methylglyoxal (MGO-AGEs-BSA), and BSA Containing AGEs Derived from Glyoxal (GO-AGEs-BSA)

A solution containing 0.1 M glycolaldehyde (Sigma-Aldrich Co. LLC), methylglyoxal (Sigma-Aldrich Co. LLC), or glyoxal (Sigma-Aldrich Co. LLC), BSA (25 mg/mL) and DTPA (5 mM) was prepared in a 0.2 M phosphate buffer solution (pH 7.4). The solution was rendered aseptic by sterilization through a 0.2 pm filter and incubated at 37° C. for 1 week. After incubation at 37° C. for 1 week under aseptic conditions, low-molecular-weight unreacted matter or the like was removed using a PD-10 gel filtration column, and dialysis was further performed for 3 days (during which PBS was replaced everyday) with PBS in a low-temperature chamber (5° C.).

(5) BSA Containing AGEs Derived from 3-Deoxyglucosone (3-DG-AGEs-BSA)

A solution containing BSA (25 mg/mL, Sigma-Aldrich Co. LLC), 3-deoxyglucosone (0.2 M, Dojindo Laboratories) and DTPA (5 mM) was prepared in a 0.2 M phosphate buffer solution (pH 7.4). The solution was rendered aseptic by sterilization through a 0.2 pm filter and incubated at 37° C. for 2 weeks. Then, low-molecular-weight unreacted matter or the like was removed using a PD-10 gel filtration column, and dialysis was further performed for 3 days (during which PBS was replaced everyday) with PBS in a low-temperature chamber (5° C.).

(6) BSA Containing N-Carboxymethyllysine (CML-BSA)

A solution containing BSA (50 mg/mL, Sigma-Aldrich Co. LLC), glyoxylic acid (45 mM, FUJIFILM Wako Pure Chemical Corp.) and sodium cyanoborohydride (150 mM, Sigma-Aldrich Co. LLC) was prepared in a 0.2 M phosphate buffer solution (pH 7.4). The solution was rendered aseptic by sterilization through a 0.2 pm filter and incubated at 37° C. for 24 hours. Then, low-molecular-weight unreacted matter or the like was removed using a PD-10 gel filtration column, and dialysis was further performed for 3 days (during which PBS was replaced everyday) with PBS in a low-temperature chamber (5° C.).

[Example 2] Preparation of Antigen (1) Preparation of Lysine in Form of AGEs Derived from Glyceraldehyde (Glycer-AGEs-Z-Lys)

$N^\alpha$-Carbobenzoxy-L-lysine (Z-Lys-OH, Tokyo Chemical Industry Co., Ltd.) and DL-glyceraldehyde (DL-GLA, Nacalai Tesque, Inc.) were obtained by purchase. DL-GLA (675.6 mg) was weighed and transferred to a 50 mL centrifugal tube. A phosphate buffer solution (0.2 M, pH 7.4, 25 mL) was added to the centrifugal tube and stirred with a vortex mixer until DL-GLA was dissolved. Then, Z-Lys-OH (700.8 mg) was added thereto and stirred until dissolved (concentration of DL-GLA in the solution: 300 mM, Z-Lys-OH concentration: 100 mM). Then, the cap of the tube was hermetically sealed with a film such as Parafilm™ so as not to evaporate the liquid in the centrifugal tube, followed by still standing at 37° C. for 1 week or longer.

1 mL of an aqueous solution of 10% trifluoroacetic acid (TFA, FUJIFILM Wako Pure Chemical Corp.) was added to 5 mL of the obtained reaction solution and mixed by inversion. Then, a supernatant was removed by centrifugation (12,000×g) at room temperature for 10 minutes. Ultrapure water (5 mL) was added to the centrifugal tube containing the obtained precipitates, which was then centrifuged again to remove a supernatant. This operation was carried out a total of three times to wash the precipitates. The precipitates thus washed were dried in air, then measured as to dry weight (200 mg), and refrigerated.

(2) Preparative Purification of Glycer-AGEs-Z-Lys

Figure 6:
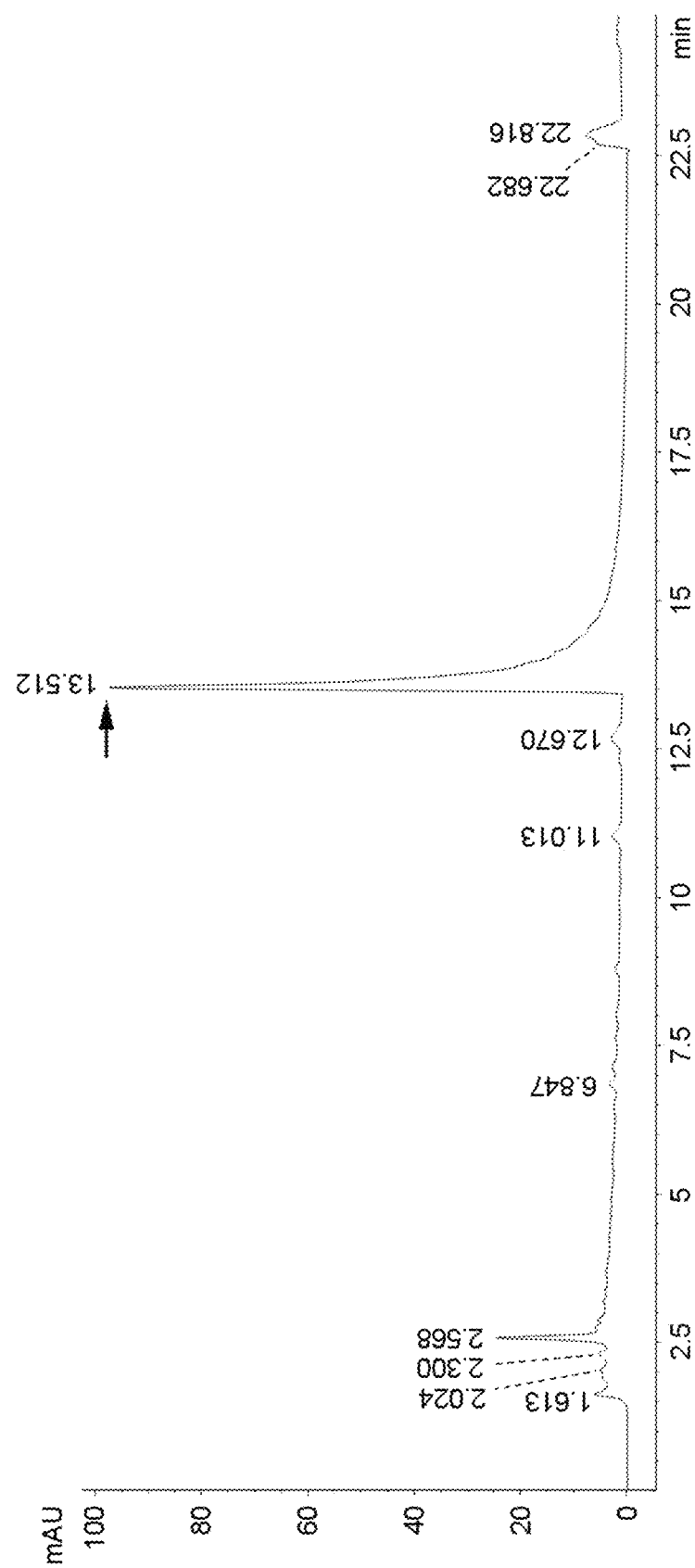
FIG. 6 is a diagram showing results of analysis of Glycer-AGEs-Z-Lys by HPLC (diode array detection (260 nm)).
Figure 7:
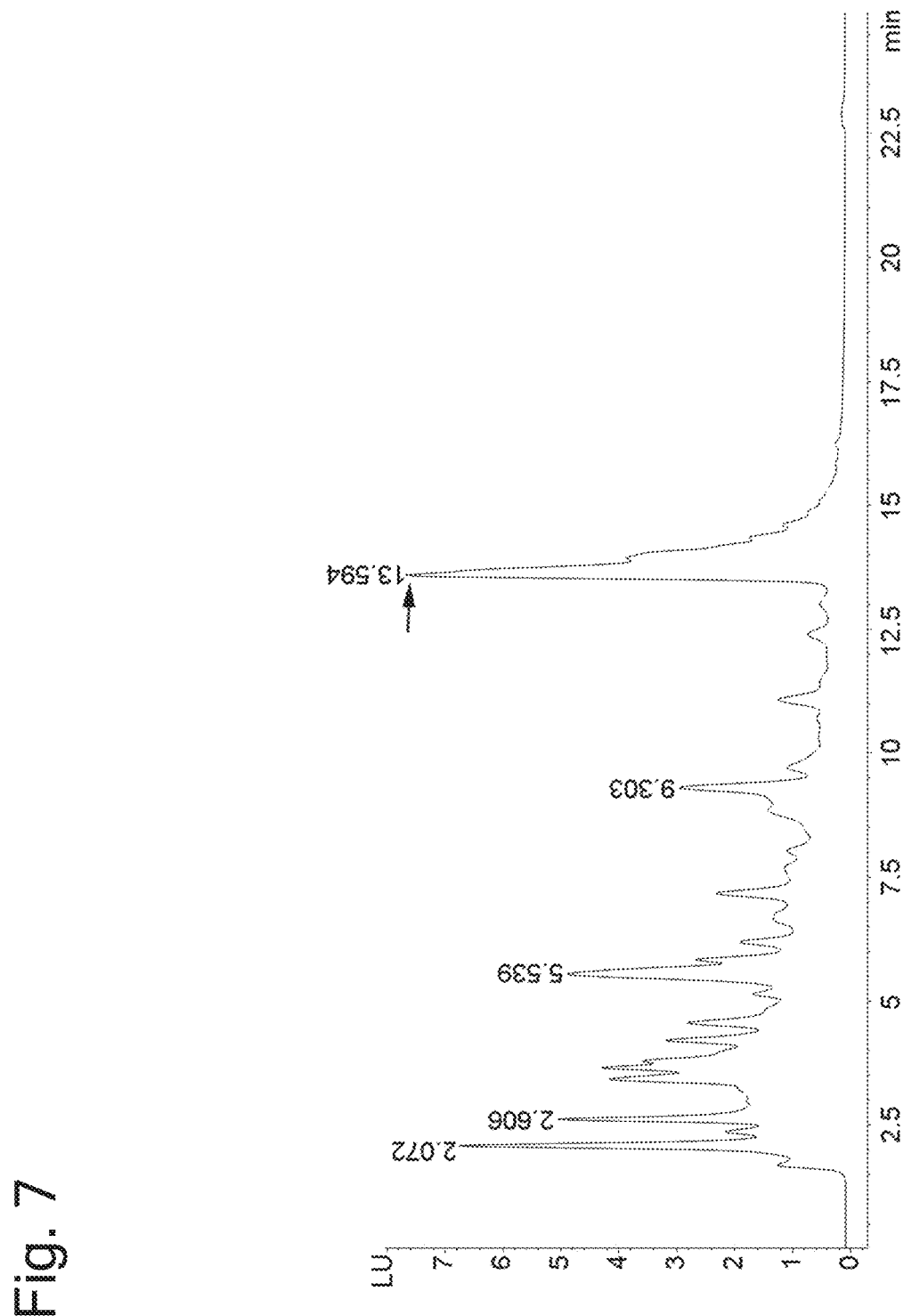
FIG. 7 is a diagram showing results of analysis of Glycer-AGEs-Z-Lys by HPLC (fluorescent detection (Ex 350 nm, Em 450 nm)).

The precipitates of Glycer-AGEs-Z-Lys were dissolved in a phosphate buffer solution (0.2 M, pH 7.4) to prepare a 0.5 mg/mL (for analysis) or 50 mg/mL (for fractionation) sample solution. Then, filtration was performed through a syringe filter (Millex-LG, Merck KGaA) with a pore size of 0.2 pm, and the filtrate was used as a sample for high-performance liquid chromatography (HPLC). The HPLC apparatus used was 1260 Infinity II system (Agilent Technologies, Inc.) and was composed of the following modules: a quaternary pump (G7111B), a multisampler (G7167A), a multicolumn thermostat (G7116A), a diode array detector (G7115A), a fluorescence detector (G7121B), a fraction collector (G1364F), and OpenLAB CDS ChemStation software. Mobile phases were prepared from HPLC solvents of FUJIFILM Wako Pure Chemical Corp. Mobile phase A was a 10 mM aqueous ammonium acetate solution containing 10 mL of a 1 M ammonium acetate solution mixed with 990 mL of distilled water, and mobile phase B was acetonitrile. The sample flowed in mobile phase A:B=75:25 at an analysis time from 0 to 10 minutes, in mobile phase A:B=65:35 at an analysis time from 10.1 to 20 minutes, and in mobile phase A:B=10:90 at an analysis time from 20.1 to 25 minutes. The analysis column used was YMC-Triart $C_{18}$ (150×4.6 mm, YMC Co., Ltd.), and the flow rate was set to 0.8 mL/min. 5 μL of the sample solution for analysis (0.5 mg/mL) thus filtered was injected to the HPLC apparatus, and the peak of Glycer-AGEs-Z-Lys was detected with the diode array detector (260 nm) and the fluorescence detector (excitation wavelength: 350 nm, fluorescence wavelength: 450 nm). The results of HPLC are shown in FIG. 6 (diode array detection (260 nm)) and FIG. 7 (fluorescence detection (Ex 350 nm, Em 450 nm)).

As a result, a marked peak was found at an analysis time of 13.5 minutes. Hereinafter, this peak is designated as GAL13. Subsequently, YMC-Triart C18 (150×10 mm, YMC Co., Ltd.) was attached to the HPLC apparatus, and the flow rate was set to 2.5 mL/min. 50 μL of the sample solution for fractionation (50 mg/mL) thus filtered was injected to the HPLC apparatus, and GAL13 was detected in the diode array detector (260 nm). Then, GAL13 was fractionated in the fraction collector with a UV peak set to a trigger.

Acetonitrile contained in the fractionation solution was removed with a rotary evaporator (Tokyo Rikakikai Co., Ltd.). 1 mL of a 10% aqueous TFA solution was added to 5 mL of the residue solution and mixed by inversion. Then, a supernatant was removed by centrifugation (12,000×g) at room temperature for 10 minutes. Ultrapure water (5 mL) was added to the obtained precipitates, which were then centrifuged again to remove a supernatant. This operation was carried out a total of three times to wash the precipitates. The precipitates were thus washed where dried in air, then measured as to dry weight (1 mg), and refrigerated.

(3) Binding of GAL13 to Carrier Protein

The dry powder of GAL13 after the preparative purification was dissolved in a phosphate buffer solution (0.2 M, pH 7.4) to adjust the final concentration to 40 mg/mL. This solution was further diluted 10-fold with phosphate-buffered saline (PBS, pH 7.4) to adjust the final concentration to 4 mg/mL. A solution of a carrier protein was prepared as follows: a freeze-dried powder of mouse serum albumin (MSA, Sigma-Aldrich Co. LLC) was dissolved in PBS to adjust the final concentration to 10 mg/mL. The 4 mg/mL GAL13 solution (500 μL) and the 10 mg/mL MSA solution (200 μL) were mixed in 1.5 mL Eppendorf Safe-Lock Tubes (Eppendorf AG). Subsequently, 1-ethyl-3-(3-dimethylaminopropyl)carbodiimide hydrochloride (EDC, Thermo Fisher Scientific Inc.) was dissolved in ultrapure water to prepare a 10 mg/mL aqueous solution. A 10 mg/mL aqueous EDC solution (100 μL) was quickly added to the mixed solution of GAL 13 and MSA (700 μL), mixed by inversion, and then incubated overnight at room temperature.

After the completion of the reaction, the reaction solution was immediately subjected to gel filtration through Zeba Spin Desalting Columns (7K MWCO, Thermo Fisher Scientific Inc.). Dialysis was further performed at a low temperature (4° C.) using Slide-A-Lyzer MINI Dialysis Device (3.5K MWCO, Thermo Fisher Scientific Inc.). PBS was used as an external dialysis solution. Three hours after the start of the dialysis, the external solution was replaced, and dialysis was further performed overnight. After the completion of the dialysis, the solution in the dialysis device was recovered and concentrated with Amicon Ultra-0.5 (30K MWCO, Merck KGaA). The protein concentration of MSA cross-linked with GAL13 (GAL13-MSA) was determined with Pierce BCA Protein Assay Kit (Thermo Fisher Scientific Inc.) and adjusted to an arbitrary protein concentration with PBS. GAL13-MSA was used as an immunizing antigen for mouse monoclonal antibody preparation.

For enzyme-linked immunosorbent assay (ELISA), GAL13 was cross-linked to bovine serum albumin (BSA, Sigma-Aldrich Co. LLC) and used as GAL13-BSA in the test. For a negative control group, $N^\alpha,N^\alpha$-dicarbobenzoxy-L-lysine (Z-Lys(Z)—OH, Watanabe Chemical Industries, Ltd.) was cross-linked to BSA to prepare Z-Lys-BSA. These samples were sterilized by filtration through a filter (pore size: 0.22 pm) in a clean bench, if necessary.

[Example 3] Preparation of Monoclonal Antibody (1) Immunization of Mouse

Mouse serum albumin modified with the novel structure derived from Glycer-AGEs (GAL13-MSA, 1 mg/mL) was mixed as an immunizing antigen with the same volume thereas of Freund's Adjuvant, Complete (Sigma-Aldrich Co. LLC) to prepare an emulsion (concentration of the antigen: 0.5 mg/mL), with which five BALB/c mice were subcutaneously immunized at their backs for initial immunization (amount of the antigen: 200 µg/animal). Booster immunization (amount of the antigen: 50 µg/animal) was performed every 1 week using an emulsion (concentration of the antigen: 0.5 mg/mL) prepared by mixing GAL13-MSA (1 mg/mL) with the same volume thereas of Freund's Adjuvant, Incomplete (Sigma-Aldrich Co. LLC). After six shots from the initial immunization, blood was collected from the tail veins, and the antibody titers were confirmed. An emulsion for booster immunization (amount of the antigen. 50 µg) was intraperitoneally administered as a final shot to a mouse having a high antibody titer, and the spleen was excised for cell fusion 3 days later.

(2) Measurement of Antibody Titer

The titer of antiserum was evaluated by ELISA. Bovine serum albumin modified with the novel structure derived from Glycer-AGEs (GAL13-BSA) in which the carrier protein in the immunizing antigen GAL13-MSA was changed to BSA was added at 50 µL/well with a concentration of 1 µg/mL to a 96-well microtiter plate (NUNC) and immobilized overnight at 4° C. The plate was washed three times with PBS containing 0.05% (v/v) Tween 20 (PBS-T) and then blocked with a carbonate buffer solution (pH 9.5) containing 0.5% (w/v) gelatin for 1 hour. The antiserum was serially diluted into 3-fold dilutions from 1000-fold to 729000-fold to prepare dilution series, which were then added at 50 µL/well to the antigen-immobilized plate and left standing for 1 hour. After washing, a secondary antibody (horseradish peroxidase (HRP)-labeled anti-mouse IgG (Zymed Laboratories, Inc.)) diluted 2500-fold with PBS-T was added at 50 µL/well and left standing for 1 hour. After washing, an o-phenylenediamine solution (100 µL) prepared into 0.5 mg/mL with a 0.1 M citrate-phosphate buffer solution (pH 5.0) containing 0.02% (w/v) hydrogen peroxide was added to each well and left standing at 25° C. for 10 minutes. Then, color reaction was terminated by the addition of a 1 M sulfuric acid solution (100 µL) to each well. Then, absorbance at 490 nm was measured with a microplate reader. As a result, a mouse, 9000-fold or higher dilution solutions of the antiserum of which exhibited significant reactivity with the antigen was used for cell fusion.

(3) Preparation of Spleen Cell and Cell Fusion

The spleen excised from the mouse was ground to prepare approximately $1\times10^8$ spleen cells per animal. Myeloma cells P3U1 were cultured, and P3U1 having a live cell ratio of 95% or more on the day of cell fusion was prepared. The spleen cells and P3U1 were mixed at 5:1 (ratio of the number of cells) and subjected to cell fusion using polyethylene glycol with a molecular weight of 1,450 and a concentration of 50% (w/v). The cells thus fused were washed with a medium and suspended in HAT medium, and the cells were seeded at $1\times10^5$ cells/well to the wells of a 96-well culture plate and cultured for hybridoma selection. On cell fusion day 10, the hybridoma culture supernatant was recovered, and an antibody titer in the culture supernatant was measured.

(4) Screening for Antibody Production-Positive Well

The culture supernatant on day 10 after the cell fusion was recovered and screened for an antibody production-positive well by the antibody titer measurement method described above. A clone positive to GAL13-BSA and BSA containing AGEs derived from glyceraldehyde (Glycer-AGEs-BSA) and negative to bovine serum albumin modified with Z-lysine (Z-Lys-BSA) was selected.

(5) Cloning

A clone having high specificity for GAL13-BSA was cloned by the limiting dilution method. Specifically, the cells were prepared into 5 cells/mL with RPMI medium containing 10% FCS and added at 200 µL/well to two 96-well culture plates. Ten days later, a clone was obtained which was confirmed to be positive to GAL13-BSA and Glycer-AGEs-BSA and negative to Z-Lys-BSA in the culture supernatant and was derived from each well. Cells producing a novel monoclonal antibody SJ-5 as the antibody of the present invention having sufficient specificity were obtained.

(6) Purification of Antibody

The cells producing the novel monoclonal antibody SJ-5 were cultured in RPMI medium containing 10% FCS, then washed with PBS, and cultured in a serum-free medium (SMF medium, Thermo Fisher Scientific Inc.) for 4 days to 6 days to obtain a culture supernatant. An IgG fraction was purified from the culture supernatant through Protein G column (manufactured by GE Healthcare Japan Corp.) to obtain the novel monoclonal antibody SJ-5 as the antibody of the present invention having sufficient specificity.

[Example 4] Method for Labeling Monoclonal Antibody and Polyclonal Antibody with Peroxidase (POD)

The obtained novel monoclonal antibody SJ-5 (PBS solution, 200 µg) or an anti-glyceraldehyde-derived AGEs polyclonal antibody (according to the method of Takeuchi et al., described in Molecular Medicine 6 (2): 114-125, 2000; PBS solution, 200 µg) was labeled with POD using Peroxidase Labeling Kit-SH (Dojindo Laboratories). The labeling method followed the procedures of the instruction manual. The obtained POD-labeled antibody solution was mixed with glycerol (Sigma-Aldrich Co. LLC) at 1:1 and stored at $-20°$ C.

[Example 5] Confirmation of Reactivity of Novel Monoclonal Antibody by Direct ELISA BSA modified with the novel structure derived from Glycer-AGEs (GAL13-BSA) was added at 100 µL/well with a concentration of 1 µg/mL and immobilized overnight at 4° C. The plate was washed three times with PBS containing 0.05% (v/v) Tween 20 (PBS-T) and then blocked with PBS-T containing 0.5% (w/v) gelatin for 1 hour. The POD-labeled novel monoclonal antibody SJ-5 prepared in Example 4 and the anti-glyceraldehyde-derived AGEs polyclonal antibody as a control were serially diluted into 4-fold dilutions from 4 μg/mL to 0.06254 μg/mL to prepare dilution series, which were then added at 100 μL/well to the antigen-immobilized plate and left standing for 1 hour. After washing, an o-phenylenediamine solution (100 μL) prepared into 0.5 mg/mL with a 0.1 M citrate-phosphate buffer solution (pH 5.0) containing 0.02% (w/v) hydrogen peroxide was added to each well and left standing at 25° C. for 10 minutes. Then, color reaction was terminated by the addition of a 1 M sulfuric acid solution (50 μL) to each well. Then, absorbance at 490 nm was measured with a microplate reader.

As a result, as shown in FIG. 1, the POD-labeled SJ-5 antibody was shown to react favorably with GAL13-BSA.

Figure 2:
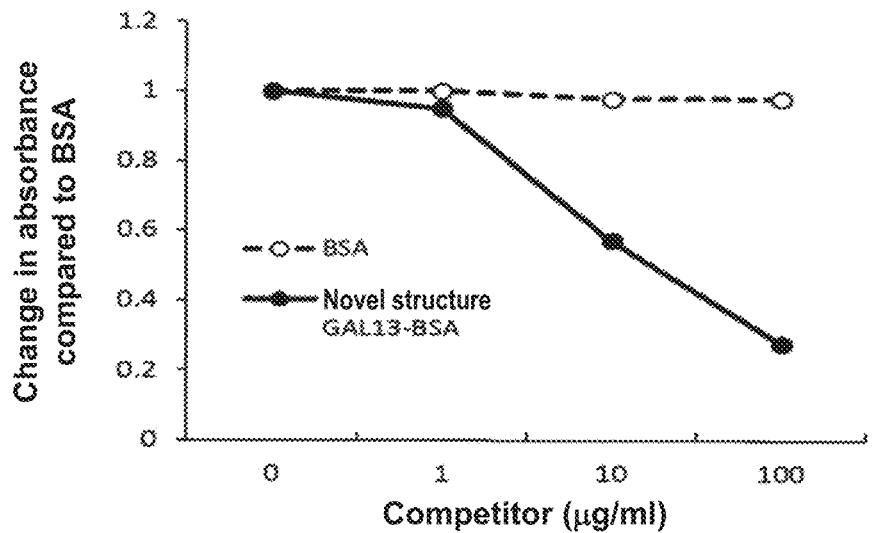
FIG. 2 is a graph showing results of a reactivity confirmation test of an anti-Glycer-AGEs polyclonal antibody by direct ELISA.
Figure 3:
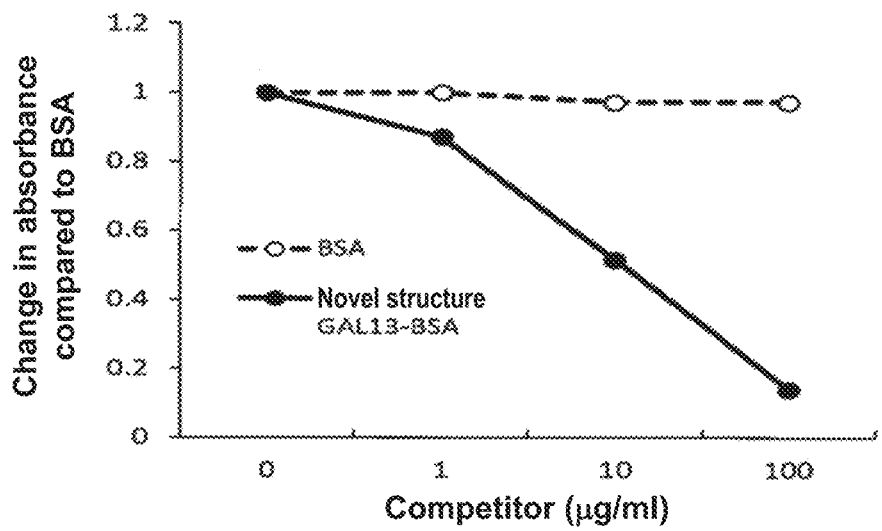
FIG. 3 is a graph showing results of a reactivity confirmation test of a POD-labeled SJ-5 antibody by direct ELISA.

[Example 6] Confirmation of Reactivity of Novel Monoclonal Antibody by Competitive ELISA GAL13-BSA was added at 100 μL/well with a concentration of 1 μg/mL and immobilized overnight at 4° C. The plate was washed three times with PBS containing 0.05% (v/v) Tween 20 (PBS-T) and then blocked with a carbonate buffer solution (pH 9.5) containing 0.5% (w/v) gelatin for 1 hour. After preparation of a POD-labeled SJ-5 antibody (0.4 μg/mL) and an anti-glyceraldehyde-derived AGEs polyclonal antibody (6 μg/mL) as a control, 10-fold serial dilution solutions (50 μL each) of GAL13-BSA or control BSA and the POD-labeled SJ-5 antibody or the anti-glyceraldehyde-derived AGEs polyclonal antibody as a control (50 μL) were added to the antigen-immobilized plate, stirred with a plate mixer, and then left standing at room temperature for 1 hour. After washing, an o-phenylenediamine solution (100 μL) prepared into 0.5 mg/mL with a 0.1 M citrate-phosphate buffer solution (pH 5.0) containing 0.02% (w/v) hydrogen peroxide was added to each well and left standing at 25° C. for 10 minutes. Then, color reaction was terminated by the addition of a 1 M sulfuric acid solution (50 μL) to each well. Then, absorbance at 490 nm was measured with a microplate reader. FIG. 2 shows the results about the anti-glyceraldehyde-derived AGEs polyclonal antibody. FIG. 3 shows the results about the POD-labeled SJ-5 antibody.

Both the POD-labeled SJ-5 antibody and the anti-glyceraldehyde-derived AGEs polyclonal antibody were also shown to react favorably with GAL 13-BSA in the competitive method and were shown to produce similar results using the POD-labeled SJ-5 antibody at an antibody concentration 15 times lower than that of the anti-glyceraldehyde-derived AGEs polyclonal antibody.

[Example 7] Confirmation of Specificity of Novel Monoclonal Antibody by Competitive ELISA GAL13-BSA or Glycer-AGEs-BSA prepared into 1 μg/mL with PBS (pH 7.4) was added as an immobilized antigen at 100 μL/well to a 96-well microtiter plate (NUNC) and left at 25° C. for 1 hour. The antigen was immobilized overnight at 4° C. The plate was washed three times with PBS containing 0.05% (v/v) Tween 20 (PBS-T) and then blocked with a carbonate buffer solution (pH 9.5) containing 0.5% (w/v) gelatin for 1 hour. A POD-labeled SJ-5 antibody (0.4 μg/mL) was prepared under the same conditions as in Example 6. In order to confirm specificity, BSA containing AGEs derived from glucose (Glu-AGEs-BSA), BSA containing AGEs derived from glycolaldehyde (Glycol-AGEs-BSA), BSA containing AGEs derived from methylglyoxal (MGO-AGEs-BSA), BSA containing AGEs derived from glyoxal (GO-AGEs-BSA), BSA containing $N^\varepsilon$-carboxymethyllysine (CML-BSA), BSA containing $N^\varepsilon$-carboxyethyllysine (CEL-BSA), and bovine serum albumin (BSA) were added at 50 μL/well to the antigen-immobilized plate in the same way as above, and the POD-labeled SJ-5 antibody (50 μL) was further added thereto, and stirred with a plate mixer, and then left standing at room temperature for 1 hour. After washing, an o-phenylenediamine solution (100 μL) prepared into 0.5 mg/mL with a 0.1 M citrate-phosphate buffer solution (pH 5.0) containing 0.02% (w/v) hydrogen peroxide was added to each well and left standing at 25° C. for 10 minutes. Then, color reaction was terminated by the addition of a 1 M sulfuric acid solution (50 μL) to each well. Then, absorbance at 490 nm was measured with a microplate reader.

Figure 4:
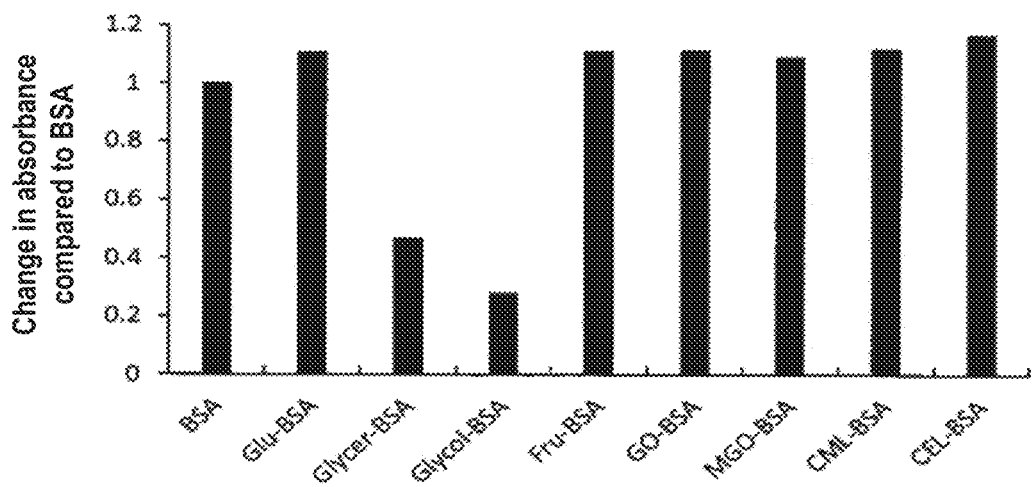
FIG. 4 is a diagram showing results of a specificity confirmation test of SJ-5 by competitive ELISA when GAL13-BSA was used as an immobilized antigen.
Figure 5:
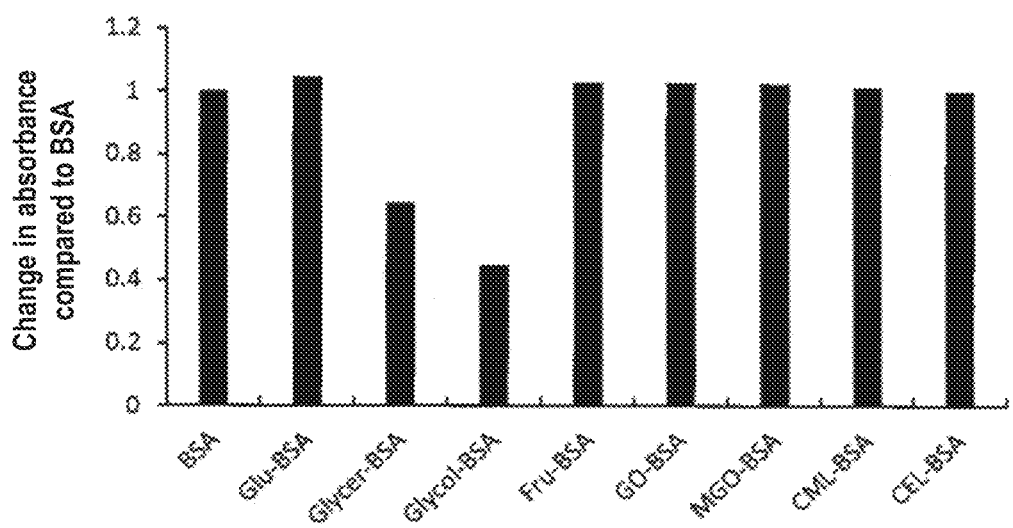
FIG. 5 is a diagram showing results of a specificity confirmation test of the SJ-5 antibody by competitive ELISA when Glycer-AGEs-BSA was used as an immobilized antigen.

FIG. 4 shows the results about the specificity of the POD-labeled SJ-5 antibody when GAL13-BSA was used as an immobilized antigen. FIG. 5 shows absorbance relative to that of control BSA defined as 1 as the results about the specificity of the POD-labeled novel monoclonal antibody SJ-5 when Glycer-AGEs-BSA was used as an immobilized antigen.

When GAL13-BSA and Glycer-AGEs-BSA were immobilized, the novel monoclonal antibody SJ-5 was also positive to Glycer-AGEs-BSA and Glycol-AGEs-BSA and negative to Glu-AGEs-BSA, Fru-AGEs-BSA, MGO-AGEs-BSA, GO-AGEs-BSA, CML-BSA, and CEL-BSA in terms of specificity.

[Example 8] Dissociation Constant Measurement of Monoclonal Antibody

The dissociation constant ($K_d$ value) of the monoclonal antibody SJ-5 was measured by the following approach: BSA containing AGEs derived from glyceraldehyde (Glycer-AGEs-BSA) was diluted with a 10 mM sodium acetate solution (pH 4.0) to prepare a ligand solution with a final concentration of 100 μg/mL. Biacore T200 (GE Healthcare Japan Corp.) was used for the immobilization of the ligand and the calculation of the KD value. The ligand solution was immobilized onto sensor chip CM5 (GE Healthcare Japan Corp.) using an amine coupling kit (GE Healthcare Japan Corp.). Subsequently, antibody dilution solutions containing the monoclonal antibody diluted into concentrations from 0 to 400 nM were prepared, and the $K_d$ value was calculated.

As a result, the $K_d$ value of the monoclonal antibody was 57.4 nM. BSA chemically bonded to the peak obtained in fractionation by HPLC (GAL13-BSA) was diluted with a 10 mM sodium acetate solution (pH 5.0) to prepare a ligand solution with a final concentration of 25 μg/mL. The $K_d$ value of the monoclonal antibody was calculated in the same way as above and was consequently 87.5 nM.

[Example 9] Mass Spectrometry of GAL13

The solvent used in mass spectrometry was a solvent of HPLC grade of FUJIFILM Wako Pure Chemical Corp. The dry powder of GAL13 prepared in Example 2 was dissolved in a 0.1% TFA solution containing 50% acetonitrile to adjust the final concentration to 0.25 mg/mL. α-Cyano-4-hydroxycinnamic acid (CHCA) was purchased as a matrix from Shimadzu GLC Ltd. and prepared into a 10 mg/mL solution with a 0.1% TFA solution containing 50% acetonitrile. The sample solution and the matrix solution were mixed in equal amounts in 0.6 mL Eppendorf Safe-Lock Tubes (Eppendorf AG), then added dropwise at 1 L/well to a plate for measurement, and dried in air. A mixed solution of des-Arg$^1$-

Figure 8:
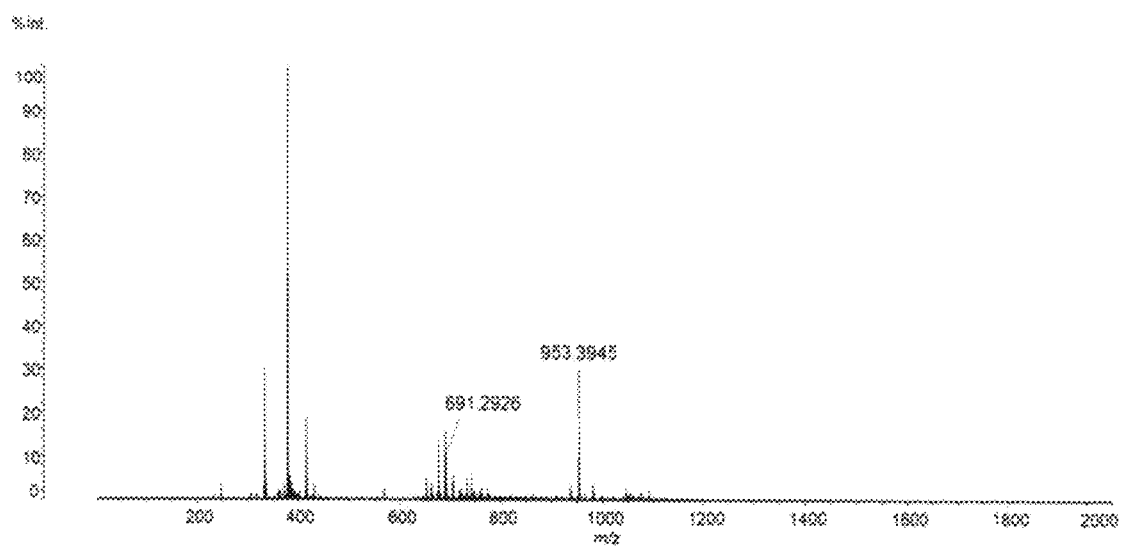
FIG. 8 is a chart showing results of mass spectrometry of GAL13.

Bradykinin, Angiotensin I, Glu[1]-Fibrinopeptide (AB Sciex Pte. Ltd.) as a peptide for mass calibration with a matrix was prepared and added dropwise to the plate in the same way as above. The plate thus dried in air was inserted to AXIMA Performance (Shimadzu Corp.), which is a matrix-assisted laser desorption/ionization time of flight mass spectrometer (MALDI-TOF-MS), and cation measurement was performed on the reflectron mode. The results of mass spectrometry are shown in FIG. 8.

As a result, peaks derived from the sample were observed at m/z=650 to 750 and 953. Particularly, m/z=691.2926 seemed to be from [M+Na] ion (theoretical value of monoisotopic mass: 691.2957, margin of error from the found value: 4.5 ppm), a Na adduct of $C_{34}H_{44}N_4O_{10}$. This almost agreed with the monoisotopic mass of a structure in which two Z-Lys-OH molecules were cross-linked by two DL-GLA molecules. Also, m/z=953.3945 seemed to be from [M+Na]$^+$ ion (theoretical value of monoisotopic mass: 953.4276, margin of error from the found value: 34.7 ppm), a Na adduct of $C_{48}H_2N_6O_{13}$. This almost agreed with the monoisotopic mass of a structure in which three Z-Lys-OH molecules were cross-linked by two DL-GLA molecules. From these results, GAL13 was shown to contain at least the following two types of compounds:

[Chemical Formula 25]

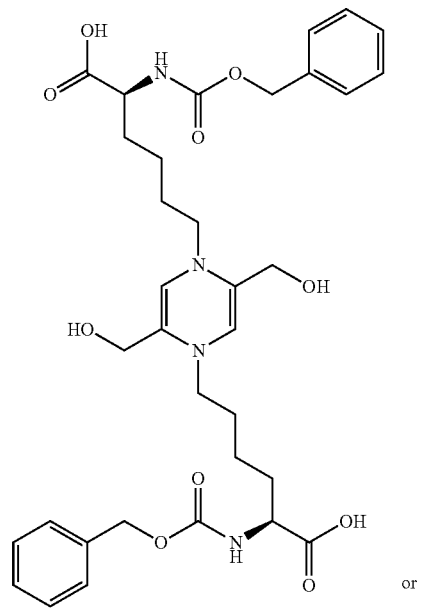

or

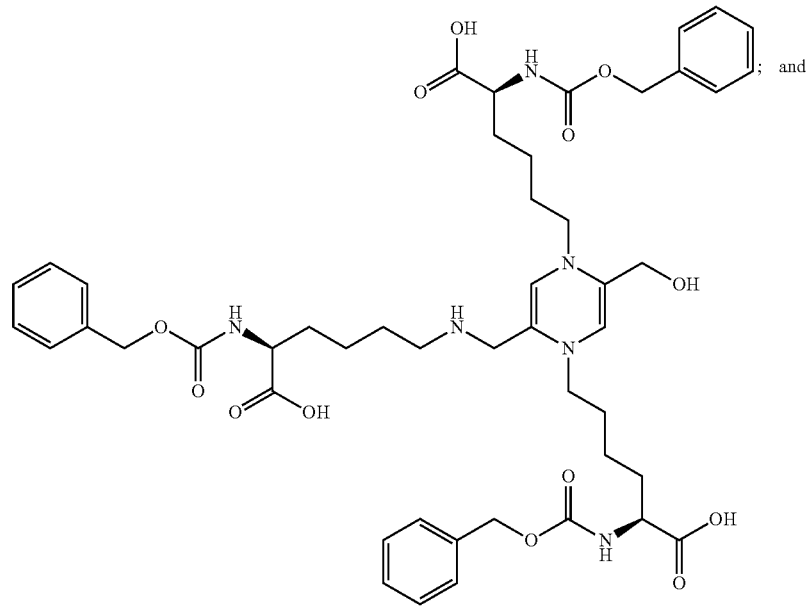

; and

-continued

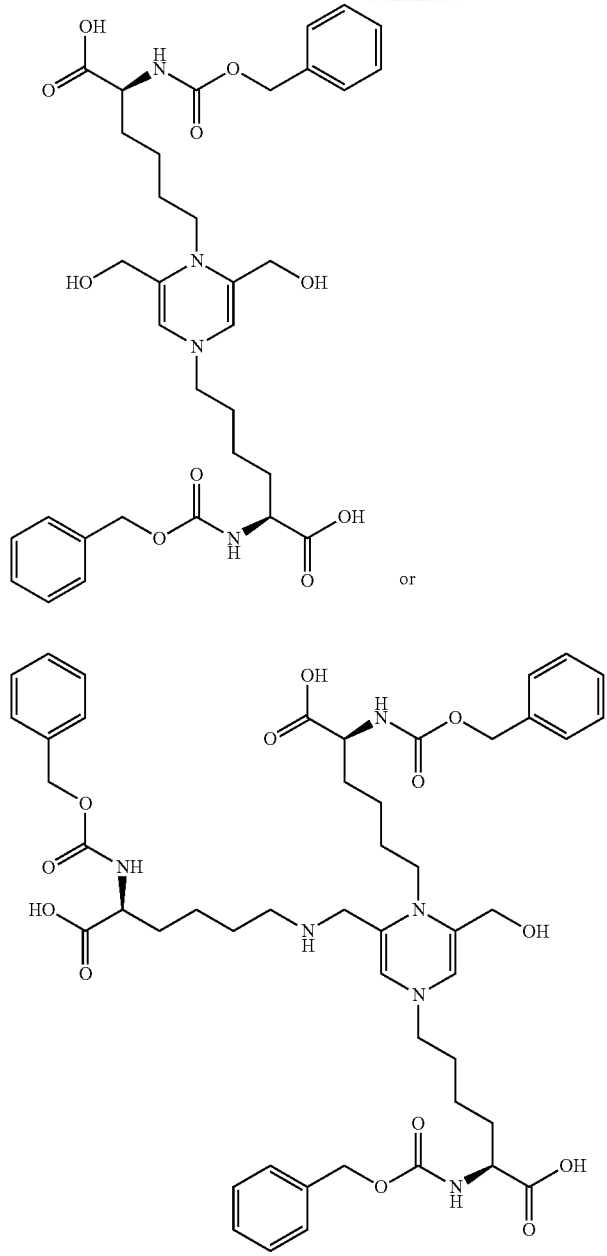 [SMILES: O=C(N[C@@H](CCCCN1C=C(CO)N(CCCC[C@H](NC(=O)OCc2ccccc2)C(=O)O)C(CO)=C1)C(=O)O)OCc1ccccc1 ; O=C(N[C@@H](CCCCNCC1=CN(CCCC[C@H](NC(=O)OCc2ccccc2)C(=O)O)C=C(CO)N1CCCC[C@H](NC(=O)OCc1ccccc1)C(=O)O)C(=O)O)OCc1ccccc1]

[Example 10] Radical Measurement of Peak Obtained in Fractionation by HPLC

The dry powder of GAL13 prepared in Example 2 was dissolved in a 0.2 M phosphate buffer solution (pH 7.4) to adjust the final concentration to 50 mg/mL. 50 μL of this solution was collected into a calibrated glass capillary micropipette (Drummond Scientific Company), and the lower end of the capillary tube was sealed with EM Meister Hematocrit Capillary Tube Sealing Wax Plate (AS ONE Corp.). Then, the capillary tube was transferred to a standard sample tube for electron spin resonance (ESR) apparatuses (outside diameter: 4 mm, Shigemi Co., Ltd.), which was then inserted to an ESR resonator. The ESR apparatus used was ELEXSYS-II E580 (Bruker Corp.), and measurement was performed at room temperature by the continuous wave method. The measurement conditions are as follows:

Field center 3350 G;
Field width 150 G;
Averaged scan 20;
Sampling time 0.03 s;
Field modulation amplitude 0.4 mT;
Field modulation Frequency 100 kHz;
Microwave power 3 mW;
Receiver gain 60.

Figure 9:
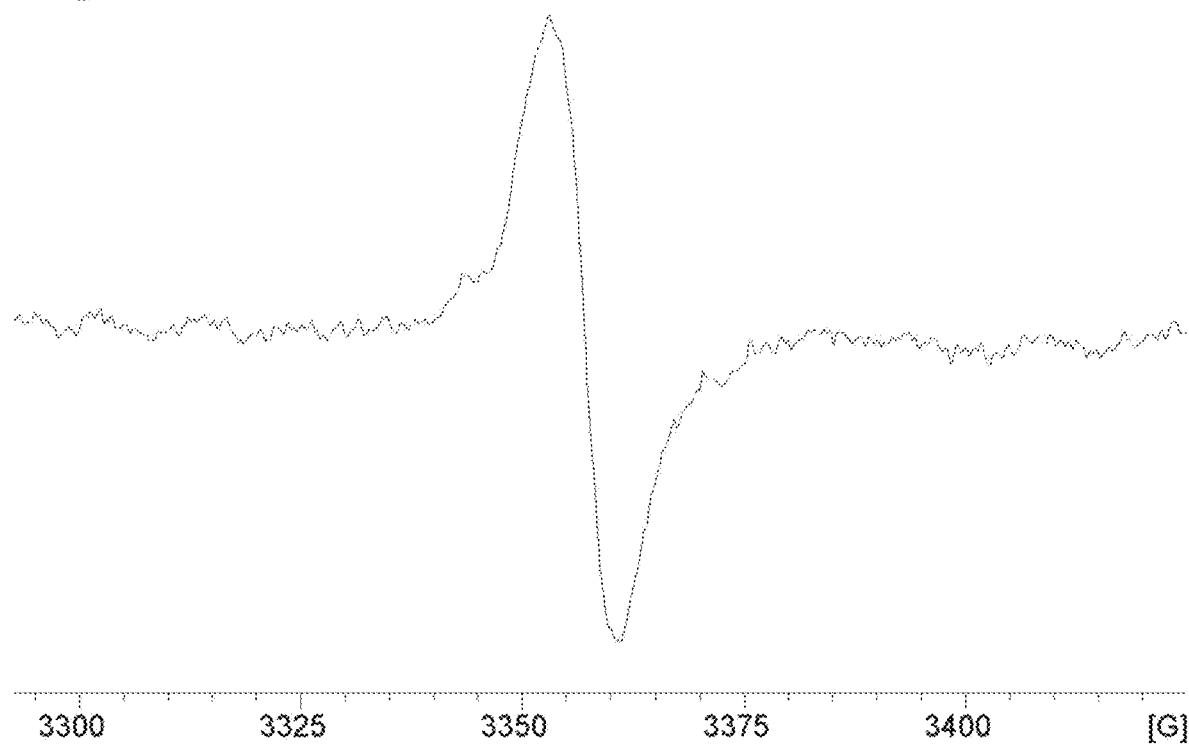
FIG. 9 is a diagram showing results of measuring electron spin resonance (ESR) as to GAL 13.

The results are shown in FIG. 9. From the g value (2.0043) and the line shape of the spectrum, the peak obtained in fractionation by HPLC was found to be AGEs derived from glyceraldehyde containing the carbon center generating radicals.

[Example 11] Oxidative Activity Evaluation of GAL13

(1) Preparation of 3,3'-Diaminobenzidine (DAB)

DAB was purchased from Dojindo Laboratories. DAB was weighed and dissolved in a Tris buffer solution (50 mM, pH 7.4) to adjust the final concentration to 5 mg/mL.

(2) Preparation of Sample Solution

The dry powder of GAL 13 prepared according to Example 2 was dissolved in a phosphate buffer solution (0.2 M, pH 7.4) to prepare a 2 mg/mL solution. A 2 mg/mL Z-Lys-OH solution was also prepared as a negative control group.

(3) Method for Evaluating Oxidative Activity

Figure 10:
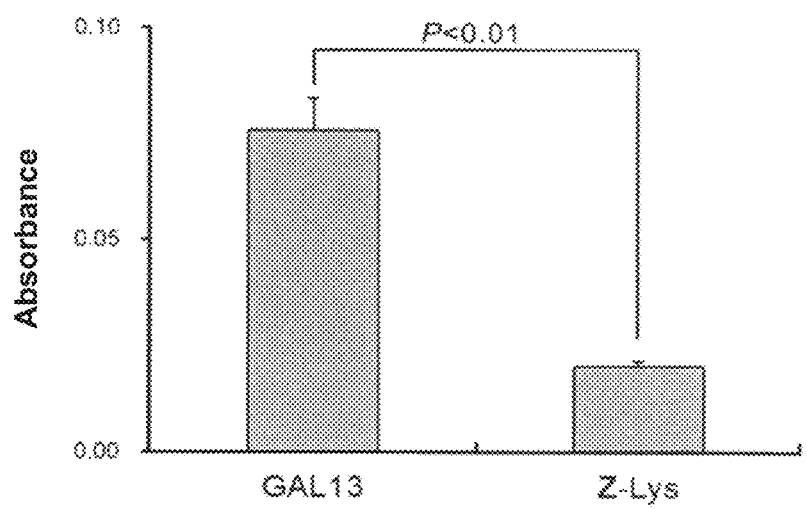
FIG. 10 is a graph showing results of a confirmation test of the oxidative activity of a sample containing GAL 13 using 3,3'-diaminobenzidine (DAB)

A 5 mg/mL DAB solution or a Tris buffer solution (50 mM, pH 7.4) was added at 10 µL/well to a 96-well plate (Violamo). Then, the sample solution was added at 90 µL/well and stirred with a plate mixer. The plate was incubated at 37° C. for 3 hours under light shielding, followed by the measurement of absorbance at 460 nm with Cytation 5 plate reader (BioTek Instrument Inc.). The oxidative activity against DAB was determined by subtracting the absorbance at 460 nm of the Tris buffer solution addition group from the absorbance at 460 nm of the DAB addition group. The results are shown in the graph of FIG. 10. A mean from 3 measurement values and standard deviation are shown. Student's t test was conducted with JMP 14.0 (SAS) for statistical analysis. The oxidative activity of GAL13 against DAB was found to be significantly higher than that of Z-Lys-OH ($P<0.01$).

[Example 12] Preparation of Pyridinium Compound Derived from Glyceraldehyde (GLAP)

GLAP can be prepared by the method known in the art (Usui et al., Biosci. Biotechnol. Biochem., 2003, 67 (4), 930-932). Specifically, GLAP was prepared by the following method.

(1) Preparation of GLAP Reaction Solution

N$^\alpha$-Acetyl-L-lysine (Ac-Lys-OH, Tokyo Chemical Industry Co., Ltd.) and DL-glyceraldehyde (DL-GLA, Nacalai Tesque, Inc.) were obtained by purchase.

DL-GLA (360.3 mg) was weighed and transferred to a 50 mL centrifugal tube. A phosphate buffer solution (0.2 M, pH 7.4, 20 mL) was added to the tube and stirred with a vortex mixer until DL-GLA was dissolved. Then, Ac-Lys-OH (376.5 mg) was added thereto and stirred until dissolved (concentration of DL-GLA in the solution: 200 mM, concentration of Ac-Lys-OH: 100 mM). The cap of the tube was hermetically sealed with a film such as Parafilm™ so as not to evaporate the liquid in the tube, followed by incubation at 37° C. for 1 week. The obtained reaction solution was stored at 4° C.

(2) Separation and Purification of GLAP

The GLAP reaction solution was filtered through a syringe filter (Millex-LG, Merck KGaA) with a pore size of 0.2 pm, and the filtrate was used as a sample for a liquid chromatograph-mass spectrometer (LC-MS). The LC part of LC/MS was composed of 1260 Infinity II system (Agilent Technologies, Inc.), and the MS part was composed of a quadrupole mass spectrometer (InfinityLab LC/MSD, G6125B, Agilent Technologies, Inc.). The LC part was composed of the following modules: a quaternary pump (G71111B), an isocratic pump (G7110B), a multisampler (G7167A), a multicolumn thermostat (G7116A), a diode array detector (G7115A), a fraction collector (G1364F), a MS flow modulator (G7170B), and OpenLAB CDS ChemStation software. Mobile phases of HPLC grade were purchased from FUJIFILM Wako Pure Chemical Corp. Mobile phase A was a 10 mM aqueous ammonium acetate solution containing 10 mL of a 1 M ammonium acetate solution mixed with 990 mL of distilled water, and mobile phase B was acetonitrile. The sample flowed in mobile phase A:B=99:1 at an analysis time from 0 to 7 minutes and in mobile phase A:B=10:90 at an analysis time from 7.1 to 12 minutes. The column used was ZORBAX SB-C18 (150×9.4 mm, Agilent Technologies, Inc.), and the flow rate was set to 4 mL/min. 80 µL of the sample solution thus filtered was injected to the LC-MS apparatus, and the peak of GLAP was detected with the diode array detector (215 nm and 254 nm) and MS (cation detection). A peak having UV absorptivity was observed at an analysis time of 5 minutes, and the peak contained a cation at m/z=297.1. Accordingly, the peak at the retention time of 5 minutes was recovered by MS fractionation with m/z=297 as a trigger. The solution thus fractionated was concentrated to dryness with a rotary evaporator (Tokyo Rikakikai Co., Ltd.). The obtained precipitates were stored at 4° C.

(3) Structure Confirmation of GLAP

The obtained precipitates (8 mg) were dissolved in heavy water (0.6 mL, FUJIFILM Wako Pure Chemical Corp.) and transferred to a sample tube for nuclear magnetic resonance (NMR) (Shigemi Co., Ltd.) with an outside diameter of 5 mm. Then, the structure of GLAP was confirmed in a NMR apparatus (AVANCE III HD, 500 MHz, CryoProbe mounted, Bruker Corp.). The total assignment of hydrogen and carbon was determined from $^1$H-NMR and $^{13}$C-NMR spectrum data. Also, $^1$H-$^1$H COSY, $^1$H-$^{13}$C HSQC, $^1$H-$^{13}$C HMBC, $^1$H-$^{15}$N HSQC, and $^1$H-$^{15}$N HMBC spectra were analyzed to confirm the validity of the assignment. The structure of GLAP is shown below.

[Chemical Formula 26]

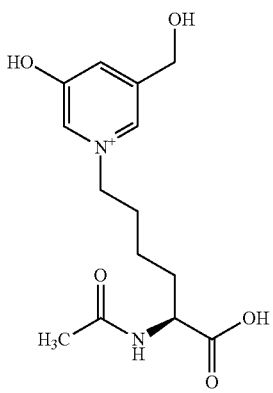

[Example 13] Evaluation of Reactivity of Novel Monoclonal Antibody with GLAP by Competitive ELISA (1) Reagent Preparation The following reagents were dissolved in RO water into 1 L and used as a coating solution.

Sodium carbonate (FUJIFILM Wako Pure Chemical Corp.) 1.59 g

Sodium bicarbonate (FUJIFILM Wako Pure Chemical Corp.) 2.93 g

BSA (5 g, Sigma-Aldrich Co. LLC) was dissolved in PBS (500 mL) and used as a blocking solution.

50 mM Tris (6.1 g, FUJIFILM Wako Pure Chemical Corp.) was dissolved in RO water (approximately 900 mL) and adjusted to pH 7.4 with 6 N hydrochloric acid (FUJIFILM Wako Pure Chemical Corp.). Glycerol (1 mL, Sigma-Aldrich Co. LLC) and Tween 20 (1 mL, Nacalai Tesque, Inc.) were added to the obtained solution and brought up to 1 L with RO water. The obtained solution was used as a diluting solution.

The following reagents were dissolved in RO water into 1 L, and 9 L of RO water was further added thereto, followed by the addition of Tween 20 (5 mL). The obtained solution was used as a washing solution.

Sodium chloride (FUJIFILM Wako Pure Chemical Corp.) 80 g

Potassium dihydrogen phosphate (FUJIFILM Wako Pure Chemical Corp.) 2 g

Disodium hydrogen phosphate dodecahydrate (FUJIFILM Wako Pure Chemical Corp.) 29 g (3) Immobilization of Antigen A solution of BSA containing AGEs derived from glyceraldehyde (stock solution: 10 mg/mL PBS solution) prepared into 1 μg/mL in a coating solution was added at 100 μL/well to a 96-well microtiter plate (COSTAR) and incubated overnight at 4° C.

(4) Blocking

Each well after the immobilization treatment was washed three times with a washing solution (300 μL), and a blocking solution (200 μL) was added thereto and left at room temperature for 1 hour.

(5) Competitive Experiment

GAL13 (prepared in Example 2), GLAP (prepared in Example 12), and Z-Lys-OH (Tokyo Chemical Industry Co., Ltd.) were each dissolved in a phosphate buffer solution (0.2 M, pH 7.4) to prepare a 20 mg/mL solution. Sample solutions of 2-fold dilution series from 0.0063 to 2 mg/mL (6 points) were further prepared by dilution with a diluting solution. A POD-labeled novel monoclonal antibody (SJ-5) solution was diluted 16,000-fold with a diluting solution containing BSA (1 mg/mL, FUJIFILM Wako Pure Chemical Corp.) to prepare a POD-labeled SJ-5 antibody dilution solution.

Each well treated with the blocking solution was washed three times with a washing solution (300 μL), and the sample solutions of 2-fold dilution series (50 μL each) and the POD-labeled SJ-5 antibody dilution solution (50 μL) were added thereto, stirred with a plate mixer for 2 minutes, and then incubated at 25° C. for 1 hour.

(6) Color Development

After washing three times with a washing solution (300 μL), a substrate solution (ELISA POD substrate TMB kit (Popular), Nacalai Tesque, Inc.) was added at 100 μL/well and incubated at room temperature for 10 minutes under light shielding. Then, color development was terminated by the addition of 2 N sulfuric acid (50 μL).

(7) Absorbance Measurement and Data Analysis

Absorbance was measured at a dominant wavelength of 450 nm and a sub-wavelength of 650 nm with a microplate reader (Cytation 5, BioTek Instrument Inc.), and the absorbance at the sub-wavelength was subtracted from the absorbance at the dominant wavelength. The results are shown in FIG. 11. The absorbance was reduced in a concentration-dependent manner for GAL13, whereas reduction in absorbance was observed for neither GLAP nor Z-Lys-OH. This demonstrated that the novel monoclonal antibody SJ-5 is an antibody that does not recognize GLAP, AGEs derived from glyceraldehyde known in the art.

[Example 14] Neutralization Test of Vascular Endothelial Cell Lumen Formation Inhibition of Glycer-AGEs-BSA Using SJ-5

(1) Preparation of Matrigel Matrix

Matrigel matrix (Corning Inc.) was placed in a refrigerator and thawed overnight. The thawed Matrigel matrix was added at 300 μL/well to a 12-well plate (Corning Inc.) and hardened by still standing at 37° C. for 1 hour in a $CO_2$ incubator (ESPEC Corp.).

(2) Preparation of Reaction Solution of Glycer-AGEs-BSA or Control BSA and Antibody 10 μL of Glycer-AGEs-BSA (10 mg/mL) prepared in Example 1 or 10 μL of control BSA (10 mg/mL), phosphate-buffered saline (PBS, FUJIFILM Wako Pure Chemical Corp.), and 90 μL of SJ-5 (10 mg/mL) or a control antibody (10 mg/mL) were added to a 1.5 mL tube (Watson) and left standing at room temperature for 10 minutes. Then, a supernatant was recovered by centrifugation at 14000 rpm for 15 minutes using a centrifuge (Thermo Fisher Scientific Inc.).

(3) Lumen Formation Test

HUVEC (human umbilical vein endothelial cells, National Institutes of Biomedical Innovation, Health and Nutrition, JCRB cell bank) was cultured in a 10 cm dish (Corning Inc.) using 10 mL of a medium for HUVEC (KAC Co., Ltd.).

The cultured HUVEC was washed with 10 mL of PBS. Then, 1 mL of trypsin-EDTA (FUJIFILM Wako Pure Chemical Corp.) was added thereto and left standing at room temperature for 3 minutes. HUVEC thus left standing was confirmed to be detached from the dish, and trypsin-EDTA was neutralized by the addition of 10 mL of a medium for HUVEC. After the neutralization, the whole amount was transferred to a 50 mL tube (Corning Inc.) and centrifuged at 1500 rpm for 3 minutes using a centrifuge (Kubota Corp.).

After the centrifugation, the supernatant was discarded, and precipitated cells were resuspended by the addition of 1 mL of a medium for HUVEC. A 10 μL aliquot from the resuspension was mixed with 10 μL of Trypan Blue (NanoEnTek Inc.), and 10 μL thereof was added to a counting chamber (NanoEnTek Inc.). Then, the number of live cells was counted in Auto Cell Counter EVE (NanoEnTek Inc.). The cell suspension was diluted into $2.5 \times 10^5$ cells/mL with a medium for HUVEC and inoculated at 400 μL/well to the Matrigel prepared in (1). After the inoculation, each reaction solution prepared in (2) was adjusted to 100 μg/mL with PBS, and the resulting solution was added at 100 μL/well, followed by culture for 8 hours in a $CO_2$ incubator.

Figure 13:
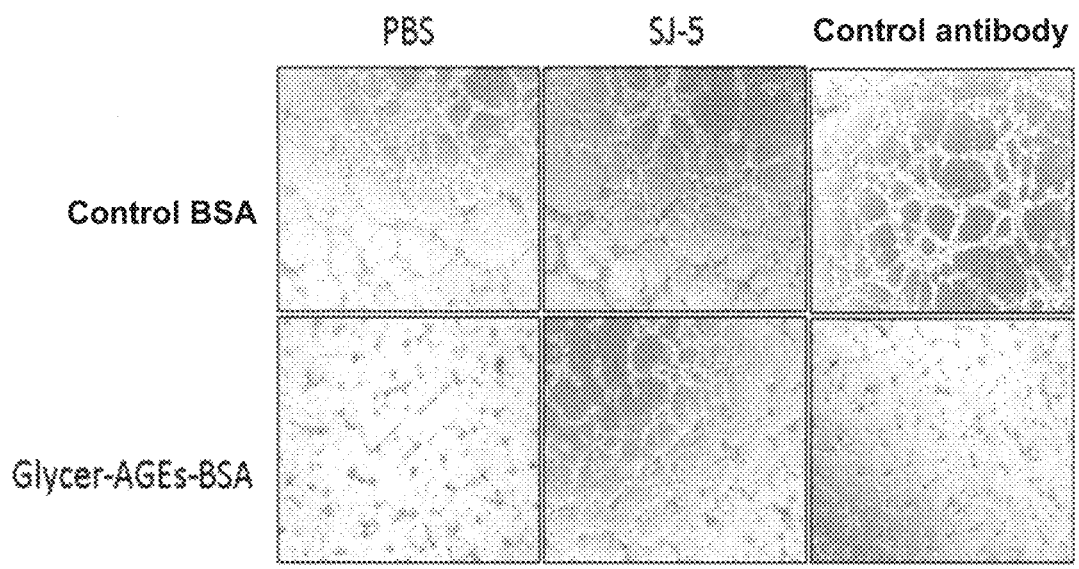
FIG. 13 is a photograph showing the morphology of HUVEC cultured for 8 hours in an endothelial cell lumen formation inhibition test in Example 14.

The morphology of HUVEC observed in the bright field using a 20× objective lens of BZ-X710 (Keyence Corp.) after the 8-hour culture is shown in FIG. 13. As shown in the drawing, HUVEC was confirmed to form a lumen in the SJ-5 antibody and control antibody reaction solution Matrigel matrix in the control BSA addition group. However, Glycer-AGEs-BSA inhibited lumen formation. Furthermore, this inhibition of lumen formation was neutralized by the reaction solution of the SJ-5 antibody, whereas the neutralization was not able to be confirmed for the control antibody. This result demonstrated that SJ-5 is capable of neutralizing the influence of Glycer-AGEs-BSA on HUVEC.

[Example 15] Endothelial-to-Mesenchymal Transition Inhibition Test of Glycer-AGEs-BSA Using SJ-5 Antibody (1) Matrigel Matrix was Prepared by the Same Operation as in Example 14.

(2) Preparation of Reaction Solution of Glycer-AGEs-BSA or Control BSA and Antibody 10 µL of Glycer-AGEs-BSA (10 mg/mL) prepared in Example 1, PBS, and 90 µL of SJ-5 (10 mg/mL) or a control antibody (10 mg/mL) were added to a 1.5 mL tube (Watson). Alternatively, 90 µL of a PBS solution of control BSA (10 mg/mL) was added. These solutions were left standing at room temperature for 10 minutes. Then, a supernatant was recovered by centrifugation at 14000 rpm for 15 minutes using a centrifuge (Thermo Fisher Scientific Inc.).

(3) Lumen Formation Inhibition Test

HUVEC was cultured in a 10 cm dish using 10 mL of a medium for HUVEC.

The cultured HUVEC was washed with 10 mL of PBS. Then, 1 mL of trypsin-EDTA was added thereto and left standing at room temperature for 3 minutes. HUVEC thus left standing was confirmed to be detached from the dish, and trypsin-EDTA was neutralized by the addition of 10 mL of a medium for HUVEC. After the neutralization, the whole amount was transferred to a 50 mL tube and centrifuged at 1500 rpm for 3 minutes using a centrifuge.

After the centrifugation, the supernatant was discarded, and precipitated cells were resuspended by the addition of 1 mL of a medium for HUVEC. A 10 µL aliquot from the resuspension was mixed with 10 µL of Trypan Blue, and 10 µL thereof was added to a counting chamber. Then, the number of live cells was counted in Auto Cell Counter EVE. The cell suspension was diluted into $2.5 \times 10^5$ cells/mL with a medium for HUVEC and inoculated at 400 µL/well to the Matrigel prepared in (1). After the inoculation, each reaction solution prepared in (2) was added at 100 µL/well, followed by culture for 8 hours in a $CO_2$ incubator.

(4) Recovery of Cell

Each well was washed three times with 1 mL of PBS, and Cell Recovery Solution (Corning Inc.) was added at 500 µL/well.

The cells and the Matrigel matrix were scraped off using Blue Chip (Watson), recovered into a 1.5 mL tube, and transferred to the 1.5 mL tube after rinsing of each well again with 500 µL of Cell Recovery Solution. The 1.5 mL tube was mixed by inversion five times and then left standing on ice for 1 hour to confirm that the Matrigel matrix was completely degraded. After the Matrigel matrix degradation, a supernatant was discarded by centrifugation at 800 rpm at 4° C. Precipitated cells were gently suspended in 1 mL of ice-cooled PBS and centrifuged at 800 rpm at 4° C. to discard a supernatant. Precipitated cells were gently suspended again in I mL of ice-cooled PBS and centrifuged at 800 rpm at 4° C.

(5) mRNA Recovery mRNA was recovered using CellAmp™ Direct RNA Prep Kit for RT-PCR (Takara Bio Inc.). Actual operation is shown below.

125 µL of Cell Amp Washing Buffer attached to the kit was added to the cells precipitated by centrifugation, and mixed. A supernatant was removed by centrifugation at 300×g for 5 minutes, and 49 µL of CellAmp Processing Buffer attached to the kit and 1 µL of DNase I for Direct RNA Prep were added to each tube. The resultant was left standing at room temperature for 5 minutes, then transferred to a PCR tube (Nippon Genetics Co., Ltd.), and left standing at 75° C. for 5 minutes using a thermal cycler (Nippon Genetics Co., Ltd.) to obtain mRNA.

(6) Reverse-Transcription Reaction

Reverse-transcription reaction was performed using PrimeScript™ RT Master Mix (Takara Bio Inc.). Actual operation is shown below. 1 µL of the mRNA obtained in (5), 2 µL of 5× PrimeScript RT Master Mix, and 7 µL of RNase Free $dH_2O$ attached to Master Mix were mixed in a PCR tube and reacted at 37° C. for 15 minutes and at 85° C. for 5 seconds using a thermal cycler.

(7) Real-Time PCR

Real-time PCR was performed using Luna Universal qPCR Master Mix (New England BioLabs Inc.). The reverse-transcription reaction product obtained in (6) was diluted with 90 µL of ultrapure water (Thermo Fisher Scientific Inc.). After the dilution, a reaction solution was prepared according to the composition shown below in the table, and added to a 384-well plate (Nippon Genetics Co., Ltd.).

TABLE 2

| | |
|---|---|
| Luna Universal qPCR Master Mix (Luna) | 5.5 µL |
| Forward primer (10 µM) | 0.5 µL |
| Reverse primer (10 µM) | 0.5 µL |
| Reverse-transcription reaction product | 4.5 µL |

The primers used were obtained from FASMAC Co., Ltd. commissioned to synthesize the following sequences.

Human α-SMA α-SMA
Forward:

CGGCTTTGCTGGGGACGAT

Reverse:

CAGGGGCAACACGAAGCTCAT

Human CD31
Forward:

ATTGCAGTGGTTATCATCGGAGTG

Reverse:

CTCGTTGTTGGAGTTCAGAAGTGG

Human β-Actin
Forward:

CTGGAACGGTGAAGGTGACA

Reverse:

AAGGGACTTCCTGTAACAATGCA

After the addition, real-time PCR was performed with QuantStudio™ 12K Flex real-time PCR system (Thermo Fisher Scientific Inc.) to quantify gene expression levels.

Figure 14:
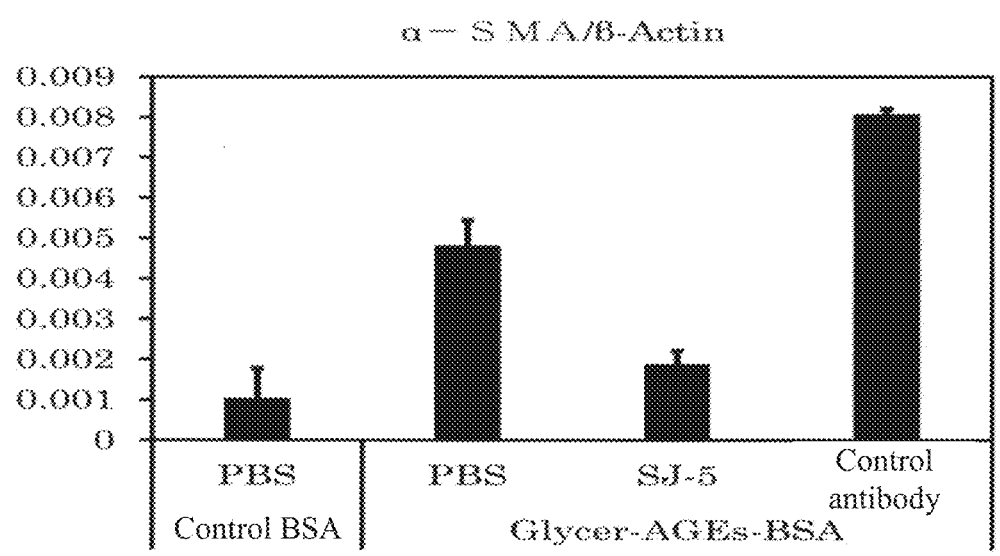
FIG. 14 is a graph showing the expression level of α-SMA in an endothelial-to-mesenchymal transition inhibition test of Glycer-AGEs-BSA using SJ-5 in Example 15.
Figure 15:
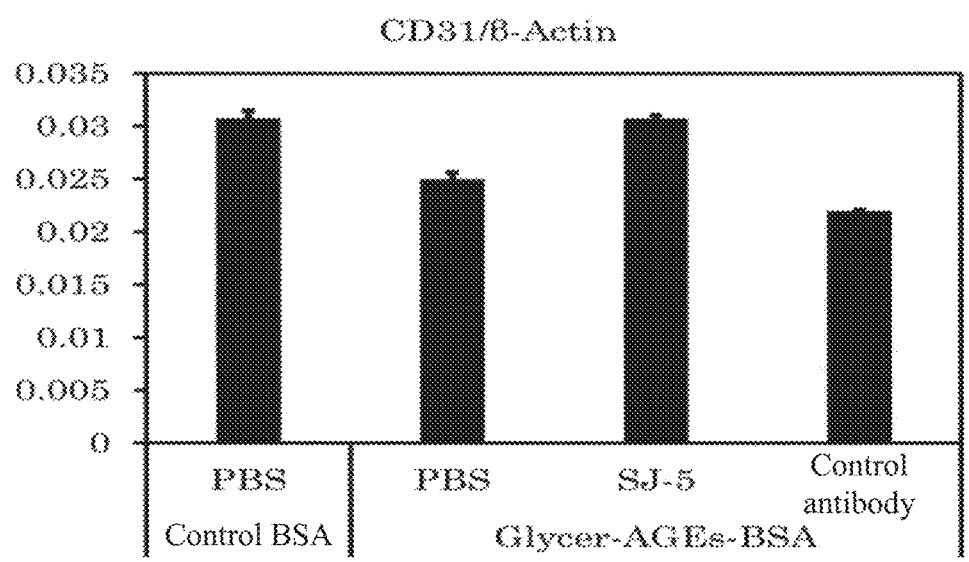
FIG. 15 is a graph showing the expression level of CD31 in an endothelial-to-mesenchymal transition inhibition test of Glycer-AGEs-BSA using SJ-5 in Example 15.

CD31 and α-smooth muscle actin (α-SMA) are known as markers for endothelial cells and mesenchymal cells, respectively (NPL 14, FIG. 2, etc.). Graphs of evaluating the expression levels of α-SMA and CD31 by calculation with the expression level of α-actin as an internal standard are shown in FIGS. 14 and 15. FIG. 14 demonstrated that the expression level of α-SMA is increased by the addition of Glycer-AGEs-BSA. This effect was suppressible by SJ-5, whereas the suppression was not found for the control antibody. As for CD31, FIG. 15 demonstrated that the expression level of CD31 was decreased by the addition of Glycer-AGEs-BSA. This effect was suppressible by SJ-5, whereas the suppression was not found for the control antibody. The increase in the expression level of α-SMA and the decrease in the expression level of CD31 are effects found in endothelial-to-mesenchymal transition, which causes the transformation of vascular endothelial cells to mesenchymal cells. From these results, it was confirmed that Glycer-AGEs-BSA has the effect of causing endothelial-to-mesenchymal transition, and SJ-5 is capable of suppressing this effect.

[Example 16] Preparative Purification (Higher Purity) of Glycer-AGEs-Z-Lys

Figure 16:
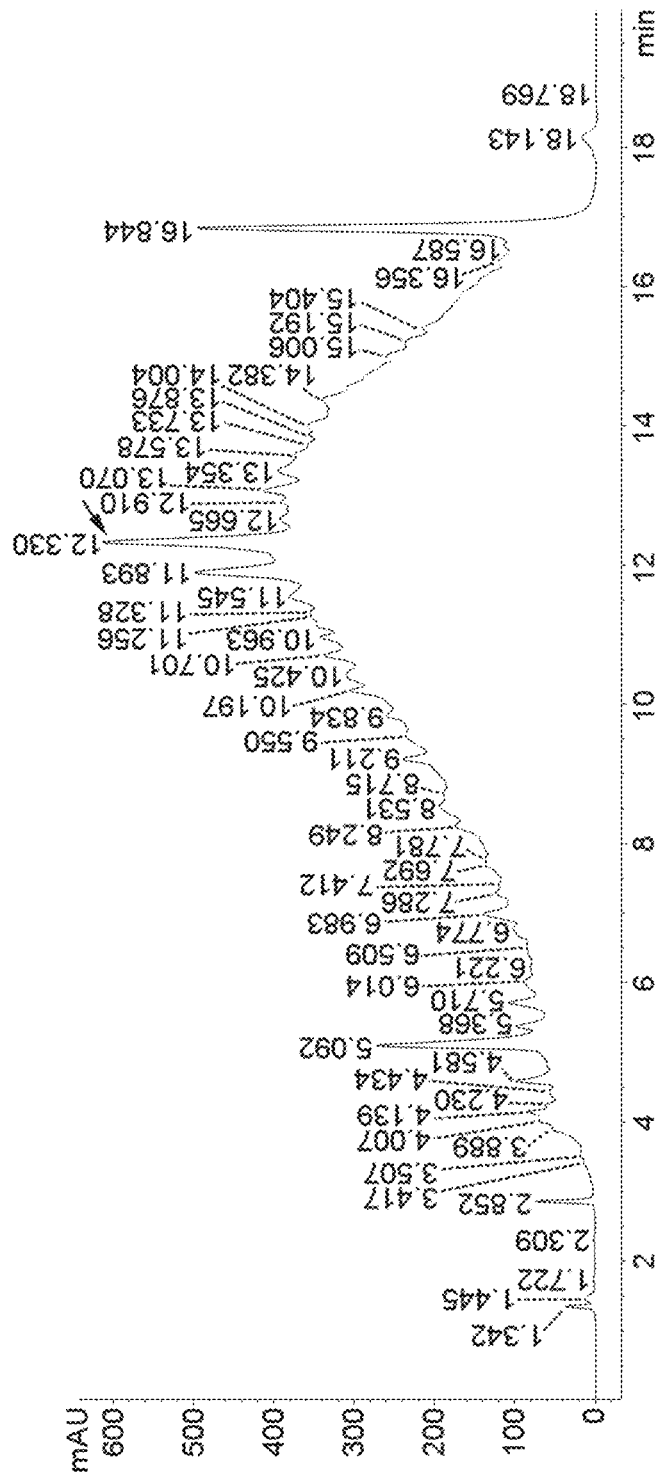
FIG. 16 shows results of LC/MS analysis of a reaction solution of Glycer-AGEs-Z-Lys prepared in Example 16 (diode array detection (260 nm)).
Figure 17:
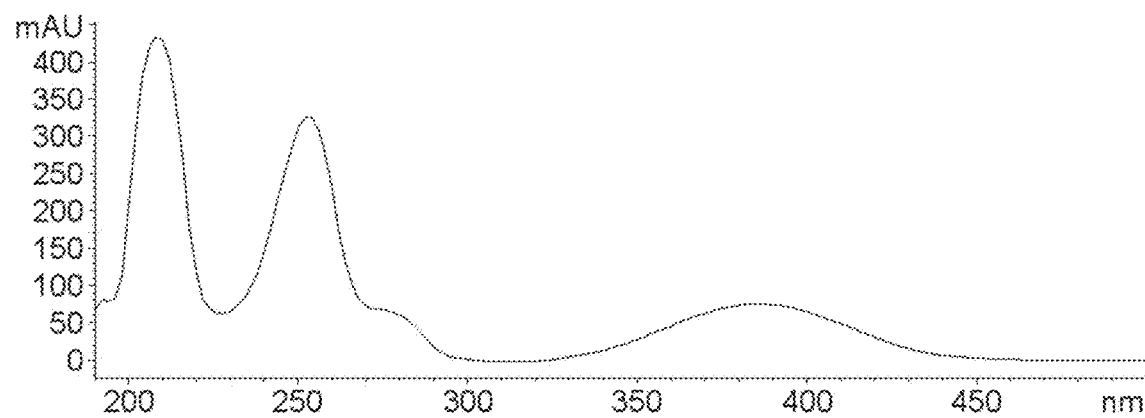
FIG. 17 shows the UV spectrum of Glycer-AGEs-Z-Lys prepared in Example 16 at the time of HPLC fractionation.
Figure 18:
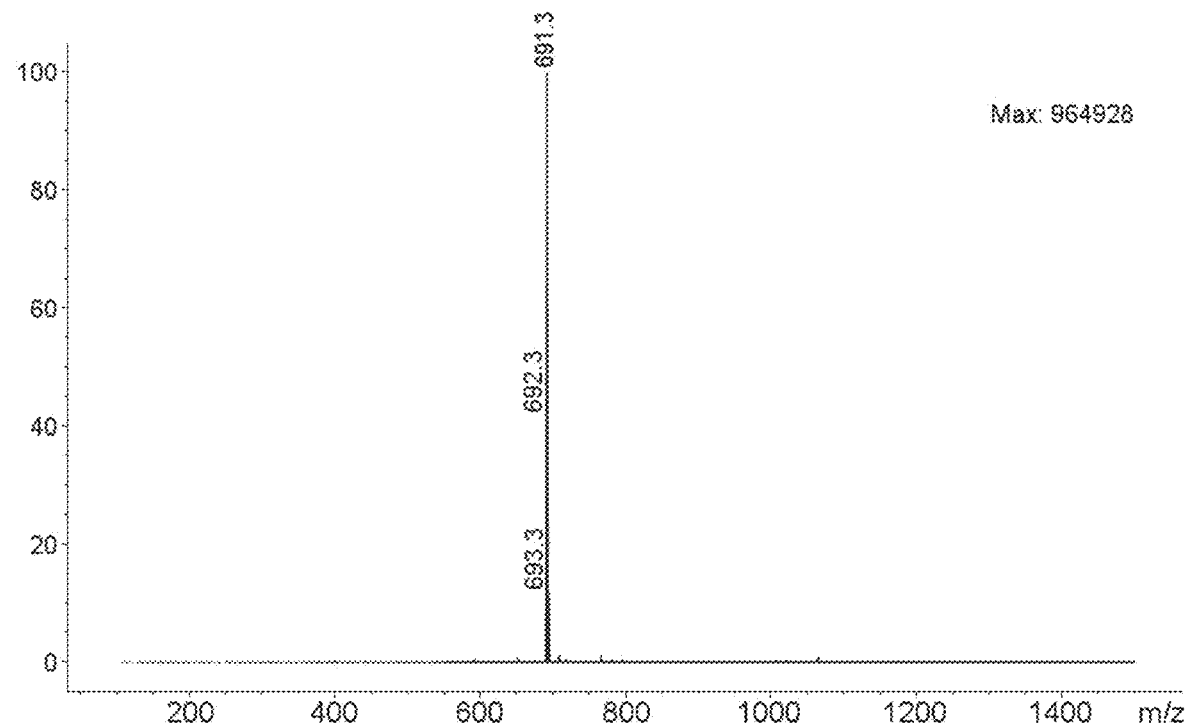
FIG. 18 shows the MS spectrum of Glycer-AGEs-Z-Lys prepared in Example 16 at the time of HPLC fractionation.

Glycer-AGEs-Z-Lys obtained as precipitates in Example 2 was dissolved in a 0.2 M phosphate buffer solution (pH 7.4) to prepare a 50 mg/mL sample solution. Then, filtration was performed through a syringe filter (Millex-LG, Merck KGaA) with a pore size of 0.2 pm, and the filtrate was used as a sample for a liquid chromatograph-mass spectrometer (LC/MS). The LC and MS parts of LC/MS were composed in the same way as in Example 12. Mobile phases of HPLC grade were purchased from FUJIFILM Wako Pure Chemical Corp. Mobile phase A was a 10 mM aqueous ammonium acetate solution containing 10 mL of a 1 M ammonium acetate solution mixed with 990 mL of distilled water, and mobile phase B was acetonitrile. The sample flowed in a concentration gradient of mobile phase A:B=100:0 to 85:15 at an analysis time from 0 to 2 minutes. The sample flowed in a concentration gradient of mobile phase A:B=85:15 to 70:30 at an analysis time from 2 to 15 minutes and of mobile phase A:B=70:30 to 10:90 at an analysis time from 15 to 17 minutes. The column used was ZORBAX SB-C18 (150×9.4 mm, Agilent Technologies, Inc.), and the flow rate was set to 4 mL/min. 50 μL of the sample solution thus filtered was injected to the LC-MS apparatus, and the peak of Glycer-AGEs-Z-Lys was detected with the diode array detector (260 nm) and MS (cation detection). A peak having UV absorptivity was observed at an analysis time of 12.3 minutes, and the peak contained [M+Na]$^+$ at m/z=691.3. Accordingly, the peak at the retention time of 12.3 minutes was recovered by MS fractionation with m/z=691 as a trigger. Hereinafter, this peak is designated as GAL691. The LC/MS analysis results are shown in FIG. 16 (diode array detection (260 nm)), FIG. 17 (UV spectrum), and FIG. 18 (MS spectrum).

Acetonitrile contained in the fractionation solution was removed with a rotary evaporator (Tokyo Rikakikai Co., Ltd.). 1 mL of a 10% aqueous TFA solution was added to 5 mL of the residue solution and mixed by inversion. Then, a supernatant was removed by centrifugation (12,000×g) at room temperature for 10 minutes. Ultrapure water (5 mL) was added to the obtained precipitates, which were then centrifuged again to remove a supernatant. This operation was carried out a total of three times to wash the precipitates. The precipitates were thus washed where dried in air, then measured as to dry weight (1 mg), and refrigerated.

[Example 17] Preparation of Pyridinium Compound Derived from Glyceraldehyde (Lys-Hydroxy-Triosidine)

Lys-hydroxy-triosidine can be prepared by the method known in the art (NPL 12). Specifically, Lys-hydroxy-triosidine was prepared by the following method.

(1) Preparation of Lys-Hydroxy-Triosidine Reaction Solution

Methanol (FUJIFILM Wako Pure Chemical Corp.), diethylenetriamine-N,N,N',N'',N''-pentaacetic acid (DTPA, Dojindo Laboratories), N''-acetyl-L-lysine (Ac-Lys-OH, Tokyo Chemical Industry Co., Ltd.), and DL-glyceraldehyde (DL-GLA, Nacalai Tesque, Inc.) were obtained by purchase.

A phosphate buffer solution (0.267 M, pH 10.5, 30 mL) and methanol (10 mL) were mixed (0.2 M phosphate buffer solution containing 25% methanol) in a 50 mL centrifugal tube. DTPA (15.7 mg) and DL-GLA (356.7 mg) were added to 36 mL of the solution described above, and dissolved with a vortex mixer. Then, Ac-Lys-OH (799.6 mg) was added thereto and stirred until dissolved (concentration of DTPA in the solution: 1 mM, concentration of DL-GLA: 110 mM, concentration of Ac-Lys-OH: 118 mM). Further, the cap of the tube was hermetically sealed with a film such as Parafilm™ so as not to evaporate the liquid in the tube, followed by incubation at 37° C. for 9 days. 260 mg and 196 mg of DL-GLA were further added to the reaction solution on days 3 and 6, respectively, and dissolved. The obtained reaction solution was stored at 4° C.

(2) Separation and Purification of Lys-Hydroxy-Triosidine

The Lys-hydroxy-triosidine reaction solution was filtered through a syringe filter (Millex-LG, Merck KGaA) with a pore size of 0.2 μm, and the filtrate was used as a sample for a liquid chromatograph-mass spectrometer (LC/MS). The LC and MS parts of LC/MS were composed in the same way as in Example 12. Mobile phases of HPLC grade were purchased from FUJIFILM Wako Pure Chemical Corp. Mobile phase A was a 10 mM aqueous ammonium acetate solution containing 10 mL of a 1 M ammonium acetate solution mixed with 990 mL of distilled water, and mobile phase B was acetonitrile. The sample flowed in a concentration gradient of mobile phase A:B=97:3 to 95:5 at an analysis time from 0 to 8 minutes. The sample flowed in a concentration gradient of mobile phase A:B=95:5 to 10:90 at an analysis time from 8 to 10 minutes and in mobile phase A:B=10:90 at an analysis time from 10 to 13 minutes. The column used was ZORBAX SB-C18 (150×9.4 mm, Agilent Technologies, Inc.), and the flow rate was set to 4 mL/min. 50 μL of the sample solution thus filtered was injected to the LC-MS apparatus, and the peak of Lys-hydroxy-triosidine was detected with the diode array detector (269 nm) and MS (cation detection). A peak having UV absorptivity was observed at an analysis time of 5.7 minutes, and the peak contained a cation at m/z=467.3. Accordingly, the peak at the retention time of 5.7 minutes was recovered by MS fractionation with m/z=467 as a trigger. The solution thus fractionated was concentrated to dryness with a rotary evaporator (Tokyo Rikakikai Co., Ltd.). The obtained precipitates were stored at −20° C.

(3) Structure Confirmation of Lys-Hydroxy-Triosidine

The obtained precipitates (10 mg) were dissolved in heavy water (0.6 mL, FUJIFILM Wako Pure Chemical Corp.) and transferred to a sample tube for nuclear magnetic resonance (NMR) (Shigemi Co., Ltd.) with an outside diameter of 5 mm. Then, the structure of Lys-hydroxy-triosidine was confirmed in a NMR apparatus (AVANCE III HD, 500 MHz, CryoProbe mounted, Bruker Corp.). The total assignment of hydrogen and carbon was determined from $^1$H-NMR and $^{13}$C-NMR spectrum data. Also, $^1$H-$^1$H COSY, $^1$H-$^{13}$C HSQC, and $^1$H-$^{13}$C HMBC spectra were analyzed to confirm the validity of the assignment. The structure of Lys-hydroxy-triosidine is shown below.

[Chemical Formula 27]

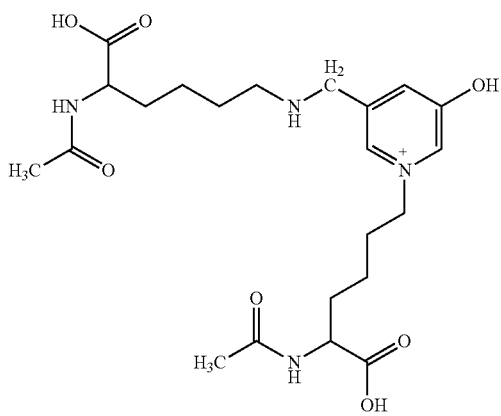

[Example 18] Evaluation of Reactivity of Novel Monoclonal Antibody with GAL691 and Lys-Hydroxy-Triosidine by Competitive ELISA (1) Reagent Preparation The following reagents were dissolved in RO water into 1 L and used as a coating solution.

Sodium carbonate (FUJIFILM Wako Pure Chemical Corp.) 1.59 g

Sodium bicarbonate (FUJIFILM Wako Pure Chemical Corp.) 2.93 g

BSA (5 g, Sigma-Aldrich Co. LLC) was dissolved in PBS (500 mL) and used as a blocking solution.

50 mM Tris (6.1 g, FUJIFILM Wako Pure Chemical Corp.) was dissolved in RO water (approximately 900 mL) and adjusted to pH 7.4 with 6 N hydrochloric acid (FUJIFILM Wako Pure Chemical Corp.). Glycerol (1 mL, Sigma-Aldrich Co. LLC) and Tween 20 (1 mL, Nacalai Tesque, Inc.) were added to the obtained solution and brought up to 1 L with RO water. The obtained solution was used as a diluting solution.

The following reagents were dissolved in RO water into 1 L, and 9 L of RO water was further added thereto, followed by the addition of Tween 20 (5 mL). The obtained solution was used as a washing solution.

Sodium chloride (FUJIFILM Wako Pure Chemical Corp.) 80 g

Potassium dihydrogen phosphate (FUJIFILM Wako Pure Chemical Corp.) 2 g

Disodium hydrogen phosphate dodecahydrate (FUJIFILM Wako Pure Chemical Corp.) 29 g (2) Immobilization of Antigen A solution of BSA containing AGEs derived from glyceraldehyde (stock solution: 10 mg/mL PBS solution) prepared into 1 µg/mL in a coating solution was added at 100 µL/well to a 96-well microtiter plate (COSTAR) and incubated overnight at 4° C.

(3) Blocking

Each well after the immobilization treatment was washed three times with a washing solution (300 µL), and a blocking solution (200 µL) was added thereto and left at room temperature for 1 hour.

(4) Competitive Experiment

GAL691 (prepared in Example 16) and Lys-hydroxy-triosidine (prepared in Example 17) were each dissolved in a phosphate buffer solution (0.2 M, pH 7.4) to prepare a 10 mg/mL solution. Sample solutions of 2-fold dilution series from 0.625 to 10 mg/mL (5 points) were further prepared by dilution with a diluting solution. Dilution solutions were also prepared from a blank solution containing no sample in the same way as above. A POD-labeled novel monoclonal antibody (SJ-5) solution was diluted 12,000-fold with a diluting solution containing BSA (1 mg/mL, FUJIFILM Wako Pure Chemical Corp.) to prepare a POD-labeled SJ-5 antibody dilution solution.

Each well treated with the blocking solution was washed three times with a washing solution (300 µL), and the sample solutions of 2-fold dilution series (50 µL each) and the POD-labeled SJ-5 antibody dilution solution (50 µL) were added thereto, stirred with a plate mixer for 2 minutes, and then incubated at 25° C. for 1 hour.

(5) Color Development

After washing three times with a washing solution (300 µL), a substrate solution (ELISA POD substrate TMB kit (Popular), Nacalai Tesque, Inc.) was added at 100 µL/well and incubated at room temperature for 10 minutes under light shielding. Then, color development was terminated by the addition of 2 N sulfuric acid (50 µL).

(6) Absorbance Measurement and Data Analysis

Figure 19:
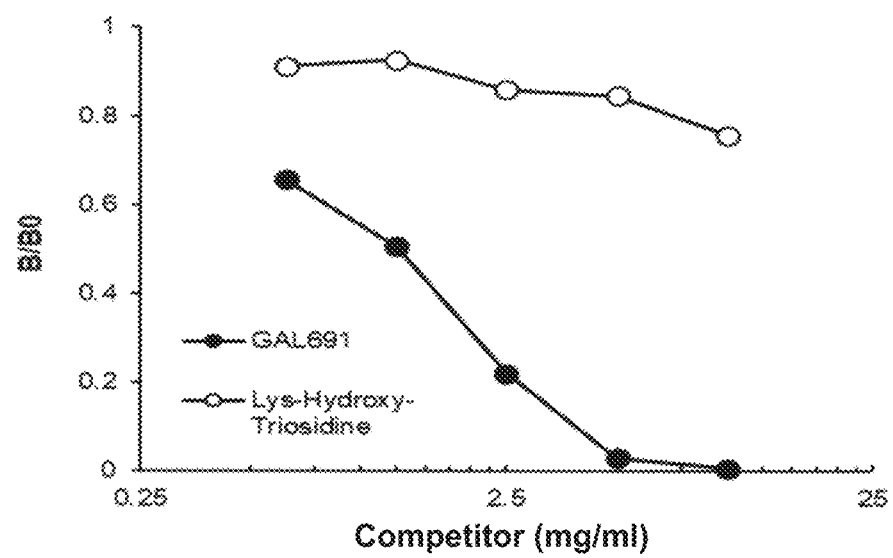
FIG. 19 is a graph showing results of reactivity evaluation of the novel monoclonal antibody with GAL691 and Lys-hydroxy-triosidine by competitive ELISA in Example 18.

Absorbance was measured at a dominant wavelength of 450 nm and a sub-wavelength of 650 nm with a microplate reader (Cytation 5, BioTek Instrument Inc.), and the absorbance at the sub-wavelength was subtracted from the absorbance at the dominant wavelength. Change in the absorbance of GAL691 and Lys-hydroxy-triosidine was indicated as relative values to the absorbance of the blank solution. The results are shown in FIG. 19. The absorbance was reduced in a concentration-dependent manner for GAL691, whereas no reduction in absorbance was observed for Lys-hydroxy-triosidine. This demonstrated that the novel monoclonal antibody SJ-5 is an antibody that binds to the novel structure of AGEs derived from glyceraldehyde and does not recognize Lys-hydroxy-triosidine, AGEs derived from glyceraldehyde known in the art.

[Example 19] Radical Measurement of GAL691 and Glycer-AGEs Known in the Art

GAL691 (10 mg/mL, PBS solution) prepared in Example 16 was analyzed for a radical by ESR. The measurement conditions of ESR are the same as those of Example 10 except for the following parameters:

Sampling time. 0.06 s;

Field modulation Amplitude. 0.2 mT; and

Microwave power. 15 mW.

The magnetic field was corrected with the g value (2.00264) of α,γ-bisdiphenylene-β-phenylallyl (BDPA).

Figure 20A:
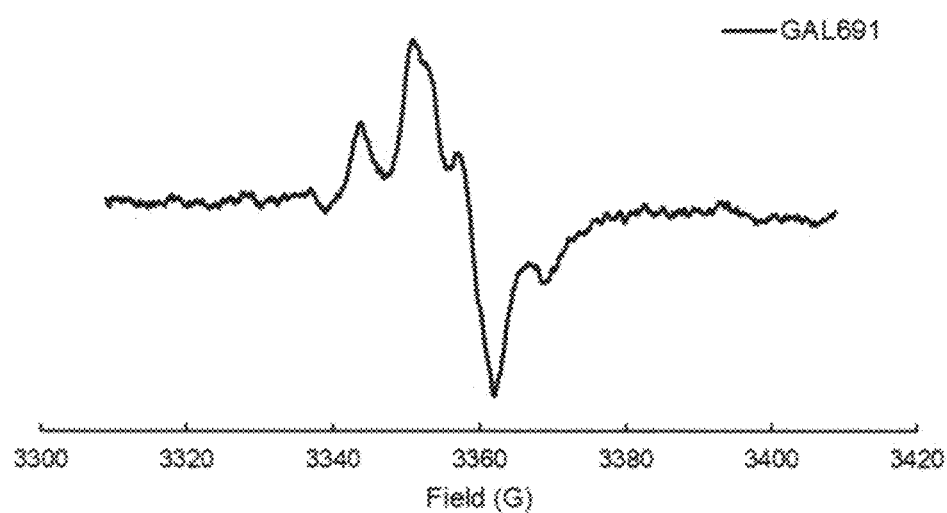
FIG. 20A is a diagram showing results of measuring the ESR spectrum of GAL691 in Example 19.
Figure 20B:
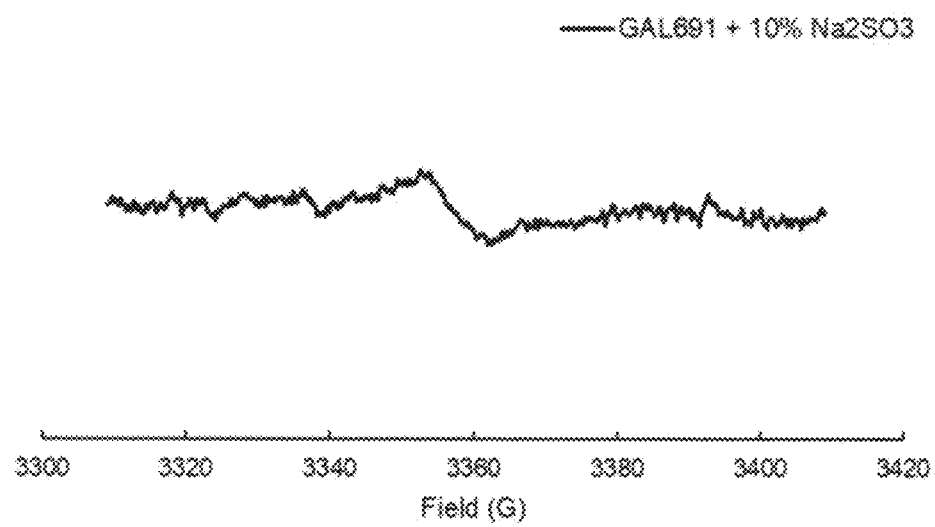
FIG. 20B is a diagram showing results of measuring the ESR spectrum of GAL691 to which sodium sulfite was added.
Figure 20C:
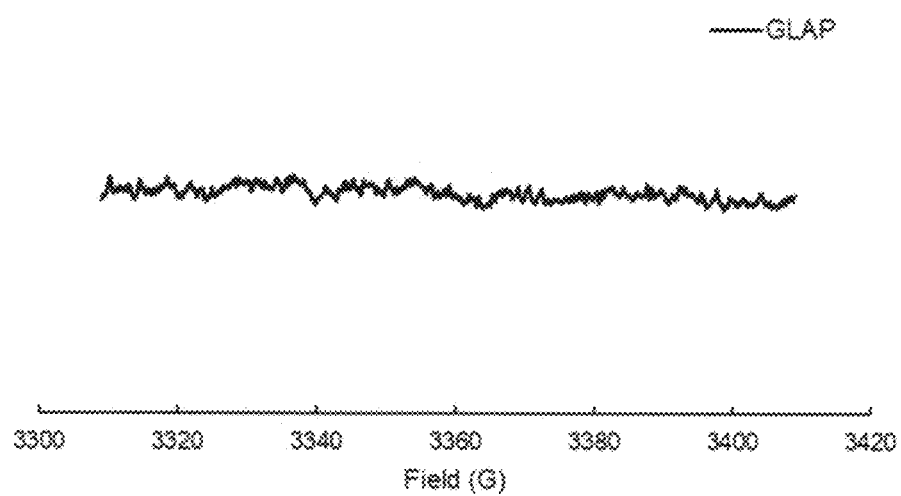
FIG. 20C is a diagram showing results of measuring the ESR spectrum of GLAP.
Figure 20D:
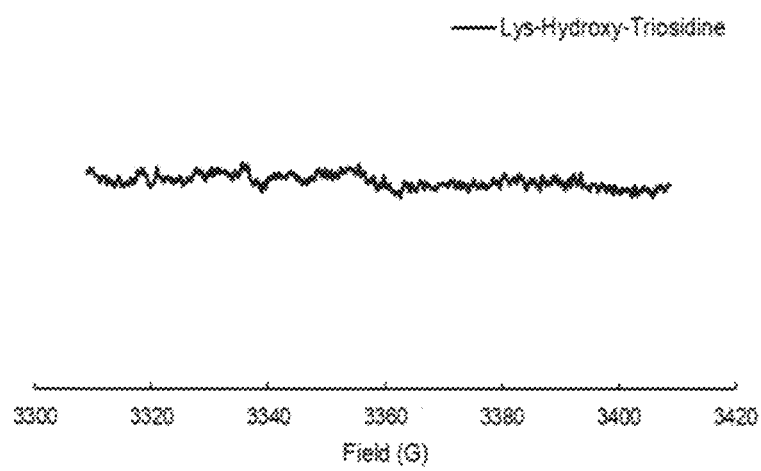
FIG. 20D is a diagram showing results of measuring the ESR spectrum of Lys-hydroxy-triosidine.

A signal showing an organic radical at g=2.00328 was detected for GAL691 from the ESR spectrum of FIG. 20A. This signal was largely attenuated by the addition of 10% (w/v) sodium sulfite ($Na_2SO_3$, FUJIFILM Wako Pure Chemical Corp.) (FIG. 20B). GLAP (Example 12) and Lys-hydroxy-triosidine (Example 17) (10 mg/mL each, PBS solution) were also subjected to ESR measurement in the same way as above. As a result, no signal derived from a radical was able to be detected (FIGS. 20C and 20D). From these results, GAL691 was confirmed to have radical properties that are not found in Glycer-AGEs known in the art.

[Example 20] Influence of Light Irradiation on Oxidative Activity of GAL691

AGEs are accumulated in tissues, such as the vitreous body, Bruch's membrane, and lens, of the eyes, and their involvement in various diseases including diabetic retinopathy and age-related macular degeneration has been pointed out (Yokoi et al., Br. J. Ophthalmol., 2005, 89, 673-675; Glenn et al., Invest. Ophthalmol. Vis. Sci., 2009, 50(1), 441-451, Nagaraj et al., Amino Acids, 201242, 1205-1220; Katagiri et al., Int. Ophthalmol., 2017, 38(2), 1-9; Kanda et al., Sci. Rep., 2017, 7, 16168). The eyes are an important organ that transmits information to the brain by converting light to electrical signals. Accordingly, the influence of light on the oxidative activity of GAL691 was studied, focusing on the relation of AGEs to light.

GAL691 prepared in Example 16 and Z-Lys (2 mg/mL each, PBS solution) were studied for their oxidative activity against DAB in the same way as in Example 11. In this respect, overnight reaction was performed under irradiation with white LED (3000 lux).

Figure 21:
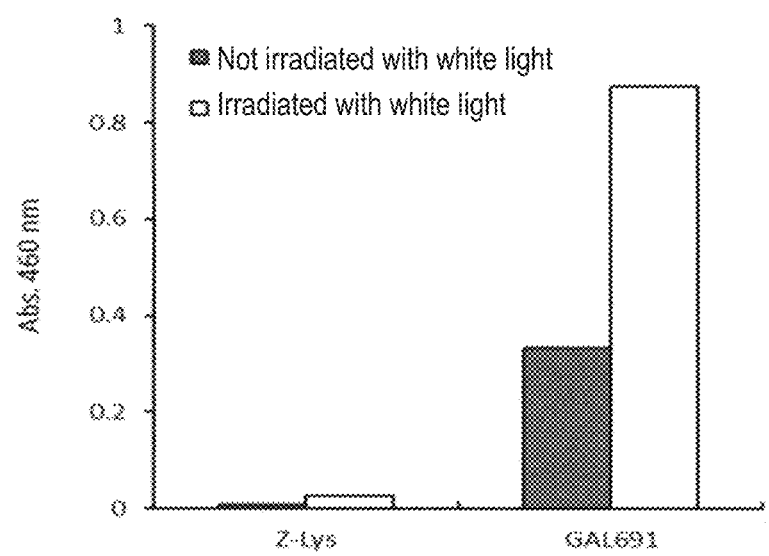
FIG. 21 is a graph showing results of a test for confirming the influence of white light irradiation on the oxidative activity of GAL691 against DAB.

As shown in FIG. 21, the oxidation product of DAB was increased by 2.6 times by treatment with GAL691 under light irradiation as compared with treatment with GAL691 alone (under light shielding). This demonstrated that the oxidative activity of GAL691 was further strengthened under light irradiation.

[Example 21] Formation of Singlet Oxygen Through Photosensitizing Effect of GAL691

GAL691 prepared in Example 16 was verified for its ability to form singlet oxygen through a photosensitizing effect. N-α,N-ε-Di(carbobenzoxy)-L-lysine (Z-Lys(Z)—OH) used as a control group for GAL691 was purchased from Watanabe Chemical Industries, Ltd.

25 µL of GAL691 or Z-Lys(Z)—OH (10 mM, PBS solution), 12.5 µL of 4-hydroxy-2,2,6,6-tetramethylpiperidine (4-OH-TEMP; Tokyo Chemical Industry Co., Ltd., 400 mM, PBS solution), and 12.5 µL of PBS were mixed in a 0.6 mL microtube (Watson) to prepare a reaction solution. 4-OH-TEMP changes into a nitroxide radical by capturing singlet oxygen and is therefore often utilized in the detection of singlet oxygen using ESR (Nakamura et al., J. Clin. Biochem. Nutr., 2011, 49 (2), 87-95). The reaction solution was irradiated with light at UV 365 nm, blue 470 nm, green 530 nm, or red 630 nm for 1 hour using a portable LED light source (MeCan Imaging Inc.). Then, ESR measurement was performed using a portion (50 µL) of each reaction solution. The ESR measurement was carried out under the same conditions as in Example 10 except for some parameters. The changed measurement parameters are as follows:

Field center. 3354.47 G; Field width: 70 G; Sampling time: 0.06 s; Field modulation amplitude: 0.1 mT; and Microwave power: 15 mW.

In order to quantify the concentration of the formed nitroxide radical, the following analysis was conducted: the spectrum of the observed nitroxide radical was first simulated with SpinFit module in Xepr software (Bruker Corp.) to identify a radical species ($g=2.0058$, $I=1$, $A_N=17.05$ G). Then, the spin concentration (µM) of the simulated nitroxide radical was determined with SpinCount module.

Figure 22:
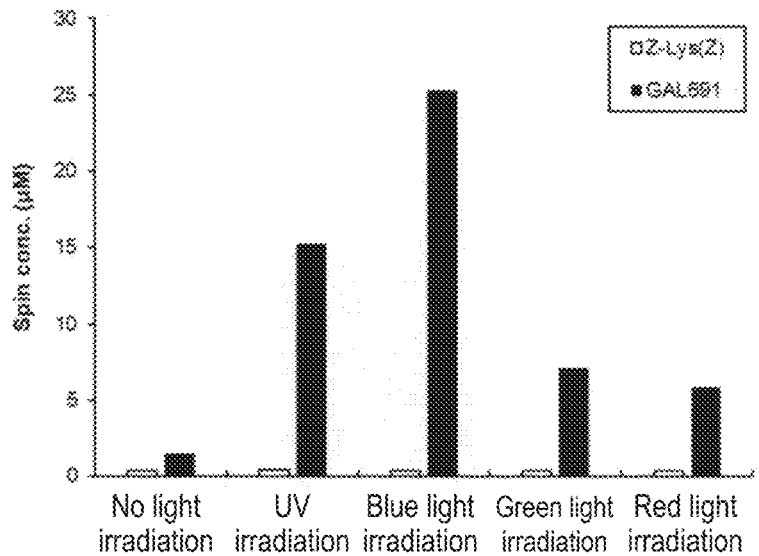
FIG. 22 is a graph showing results of a test for confirming the formation of singlet oxygen through the photosensitizing effect of GAL691 in Example 21.

As shown in FIG. 22, GAL691 was found to markedly form a nitroxide radical, particularly, by blue light irradiation. Thus, GAL691 was shown to be AGEs derived from glyceraldehyde that form singlet oxygen through a photosensitizing effect.

[Example 22] Comparison of Amount of Singlet Oxygen Formed Via Photosensitizing Effect Between GAL691 and Known AGEs Derived from Glyceraldehyde The amount of singlet oxygen formed under blue light irradiation was compared between GAL691 (Example 16) and GLAP (Example 12) or Lys-hydroxy-triosidine (Example 17). A method for preparing a sample, a light source, ESR analysis conditions, and ESR spectrum analysis conditions followed Example 21. In the measurement sample preparation, 12.5 µL (final concentration: 2.5 mM) of a singlet oxygen scavenger astaxanthin (FUJIFILM Wako Pure Chemical Corp.) was added instead of PBS to a prepared 10 mM dimethyl sulfoxide (DMSO, FUJIFILM Wako Pure Chemical Corp.) solution. 12.5 µL of DMSO was added instead of PBS to an astaxanthin-untreated sample.

Figure 23:
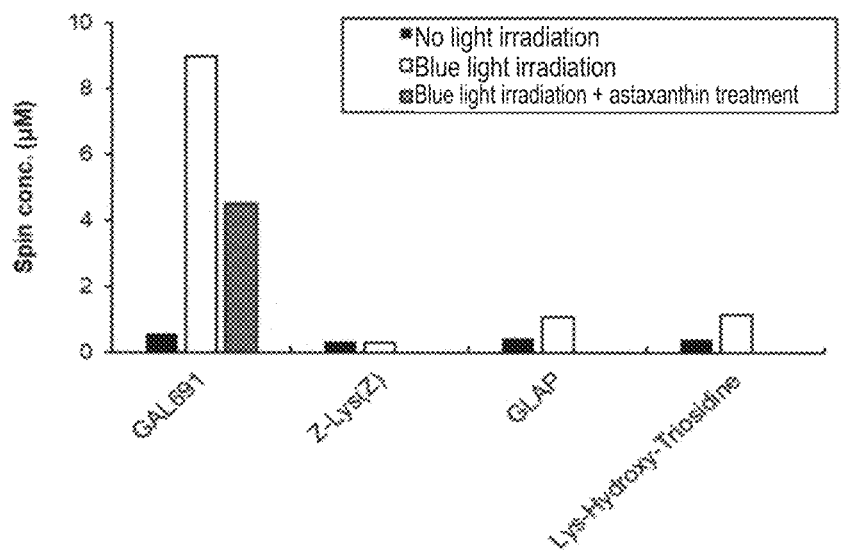
FIG. 23 is a graph showing results of a test for confirming the formation of singlet oxygen through the photosensitizing effect of GAL691 in Example 22.

The results are shown in FIG. 23. The amount of singlet oxygen formed by blue light irradiation was 9 times larger for GAL691 than for GLAP or Lys-hydroxy-triosidine. Also, singlet oxygen generated by GAL691 and light irradiation was captured by astaxanthin. Thus, GAL691 was shown to be novel AGE derived from glyceraldehyde that exhibits a strong photosensitizing effect as compared with AGEs derived from glyceraldehyde known in the art.

[Example 23] Study on Ability of GAL691 to Form Superoxide Anion

The amount of a superoxide anion formed under blue light irradiation was compared between GAL691 (Example 16) and GLAP (Example 12) or Lys-hydroxy-triosidine (Example 17). The formation of the superoxide anion was confirmed by measuring ESR using 1-hydroxy-4-phosphonooxy-2,2,6,6-tetramethylpiperidine (PPH). Specifically, since PPH that has captured the superoxide anion changes into stable nitrogen oxide, the radical concentration thereof was measured by ESR and evaluated as the amount of the superoxide anion (Dikalov et al., Biochemical and Biophysical Research Communications, 1998, 248, 211-215). PPH—HCl (Enzo Life Sciences, Inc.) was prepared into 10 mM in a PBS solution (pH 7.4). 25 µL each of GAL691, Z-Lys(Z), GLAP, and Lys-hydroxy-triosidine (10 mM, PBS solution) was added to a 0.6 mL microtube. Then, 12.5 µL of the PPH solution and 12.5 µL of PBS containing DTPA (0.4 mM) were added thereto to prepare a total of 50 µL of a reaction solution. Then, blue light irradiation was performed for 1 hour, followed by ESR measurement. A light source, ESR analysis conditions, and ESR spectrum analysis conditions were the same as in Example 21 except that microwave power was changed to 5 mW.

The results are shown in FIG. 24. GAL691 formed a superoxide anion in 4 times the amount by the other AGEs derived from glyceraldehyde without light irradiation (under light shielding). Furthermore, the amount formed was increased by approximately 3 times by blue light irradiation. Thus, it was shown that GAL691 is AGE derived from glyceraldehyde that forms a superoxide anion in a manner independent of light, and the amount formed is enhanced by light.

[Example 24] Preparation of Immunizing Antigen

Glycer-AGEs-Z-Lys obtained as precipitates in Example 2 was dissolved in a 0.2 M phosphate buffer solution (pH 7.4) to prepare a 50 mg/mL sample solution. Then, filtration was performed through a syringe filter (Millex-LG, Merck KGaA) with a pore size of 0.2 µm, and the filtrate was used as a sample for LC/MS. The analysis conditions of LC/MS were the same as in Example 16. A fraction containing the novel structure GAL691 at a retention time from 10 to 16 minutes was fractionated. Acetonitrile contained in the fractionation solution was removed with a rotary evaporator (Tokyo Rikakikai Co., Ltd.). A 10% aqueous TFA solution (1 mL) was added to the residue solution (5 mL) and mixed by inversion. Then, a supernatant was removed by centrifugation (12,000×g) at room temperature for 10 minutes. Ultrapure water (5 mL) was added to the obtained precipitates, which were then centrifuged again to remove a supernatant. This operation was carried out a total of three times to wash the precipitates. The precipitates were thus washed where dried in air, then measured as to dry weight, and refrigerated. 20 mg of precipitates was obtained per mL of the 50 mg/mL sample solution.

The precipitates thus dried were dissolved in a 0.2 M phosphate buffer solution (pH 7.4) to adjust the final concentration to 40 mg/mL (A-peak solution). This solution was further diluted 10-fold with phosphate-buffered saline (PBS, pH 7.4) to adjust the final concentration to 4 mg/mL. A solution of a carrier protein was prepared as follows: a freeze-dried powder of bovine serum albumin (BSA, Sigma-Aldrich Co. LLC) was dissolved in PBS to adjust the final concentration to 10 mg/mL. The 4 mg/mL A-peak solution (500 µL) and the 10 mg/mL BSA solution (200 µL) were mixed in 1.5 mL Eppendorf Safe-Lock Tubes (Eppendorf AG). Subsequently, 1-ethyl-3-(3-dimethylaminopropyl)carbodiimide hydrochloride (EDC, Thermo Fisher Scientific Inc.) was dissolved in ultrapure water to prepare a 10 mg/mL aqueous solution. A 10 mg/mL aqueous EDC solution (100 µL) was quickly added to the mixed solution of A-peak and BSA (700 µL), mixed by inversion, and then incubated overnight at room temperature.

After the completion of the reaction, the reaction solution was immediately subjected to gel filtration through Zeba Spin Desalting Columns (7K MWCO, Thermo Fisher Scientific Inc.). Dialysis was further performed at a low temperature (4° C.) using Slide-A-Lyzer MINI Dialysis Device (3.5K MWCO, Thermo Fisher Scientific Inc.). PBS was used as an external dialysis solution. Three hours after the start of the dialysis, the external solution was replaced, and dialysis was further performed overnight.

After the completion of the dialysis, the solution in the dialysis device was recovered and concentrated with Amicon Ultra-0.5 (30K MWCO, Merck KGaA). The protein concentration of BSA cross-linked with A-peak (A-peak-BSA) was determined with Pierce BCA Protein Assay Kit (Thermo Fisher Scientific Inc.) and adjusted to an arbitrary protein concentration with PBS. A-peak-BSA was used as an immunizing antigen for mouse monoclonal antibody preparation.

[Example 25] Preparation of Monoclonal Antibody (PB-1)

(1) Immunization of Mouse

A-peak-BSA (4 mg/mL) was mixed as an immunizing antigen with the same volume thereas of Adjuvant Complete Freund (Becton, Dickinson and Company) to prepare an emulsion (concentration of the antigen: 2 mg/mL), with which ten BALB/c mice were subcutaneously immunized at their backs for initial immunization (amount of the antigen: 200 µg/animal). Booster immunization (amount of the antigen. 50 µg/animal) was performed every 1 week using an emulsion (concentration of the antigen: 0.5 mg/mL) prepared by mixing A-peak-BSA (1 mg/mL) with the same volume thereas of Adjuvant Complete Freund (Becton, Dickinson and Company). After six shots from the initial immunization, blood was collected from the tail veins, and the antibody titers were confirmed. An antigen for booster immunization (amount of the antigen. 50 µg/animal) was intraperitoneally administered as a final shot to a mouse having a high antibody titer, and the spleen was excised for cell fusion 3 days later.

(2) Measurement of Antibody Titer

The titer of antiserum was evaluated by ELISA. The immunizing antigen A-peak-BSA was added at 50 µL/well with a concentration of 5 µg/mL to a 96-well microtiter plate (NUNC) and immobilized overnight at 4° C. The plate was washed three times with PBS containing 0.05% (v/v) Tween 20 (PBS-T) and then blocked with PBS-T containing 0.5% (w/v) gelatin for 1 hour. The antiserum was serially diluted into 5-fold dilutions from 500-fold to 1562500-fold to prepare dilution series, which were then added at 50 µL/well to the antigen-immobilized plate and left standing for 1 hour. After washing, a secondary antibody (horseradish peroxidase (HRP)-labeled anti-mouse IgG (Kirkegaard & Perry Laboratories, Inc.) diluted 10000-fold with PBS-T containing 0.1% gelatin was added at 50 µL/well and left standing for 1 hour. After washing, an o-phenylenediamine solution (100 µL) adjusted to 0.5 mg/mL with a 0.1 M citrate-phosphate buffer solution (pH 5.0) containing 0.02% (w/v) hydrogen peroxide was added to each well and left standing at 25° C. for 20 minutes. Then, color reaction was terminated by the addition of a 2 N sulfuric acid solution (50 µL) to each well. Then, absorbance at 490 nm was measured with a microplate reader. As a result, a mouse, 12500-fold or higher dilution solutions of the antiserum of which exhibited significant reactivity with the antigen was used for cell fusion.

(3) Preparation of Spleen Cell and Cell Fusion

The spleen excised from the mouse was ground to prepare approximately $1\times10^8$ spleen cells per animal. Myeloma cells P3U1 were cultured, and P3U1 having a live cell ratio of 95% or more on the day of cell fusion was prepared. The spleen cells and P3U1 were mixed at 5.1 (ratio of the number of cells) and subjected to cell fusion using polyethylene glycol with a molecular weight of 4000 and a concentration of 50% (w/v). The cells thus fused were washed with a medium and suspended in HAT medium, and the cells were seeded at $1\times10^5$ cells/well to the wells of a 96-well culture plate and cultured for hybridoma selection. On cell fusion day 10, the hybridoma culture supernatant was recovered, and an antibody titer in the culture supernatant was measured.

(4) Screening for Antibody Production-Positive Well

The culture supernatant on day 10 after the cell fusion was recovered and screened for an antibody production-positive well by the antibody titer measurement method described above. A clone positive to A-peak-BSA and KLH containing AGEs derived from glyceraldehyde (Glycer-AGEs-KLH) and negative to BSA was selected. A method for preparing Glycer-AGEs-KLH was shown in Example 27.

(5) Cloning

A clone having high specificity for A-peak-BSA was cloned by the limiting dilution method. Specifically, the cells were prepared into 10 cells/mL with RPMI medium containing 10% FBS and added at 200 µL/well to two 96-well culture plates. Ten days later, a clone was obtained which was confirmed to be positive to A-peak-BSA and Glycer-AGEs-KLH and negative to BSA in the culture supernatant and was derived from each well. Cells producing a novel monoclonal antibody PB-1 as the antibody of the present invention having sufficient specificity were obtained.

(6) Purification of Antibody

The cells producing the novel monoclonal antibody PB-1 were cultured in RPMI medium containing 10% FBS, then washed with PBS, and cultured in a serum-free medium (SMF medium, GIBCO) for 5 days to 7 days to obtain a culture supernatant. An IgG fraction was purified from the culture supernatant through Protein G column (GE Healthcare Japan Corp.) to obtain the novel monoclonal antibody PB-1 as the antibody of the present invention having sufficient specificity.

[Example 26] Dissociation Constant Measurement of Monoclonal Antibody PB-1

The dissociation constant (Kd value) of the monoclonal antibody PB-1 was measured by the following approach: A-peak-BSA was diluted with a 10 mM sodium acetate solution (pH 5.0) to prepare a ligand solution with a final concentration of 50 μg/mL. Biacore T200 (GE Healthcare Japan Corp.) was used for the immobilization of the ligand and the calculation of the KD value. The ligand solution was immobilized (final amount immobilized: 72 RU) onto sensor chip CM5 (GE Healthcare Japan Corp.) using an amine coupling kit (GE Healthcare Japan Corp.). Subsequently, PB-1 antibody dilution solutions from 0.1953 to 50 nM were prepared with a running buffer solution HBS-P+ (GE Healthcare Japan Corp.), and a sensorgram was obtained.

1:1 binding was adopted to a fitting model, and the sensorgram was analyzed. As a result, the Kd value of the PB-1 monoclonal antibody was 4.15 nM.

The amino acid sequences of variable regions determined by a routine method are shown in FIG. 25. CDR sequences are underlined.

[Example 27] Preparation of Keyhole Limpet Hemocyanin Containing AGEs Derived from Glyceraldehyde (Glycer-AGEs-KLH)

A method for preparing Glycer-AGEs-KLH followed the method for preparing Glycer-AGEs-BSA described in Example 1 except that 167 mg of keyhole limpet hemocyanin (KLH, FUJIFILM Wako Pure Chemical Corp.) was reacted instead of 500 mg of BSA with DL-glyceraldehyde (concentration of KLH in the solution: 8.3 mg/mL).

[Example 28] Preparation of Pyridinium Compound Derived from Glycolaldehyde (GA-Pyridine)

GA-pyridine can be prepared by the method known in the art (Murakami et al., Bioscience Biotechnology and Biochemistry, 2018, 82(2), 312-319). Specifically, GA-pyridine was prepared by the following method.

(1) Preparation of GA-Pyridine Reaction Solution $N^\alpha$-Acetyl-L-lysine (Ac-Lys-OH, Tokyo Chemical Industry Co., Ltd.) and a glycolaldehyde dimer (GA, Sigma-Aldrich Co. LLC) were obtained by purchase. 0.96 g of GA (0.2 M) was added to a 50 mL centrifugal tube and completely dissolved with 40 mL of a phosphate buffer solution (0.2 M, pH 7.4). Then, 0.75 g of Ac-Lys-OH (0.1 M) was added thereto and stirred until dissolved. The cap of the tube was hermetically sealed with a film such as Parafilm™ so as not to evaporate the liquid in the tube, followed by incubation at 50° C. for 3 days. The obtained reaction solution was stored at 4° C.

(2) Separation and Purification of GA-Pyridine

The GA-pyridine reaction solution was filtered through a syringe filter (Millex-LG, Merck KGaA) with a pore size of 0.2 μm, and the filtrate was used as a sample for a liquid chromatograph-mass spectrometer (LC/MS). The LC and MS parts of LC/MS were composed in the same way as in Example 12. Mobile phases of HPLC grade were purchased from FUJIFILM Wako Pure Chemical Corp. Mobile phase A was a 0.1% aqueous formic acid solution containing 1 mL of formic acid mixed with 1000 mL of distilled water, and mobile phase B was a 50% acetonitrile/0.1% formic acid solution containing 500 mL of acetonitrile mixed with 500 mL of distilled water and 1 mL of formic acid. The sample flowed in a concentration gradient of mobile phase A:B=100:0 to 90:10 at an analysis time from 0 to 10 minutes. The sample flowed in a concentration gradient of mobile phase A:B=90:10 to 0:100 at an analysis time from 10 to 12 minutes and in mobile phase A:B=0:100 at an analysis time from 12 to 15 minutes. The column used was ZORBAX SB-C18 (150×9.4 mm, Agilent Technologies, Inc.) at 35° C., and the flow rate was set to 4 mL/min. 80 μL of the sample solution thus filtered was injected to the LC-MS apparatus, and the peak of GA-pyridine was detected with the diode array detector (290 nm) and MS (cation detection). A peak having UV absorptivity was observed at an analysis time of 6 minutes, and the peak contained a cation at m/z=297.1. Accordingly, the peak at the retention time of 6 minutes was recovered by MS fractionation with m/z=297 as a trigger. The solution thus fractionated was concentrated to dryness with a rotary evaporator (Tokyo Rikakikai Co., Ltd.). The obtained precipitates were stored at −20° C.

(3) Structure Confirmation of GA-Pyridine

The obtained precipitates (4.7 mg) were dissolved in heavy water (0.6 mL, FUJIFILM Wako Pure Chemical Corp.) and transferred to a sample tube for nuclear magnetic resonance (NMR) (Shigemi Co., Ltd.) with an outside diameter of 5 mm. Then, the structure of GA-pyridine was confirmed in a NMR apparatus (AVANCE III HD, 500 MHz, CryoProbe mounted, Bruker Corp.). The total assignment of hydrogen was determined by comparing the obtained $^1$H-NMR spectrum data with NPL (Nagai et al., Journal of Biological chemistry, 2002, 277 (50), 48905-48912). Also, a $^1$H-$^{13}$C HSQC spectrum was analyzed to confirm the validity of the assignment. The structure of GA-pyridine is shown below.

[Chemical Formula 28]

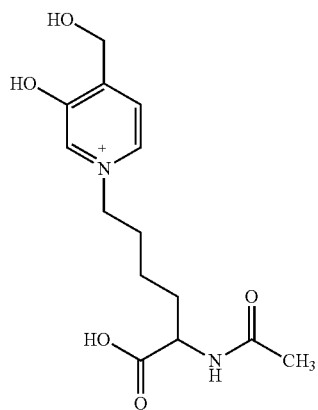

[Example 29] Preparation of Lysine Dimer Derived from Glyoxal (GOLD)

GOLD (Wells-Knecht et al., J. Org. Chem. 1995, 60, 6264-6247) was prepared by the following method.

(1) Preparation of Reaction Solution

N$^\alpha$-Acetyl-L-lysine (Ac-Lys-OH, Tokyo Chemical Industry Co., Ltd.) and a 40% glyoxal solution (Sigma-Aldrich Co. LLC) were obtained by purchase. 188 mg of Ac-Lys-OH was dissolved in a phosphate buffer solution (0.5 M, pH 7.4, 1 mL) to prepare a 1 M solution. The 1 M Ac-Lys-OH solution (500 μL), the 40% glyoxal solution (73 μL), and a 0.5 M phosphate buffer solution (427 μL) were mixed in a microtube and stirred with a vortex mixer. Then, the tube was hermetically sealed and heated at 95° C. for 5 minutes. The obtained reaction solution was stored at 4° C.

(2) Separation and Purification of GOLD

The GOLD reaction solution was filtered through a syringe filter (Millex-LG, Merck KGaA) with a pore size of 0.2 μm, and the filtrate was used as a sample for a liquid chromatograph-mass spectrometer (LC/MS). The LC and MS parts of LC/MS were composed in the same way as in Example 12. Mobile phases of HPLC grade were purchased from FUJIFILM Wako Pure Chemical Corp. Mobile phase A was a 0.1% aqueous formic acid solution containing 1 mL of formic acid mixed with 1000 mL of distilled water, and mobile phase B was a 50% acetonitrile/0.1% formic acid solution containing 500 mL of acetonitrile mixed with 500 mL of distilled water and 1 mL of formic acid. The sample flowed in a concentration gradient of mobile phase A:B=95:5 to 70:30 at an analysis time from 0 to 10 minutes. The sample flowed in a concentration gradient of mobile phase A:B=70:30 to 0:100 at an analysis time from 10 to 12 minutes and in mobile phase A:B=0:100 at an analysis time from 12 to 15 minutes. The column used was ZORBAX SB-C18 (150×9.4 mm, Agilent Technologies, Inc.) at 35° C., and the flow rate was set to 4 mL/min. 20 μL of the sample solution thus filtered was injected to the LC-MS apparatus, and the peak of GOLD was detected with the diode array detector (215 nm) and MS (cation detection). A peak having UV absorptivity was observed at an analysis time of 4.2 minutes, and the peak contained a cation at m/z=411.2. Accordingly, the peak at the retention time of 4.2 minutes was recovered by MS fractionation with m/z=411 as a trigger. The solution thus fractionated was concentrated to dryness with a rotary evaporator (Tokyo Rikakikai Co., Ltd.). The obtained precipitates were stored at −20° C.

(3) Structure Confirmation of GOLD

The obtained precipitates (6.7 mg) were dissolved in heavy water (0.6 mL, FUJIFILM Wako Pure Chemical Corp.) and transferred to a sample tube for nuclear magnetic resonance (NMR) (Shigemi Co., Ltd.) with an outside diameter of 5 mm. Then, the structure of GOLD was confirmed in a NMR apparatus (AVANCE III HD, 500 MHz, CryoProbe mounted, Bruker Corp.). The total assignment of hydrogen and carbon was determined from $^1$H-NMR and $^{13}$C-NMR spectrum data with reference to the literature described above. Also, $^1$H-1H COSY, $^1$H-$^{13}$C HSQC, and $^1$H-$^{13}$C HMBC spectra were analyzed to confirm the validity of the assignment. The structure of GOLD is shown below.

[Chemical Formula 29]

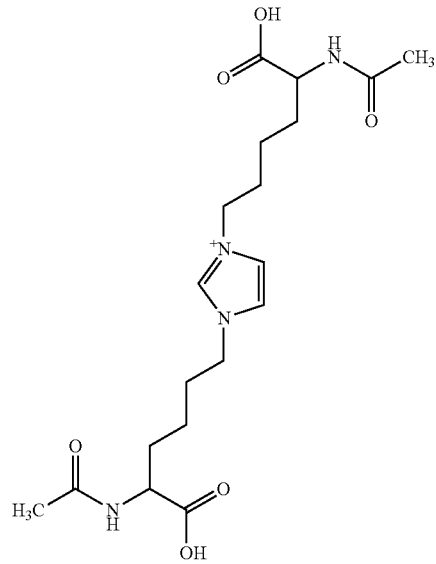

[Example 30] Confirmation of Specificity of Novel Monoclonal Antibody PB-1 by Competitive ELISA (1) Immobilization of Antigen A-peak-BSA or Glycer-AGEs-BSA prepared into a concentration of 1 μg/mL with a coating solution (Example 13) was added at 100 μL/well to a 96-well microtiter plate (Costar) and immobilized overnight at 4° C.

(2) Blocking

The plate was washed three times with PBS containing 0.05% (v/v) Tween 20 (PBS-T) and then blocked with PBS-T containing 0.5% (w/v) gelatin for 1 hour.

(3) Competitive Reaction

Bovine serum albumin (BSA), BSA containing AGEs derived from glucose (Glu-AGEs-BSA), BSA containing AGEs derived from fructose (Fru-AGEs-BSA), BSA containing AGEs derived from glycolaldehyde (Glycol-AGEs-BSA), BSA containing AGEs derived from glyceraldehyde (Glycer-AGEs-BSA), BSA containing Ne-carboxyethyllysine (CEL-AGEs-BSA), BSA containing Ne-carboxymethyllysine (CML-AGEs-BSA), BSA containing AGEs derived from glyoxal (GO-AGEs-BSA), BSA containing AGEs derived from methylglyoxal (MGO-AGEs-BSA), and A-peak-BSA diluted into 10 μg/mL with PBS-T containing 0.1% (w/v) gelatin were each added at 50 μL/well to the antigen-immobilized plate, and the PB-1 antibody diluted into 0.05 μg/mL with PBS-T containing 0.1% (w/v) gelatin was further added at 50 μL/well, stirred with a plate mixer, and then left standing at room temperature for 1 hour.

(4) Reaction with Antibody for Detection

After washing, peroxidase-labeled anti-mouse IgG (H+L) polyclonal antibody, F(ab')$_2$ fragment (Kirkegaard & Perry Laboratories, Inc.) diluted into 0.05 μg/mL with PBS-T containing 0.1% (w/v) gelatin was added at 100 μL/well and left standing at room temperature for 1 hour.

(5) Color Development and Absorbance Measurement

After washing, ELISA POD substrate TMB kit (Nacalai Tesque, Inc.) was added at 100 μL/well and left standing at room temperature in the dark. Ten minutes later, color development was terminated by the addition of 2 N sulfuric acid (50 μL/well). Absorbance was measured at a dominant wavelength of 450 nm and a sub-wavelength of 650 nm with a microplate reader (Cytation 5, BioTek Instrument Inc.), and the absorbance at the sub-wavelength was subtracted from the absorbance at the dominant wavelength.

Figure 26A:
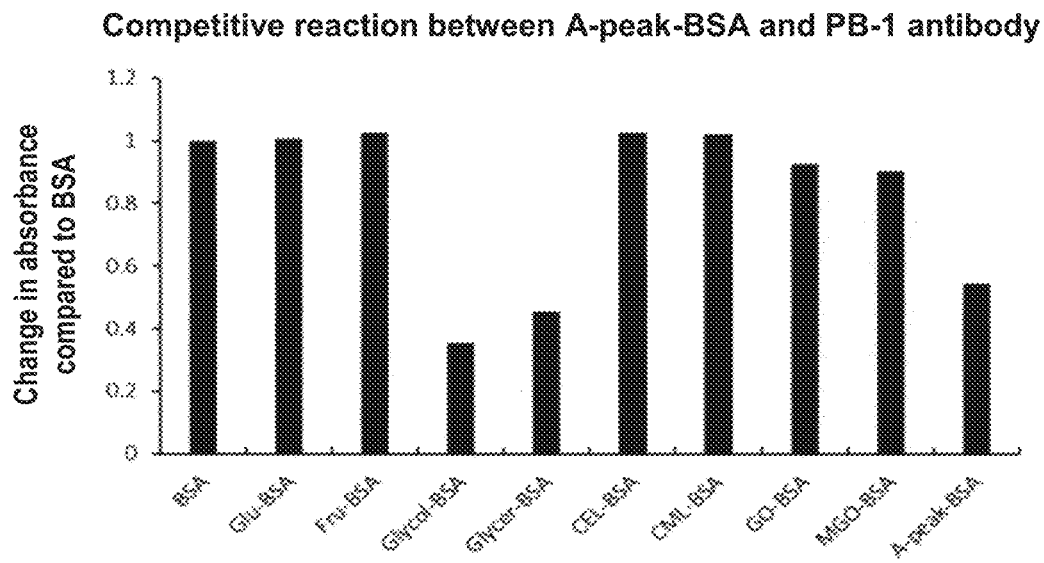
FIG. 26A is a graph showing results of a test to confirm the specificity of the PB-1 antibody when A-peak-BSA was used as an immobilized antigen.
Figure 26B:
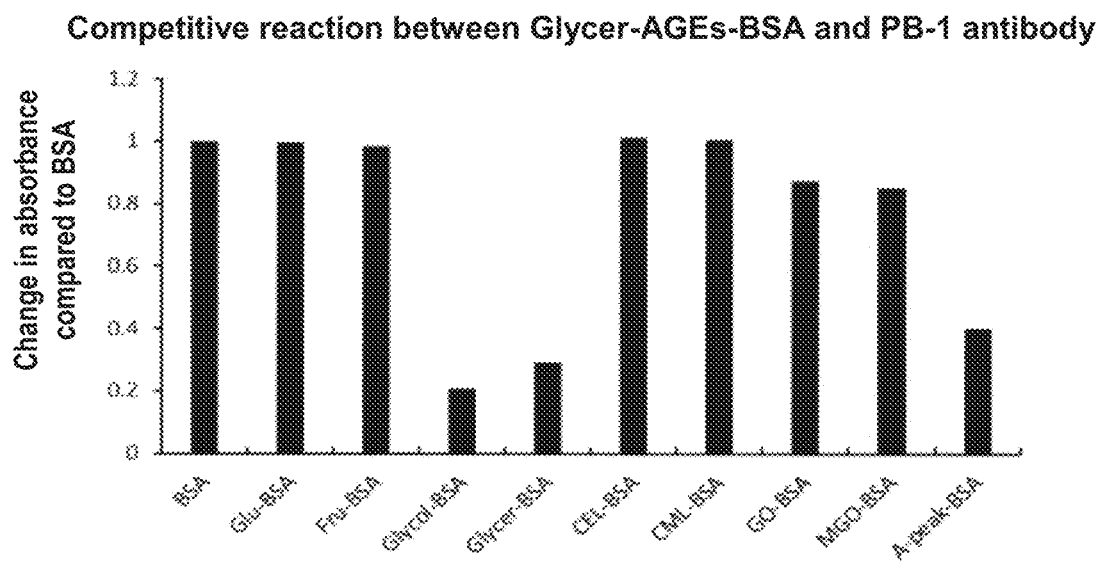
FIG. 26B is a graph showing results of a test to confirm the specificity of the PB-1 antibody when Glycer-AGEs-BSA was used as an immobilized antigen.

FIG. 26A shows the results about the specificity of the PB-1 antibody when A-peak-BSA was used as an immobilized antigen. FIG. 26B shows absorbance relative to that of control BSA defined as 1 as the results about the specificity of the PB-1 antibody when Glycer-AGEs-BSA was used as an immobilized antigen. The ordinate of the graph depicts change in absorbance relative to that of control BSA defined as 1. When A-peak-BSA and Glycer-AGEs-BSA were immobilized, the novel monoclonal antibody PB-1 was also positive to Glycol-AGEs-BSA, Glycer-AGEs-BSA, and A-peak-BSA and negative to Glu-AGEs-BSA, Fru-AGEs-BSA, CEL-AGEs-BSA, CML-AGEs-BSA, GO-AGEs-BSA, and MGO-AGEs-BSA in terms of specificity.

[Example 31] Reactivity Evaluation of Novel Monoclonal Antibody PB-1 by Competitive ELISA (1) Immobilization of Antigen Competitive ELISA was conducted using the reagents described in Example 13. A solution of A-peak-BSA prepared into 1 μg/mL in a coating solution was added at 100 μL/well to a 96-well microtiter plate (Costar) and incubated overnight at 4° C.

(2) Blocking

Each well after the immobilization treatment was washed three times with a washing solution (300 μL), and a blocking solution (200 μL) was added thereto and left at room temperature for 1 hour.

(3) Competitive Experiment

GAL691 (prepared in Example 16), GLAP (prepared in Example 12), Lys-hydroxy-triosidine (prepared in Example 17), GA-pyridine (prepared in Example 28), GOLD (prepared in Example 29), and Z-Lys were each dissolved in a phosphate buffer solution (0.2 M, pH 7.4) to prepare a 100 mM solution. Then, a 10 mM solution was prepared by dilution 10-fold with a diluting solution containing BSA (1 mg/mL, FUJIFILM Wako Pure Chemical Corp.). Sample solutions of 4-fold dilution series of 0.04, 0.16, 0.63, and 2.5 mM were further prepared with a diluting solution containing a 10% (v/v) phosphate buffer solution and 1 mg/mL BSA. Ten-fold dilutions of a phosphate buffer solution with a diluting solution containing 1 mg/mL BSA were prepared as blank solutions containing no sample in the same way as above. A 0.1 μg/mL solution of the PB-1 antibody was prepared with a diluting solution containing 1 mg/mL BSA.

Each well treated with the blocking solution was washed three times with a washing solution (300 μL), and the sample solutions of 4-fold dilution series (50 μL each) and the PB-1 antibody dilution solution (50 μL) were added thereto, stirred with a plate mixer for 2 minutes, and then incubated at room temperature for 1 hour.

(4) Reaction with Antibody for Detection

After the competitive reaction, each well was washed three times with a washing solution (300 μL), and peroxidase-labeled anti-mouse IgG (H+L) polyclonal antibody, F(ab')$_2$ fragment (Kirkegaard & Perry Laboratories, Inc.) diluted into 0.05 μg/mL with a diluting solution containing 1 mg/mL BSA was added at 100 μL/well and left standing at room temperature for 1 hour.

(5) Color Development

After washing three times with a washing solution (300 μL), a substrate solution (ELISA POD substrate TMB kit (Popular), Nacalai Tesque, Inc.) was added at 100 μL/well and incubated at room temperature for 10 minutes under light shielding. Then, color development was terminated by the addition of 2 N sulfuric acid (50 μL).

(6) Absorbance Measurement and Data Analysis

Figure 27:
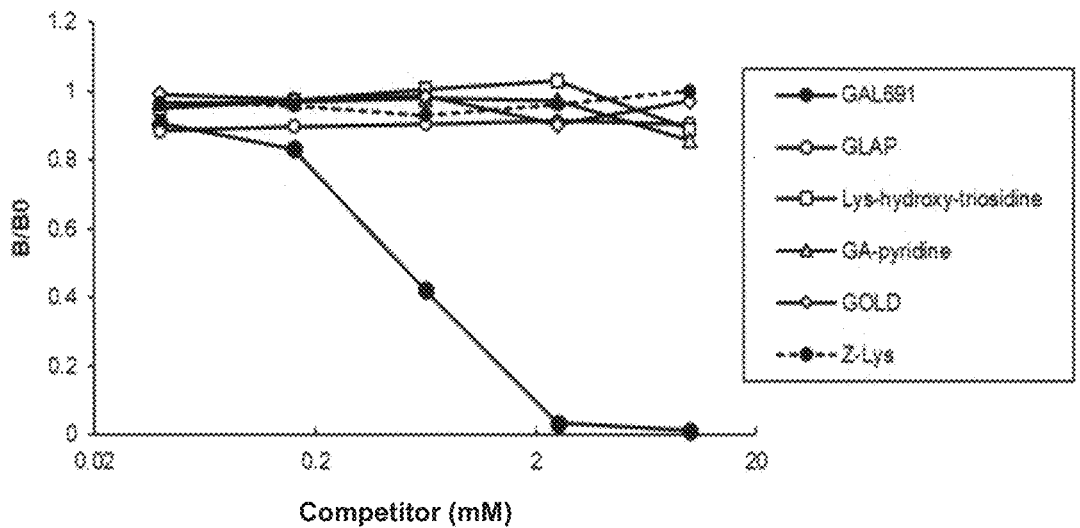
FIG. 27 is a graph showing results of a reactivity evaluation test of the novel monoclonal antibody PB-1 with AGEs known in the art by competitive ELISA.

Absorbance was measured at a dominant wavelength of 450 nm and a sub-wavelength of 650 nm with a microplate reader (Cytation 5, BioTek Instrument Inc.), and the absorbance at the sub-wavelength was subtracted from the absorbance at the dominant wavelength. Change in the absorbance of GAL691, GLAP, Lys-hydroxy-triosidine, GA-pyridine, GOLD, and Z-Lys was indicated as relative values to the absorbance of the blank solution. The results are shown in FIG. 27. The absorbance was reduced in a concentration-dependent manner for GAL691, whereas no reduction in absorbance was observed for the other compounds. This demonstrated that the novel monoclonal antibody PB-1 is an antibody that binds to the novel structure of AGEs derived from glyceraldehyde and does not recognize GLAP and Lys-hydroxy-triosidine (AGEs derived from glyceraldehyde known in the art), GA-pyridine (AGEs derived from glycolaldehyde known in the art), and GOLD (AGEs derived from glyoxal).

[Example 32] Suppression Test of DAB Oxidation of A-Peak-BSA Using PB-1 Antibody (1) Preparation of Reaction Solution Diaminobenzidine (DAB, Dojindo Laboratories) was prepared into 5 mg/mL in a PBS solution. A-peak-BSA (2 mg/mL, PBS solution) was prepared in the same way as in Example 24. 10 μL of the DAB solution was added to a 0.6 mL microtube (Watson), and 100 μL of PBS, the PB-1 antibody (1.8 mg/mL), or a mouse IgG isotype control (Ctrl-mIgG, Thermo Fisher Scientific Inc.) was further added thereto. After stirring with a vortex mixer, 10 μL of the A-peak-BSA solution was added thereto. These solutions were stirred with a vortex mixer and then irradiated overnight with white LED (3000 lux). The solutions thus irradiated with light were stirred with a vortex mixer, then spun down, and recovered at 100 μL/well into Violamo 96-well plate (AS ONE Corp.).

(2) Absorbance Measurement and Data Analysis

Figure 28:
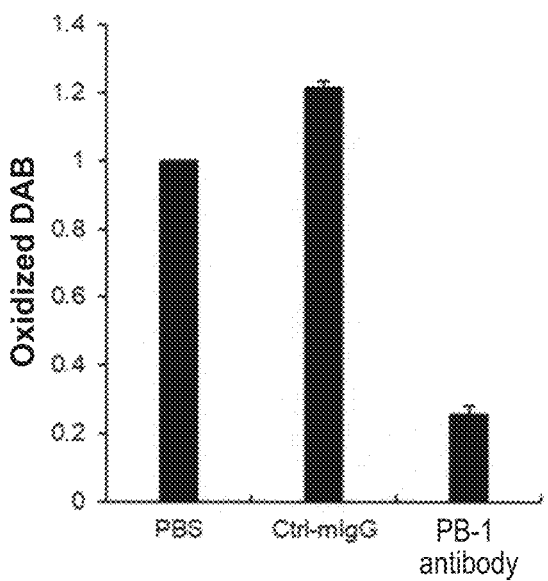
FIG. 28 is a graph showing results of a test for confirming the effect of suppressing the DAB oxidative activity of A-peak-BSA by the PB-1 antibody.
Figure 29:
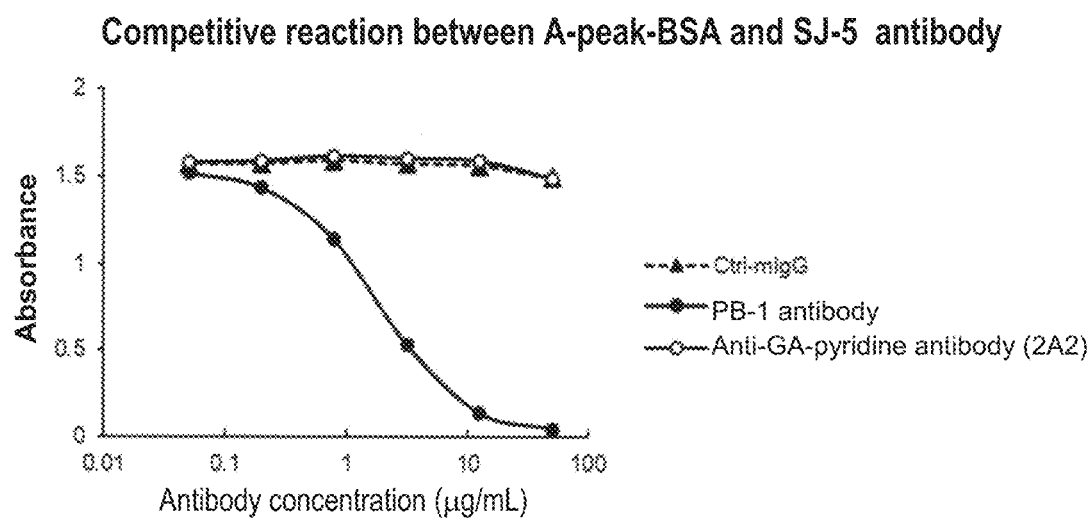
FIG. 29 is a graph showing results of a test to confirm the cross-competition of the SJ-5 antibody or an anti-GA-pyridine monoclonal antibody with the PB-1 antibody.

Absorbance at a wavelength of 460 nm was measured with a microplate reader (Cytation 5, BioTek Instrument Inc.) to detect oxidized DAB. The results are shown in FIG. 28. The ordinate of the graph depicts a relative value to oxidized DAB detected in the antibody-untreated group (PBS addition group). The oxidized DAB was largely decreased in the PB-1 antibody treatment group as compared with the PBS treatment group or the Ctrl-mIgG treatment group. From this result, the PB-1 antibody was shown to be able to suppress the DAB oxidizing effect of the novel structure of AGEs derived from glyceraldehyde by binding to the novel structure.

[Example 33] Cross-Competition of SJ-5 Antibody with Anti-GA-Pyridine Monoclonal Antibody GA-pyridine, AGEs derived from glycolaldehyde, has been reported by Nagai et al. (Nagai et al., Journal of Biological chemistry, 2002, 277 (50), 48905-48912), and a monoclonal antibody against GA-pyridine (clone name: 2A2) has also been established. Accordingly, the newly established SJ-5 antibody was studied for its cross-reactivity with the PB-1 antibody and the anti-GA-pyridine antibody 2A2 by competitive ELISA. Some reagents used in competitive ELISA were prepared in the same way as in Example 13.

(1) Immobilization of Antigen

A solution of A-peak-BSA prepared into 1 μg/mL in a coating solution was added at 100 μL/well to a 96-well microtiter plate (Costar) and incubated overnight at 4° C.

(2) Blocking

Each well after the immobilization treatment was washed three times with a washing solution (300 μL), and PBS containing 0.05% Tween 20 (PBS-T) and containing 0.5% gelatin dissolved therein (200 μL) was added thereto and left standing at room temperature for 1 hour.

(3) Competitive Experiment

The PB-1 antibody, a mouse IgG isotype control (Ctrl-mIgG, Thermo Fisher Scientific Inc.), and the anti-GA-pyridine antibody 2A2 (Cosmo Bio Co., Ltd.) were each diluted with PBS-T containing 0.1% gelatin to prepare 4-fold dilution series (0.049 to 50 μg/mL). Also, a HRP-labeled SJ-5 antibody (Example 4) was diluted 10000-fold with PBS-T containing 0.1% gelatin.

Each well treated with the blocking solution was washed three times with a washing solution (300 μL), and the sample solutions of 4-fold dilution series (50 μL each) and the HRP-labeled SJ-5 antibody dilution solution (50 μL) were added thereto, stirred with a plate mixer for 2 minutes, and then incubated at room temperature for 1 hour.

(4) Color Development

After washing three times with a washing solution (300 μL), a substrate solution (ELISA POD substrate TMB kit (Popular), Nacalai Tesque, Inc.) was added at 100 μL/well and incubated at room temperature for 10 minutes under light shielding. Then, color development was terminated by the addition of 2 N sulfuric acid (50 μL).

(5) Absorbance Measurement and Data Analysis

Absorbance was measured at a dominant wavelength of 450 nm and a sub-wavelength of 650 nm with a microplate reader (Cytation 5, BioTek Instrument Inc.), and the absorbance at the sub-wavelength was subtracted from the absorbance at the dominant wavelength. The results are shown in FIG. 20. In the reaction of the SJ-5 antibody with A-peak-BSA, the absorbance was decreased in a PB-1 concentration-dependent manner by the addition of PB-1. On the other hand, the decrease in absorbance was not observed for Ctrl-mIgG or the anti-GA-pyridine antibody 2A2, which thus did not cross-compete. Thus, it was shown that the SJ-5 antibody and the PB-1 antibody are antibodies that recognize the same epitope, or the anti-GA-pyridine antibody is an antibody that does not recognize the epitope for the SJ-5 antibody.

[Example 34] Tight Junction Breakdown Suppression Test of Retinal Pigment Epithelial Cell (ARPE-19 Cell)

Retinal pigment epithelial cells form the blood-retina barrier by the intercellular tight junction, thereby limiting mass transfer from choroidal vessels and maintaining the functions of the retina. The breakdown of the blood-retina barrier is considered to cause diseases such as diabetic retinopathy, and the tight junction of the retinal pigment epithelial cells is very important for keeping the functions of the retina (Willermain et al., Int. J. Mol. Sci., 2018, 19 (4), pii: E1056.). xCELLigence RTCA DP system is an instrument with electrodes installed on the well bottom surface. This instrument is capable of measuring the impedance of the well bottom surface, without influencing the functions of cells, by injecting small current to the well bottom surface. It has been revealed that the impedance increases by the formation of the intercellular tight junction and decreases by the breakdown of the tight junction (Wittchen et al., Invest. Ophthalmol. Vis. Sci., 2011, 52 (10), 7455-63). In this Example, the influence of A-Peak-BSA on the tight junction of retinal pigment epithelial cells (ARPE-19) was confirmed using the xCELLigence RTCA DP system, and the SJ-5 antibody and the PB-1 antibody were evaluated for their suppressive effects thereon.

(1) Cell Culture

FBS (FUJIFILM Wako Pure Chemical Corp.) was added at 10% to D-MEM (FUJIFILM Wako Pure Chemical Corp.), and penicillin-streptomycin (Nacalai Tesque, Inc.) was added at 1% thereto to prepare DMEM medium. ARPE-19 cells (ATCC) were cultured in the DMEM medium using a 10 cm dish (Corning Inc.).

(2) Measurement Plate xCELLigence RTCA DP system (ACEA Biosciences, Inc.) was installed in a $CO_2$ incubator and used in a state loaded overnight or longer after the installation for stabilization. Immediately before cell preparation, DMEM medium was added at 50 μL/well to E-plate (ACEA Biosciences, Inc.), and a background was measured.

(3) Cell Preparation

The medium was removed from the ARPE-19 cells cultured in (1) described above, which were then washed by repeating the addition and removal of 10 mL of PBS(−) (FUJIFILM Wako Pure Chemical Corp.) twice. 1 mL of trypsin-EDTA (FUJIFILM Wako Pure Chemical Corp.) was added thereto, and the cells were dispersed by incubation in a $CO_2$ incubator (Taitec Corp.) at 37° C. for 3 minutes. Then, the activity of trypsin was neutralized by the addition of 10 mL of DMEM medium. The neutralized cell dispersion was transferred to a 50 mL tube (Falcon) and centrifuged at 1500 rpm for 5 minutes using a centrifuge (Kubota Corp.). Then, the supernatant was discarded, and the precipitates were resuspended in 1 mL of DMEM medium. A 10 μL aliquot of the resuspended cell dispersion was mixed with 10 μL of Trypan Blue (NanoEnTek Inc.), and 10 μL thereof was added to a counting chamber (NanoEnTek Inc.). Then, the number of live cells was counted in Auto Cell Counter EVE (NanoEnTek Inc.). The cell suspension was diluted into $4.0 \times 10^5$ cells/mL with DMEM medium and inoculated at 80 μL/well to E-plate (ACEA Biosciences, Inc.).

(4) Addition of Antibody and A-Peak-BSA

The impedance of the plate was measured every 15 minutes using the xCELLigence RTCA DP system to confirm the adhesion of the cells to the plate. Twenty to 24 hours after the cell inoculation, 9 μL of the PB-1 antibody (10 mg/mL), the PB-1 antibody (3 mg/mL), the PB-1 antibody (1 mg/mL), the PB-1 antibody (0.3 mg/mL), the SJ-5 antibody (10 mg/mL), or PBS and 1 μL of A-peak-BSA (10 mg/mL) were added thereto. For a control, 10 μL of PBS was added thereto 20 to 24 hours thereafter. After the addition, the impedance was also measured every 15 minutes.

Figure 30:
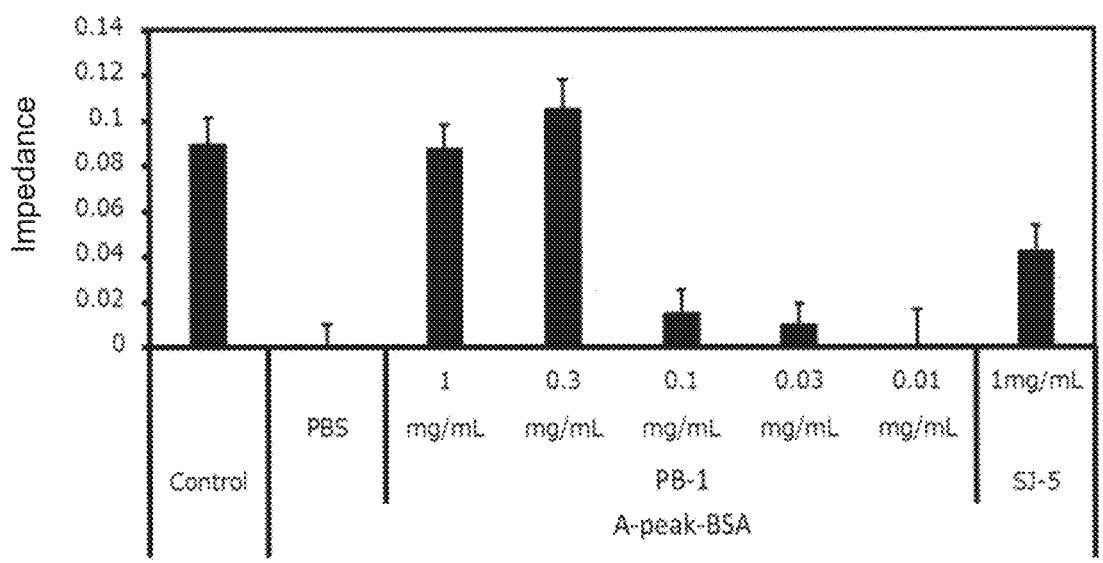
FIG. 30 is a graph showing results of a tight junction breakdown suppression test of retinal pigment epithelial cells (ARPE-19 cells), and is a graph showing results of measuring the impedance of the well bottom surface in order to confirm the formation of an intercellular tight junction.

The impedance was measured 10 to 12 hours after the addition of A-peak-BSA and normalized to that of the A-peak-BSA addition group defined as 0. The results are shown in FIG. 30. As shown in the drawing, the impedance was confirmed to be significantly reduced by the addition of A-Peak-BSA. This reduction in impedance was significantly suppressed by the addition of the PB-1 antibody. Also, the suppression of the reduction was found in the SJ-5 antibody addition group with the final concentration of 1 mg/mL, whereas stronger suppression than that by the SJ-5 antibody was found by the addition of the PB-1 antibody even in a lower concentration region. These results suggested that A-peak-BSA induces the breakdown of the tight junction of retinal pigment epithelial cells, and the addition of the PB-1 antibody or the SJ-5 antibody is capable of suppressing it.

[Example 35] Neutralization Test of Vascular Endothelial Cell Lumen Formation Inhibition of Glycer-AGEs-BSA Using PB-1 Antibody (1) Preparation of Matrigel Matrix Matrigel matrix was prepared by the same operation as in Example 14.

(2) Preparation of Reaction Solution of Glycer-AGEs-BSA and Antibody

10 L of Glycer-AGEs-BSA (10 mg/mL) prepared in Example 1, 10 µL of phosphate-buffered saline (PBS, FUJIFILM Wako Pure Chemical Corp.), and 90 µL of the PB-1 antibody (10 mg/mL) or a control antibody (10 mg/mL) were added to a 1.5 mL tube (Watson) and left standing at room temperature for 10 minutes. Then, a supernatant was recovered by centrifugation at 14000 rpm for 15 minutes using a centrifuge (Thermo Fisher Scientific Inc.).

Figure 31:
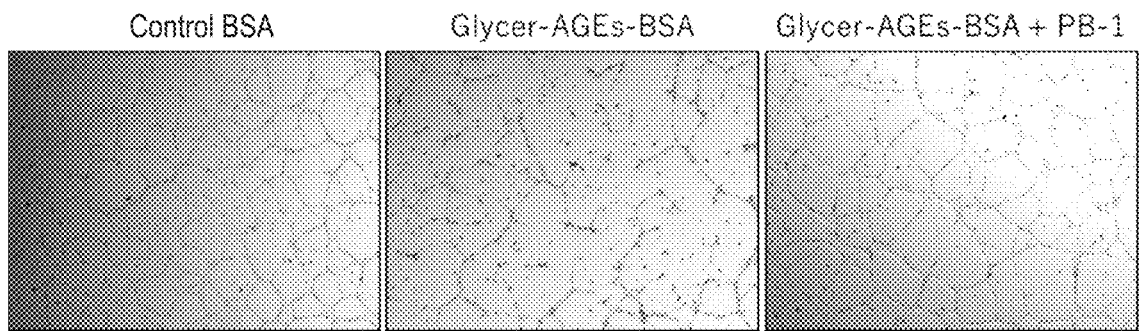
FIG. 31 is a photograph showing the morphology of HUVEC cultured for 8 hours in an endothelial cell lumen formation inhibition test in Example 35.

(3) A lumen formation inhibition test was conducted by the same operation as in Example 14. The morphology of HUVEC after 8-hour culture is shown in FIG. 31. As shown in the drawing, HUVEC was confirmed to form a lumen in the Matrigel matrix in the control BSA addition group. However, Glycer-AGEs-BSA inhibited lumen formation. Furthermore, this inhibition of lumen formation was neutralized by the reaction solution of PB-1. This result demonstrated that the PB-1 antibody is capable of neutralizing the influence of Glycer-AGEs-BSA on HUVEC.

[Example 36] Retinal Tissue Staining of Diabetic Mouse and Control Mouse with PB-1 Antibody (1) Raising of Mouse A C57BL6/J mouse (CLEA Japan, Inc.) on 13 days of pregnancy was purchased, and child mice were obtained. For diabetic mice, streptozotocin (FUJIFILM Wako Pure Chemical Corp.) was dissolved at 5 mg/mL in saline (Otsuka Pharmaceutical Co., Ltd.) and subcutaneously administered at 300 µL to a male child mouse 2 days afterbirth. For control mice, saline was subcutaneously administered at 300 µL to a male child mouse 2 days after birth. After living together with the mother mouse for 4 weeks and subsequent weaning, the diabetic mice were raised with HFD32 (CLEA Japan, Inc.) for 8 weeks. The control mice were raised with CE-2 (CLEA Japan Inc.) for 8 weeks.

(2) Anatomy 1.875 mL of Domitor (Nippon Zenyaku Kogyo Co., Ltd.), 2 mL of midazolam (Sandoz K.K.), 2.5 mL of Vetorphale (Meiji Seika Pharma Co., Ltd.), and 18.625 mL of saline were mixed to prepare a three drug-mixed anesthetic. The body weight of each mouse was measured with a scale (TANITA Corp.), and the three drug-mixed anesthetic was intraperitoneally administered at 0.1 mL/g. The effect of the anesthesia was confirmed from the disappearance of hind limb flexion withdrawal reflex. The abdomen and the chest were opened with tweezers (Natsume Seisakusho Co., Ltd.) and scissors (Natsume Seisakusho Co., Ltd.), and the inferior vena cava was cut. Perfusion was performed by the administration of 10 mL of saline from the left ventricle, and the eyeballs were excised after the perfusion. The excised eyeballs were dipped in Cryomold (Sakura Finetek Japan Co., Ltd.) filled with OCT Compound (Sakura Finetek Japan Co., Ltd.), and frozen in liquid nitrogen to prepare a fresh frozen block. The block thus prepared was stored in a deep freezer (Thermo Fisher Scientific Inc.) set to −80° C.

(3) Slicing and Staining

Acetone (FUJIFILM Wako Pure Chemical Corp.) was incubated for 16 hours or longer in a freezer (Fukushima Industries Corp.) set to −30° C. to prepare cold acetone. Triton X-100 (Nacalai Tesque, Inc.) was added at 0.1% to PBS to prepare PBS-T. The fresh frozen block was sliced into a thickness of 10 µm with Cryostat CM1950 (Leica Camera AG). The sliced tissue was affixed to MAS-coated slide glass (Matsunami Glass Ind., Ltd.) and dried. The tissue thus dried was fixed by incubation in cold acetone for 10 minutes. After the fixation, washing was performed twice with PBS-T for 10 minutes. After the washing, Fc block (BioLegend) was diluted 50-fold with TBS-T containing 5% BSA (Sigma-Aldrich Co. LLC) dissolved therein to prepare a blocking solution, followed by blocking by incubation at room temperature for 30 minutes. After the blocking, the PB-1 antibody (1 mg/mL) or a control antibody (1 mg/mL) was diluted 500-fold with TBS-T containing 1% BSA dissolved therein to prepare a primary antibody reaction solution, which was then incubated overnight in a refrigerator (Fukushima Industries Corp.) set to 4° C. After the primary antibody reaction, washing was performed twice with PBS-T for 10 minutes. Alexa 594-labeled Goat Anti-Mouse IgG H&L (Abcam plc) was diluted 100-fold with TBS-T containing 1% BSA dissolved therein to prepare a secondary antibody reaction solution, which was then reacted at room temperature for 1 hour under light shielding. After the secondary antibody reaction, washing was performed twice with PBS-T for 10 minutes. Vector Shield (Vector Laboratories Inc.) was added as an embedding agent to the stained tissue, which was then enclosed with cover glass (Matsunami Glass Ind., Ltd.). Then, the fluorescence of Alexa 594 in the retina was observed under a confocal laser microscope (Olympus Corp.).

(4) Results

Figure 32:
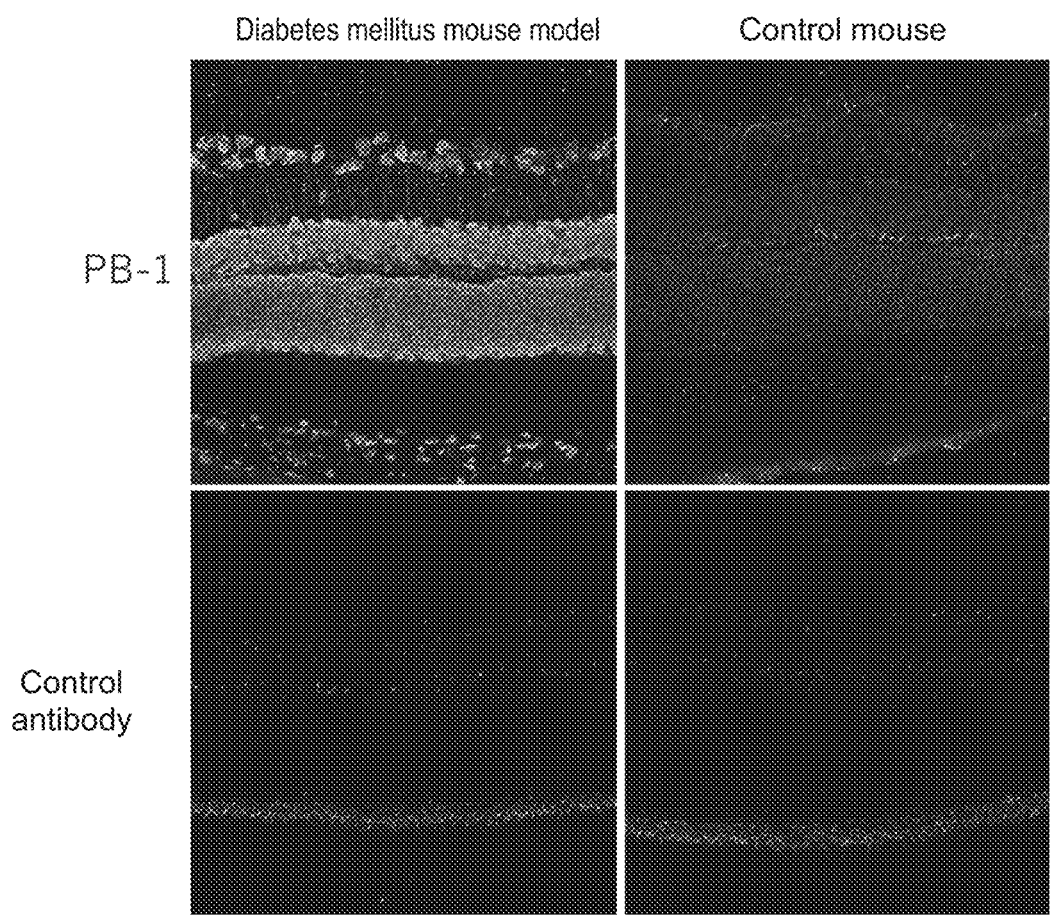
FIG. 32 is a photograph showing results of observing a mouse retinal tissue stained with the PB-1 antibody under a confocal laser microscope.

The results are shown in FIG. 32. The PB-1 antibody was found to bind strongly to the retinal ganglion cell layer, internal granular layer, external granular layer, and retinal pigment epithelial cell layer of the diabetic mice as compared with the control mice. When the staining properties of the control antibody was confirmed in the diabetic mice, similar staining results were not obtained, demonstrating that the obtained staining properties are attributed to the specific binding of the variable regions of the PB-1 antibody. These results demonstrated that AGE having an epitope structure for the PB-1 antibody exists in vivo and exists in the retinal ganglion cell layer, internal granular layer, external granular layer, and retinal pigment epithelial cell layer in the retina of the diabetic mice. It was also demonstrated that the PB-1 antibody serves as a useful tool for confirming the presence of the novel structure by immunostaining.

[Example 37] Purification of Human Serum Protein Using PB-1 Antibody Column and Detection by Western Blotting (1) Preparation of PB-1 Antibody Column The solvent for the PB-1 antibody was replaced with a coupling buffer solution (0.2 M sodium carbonate, 0.5 M NaCl, pH 8.3) through a PD10 column (GE Healthcare Japan Corp.) to prepare 1 mL of a 10 mg/mL PB-1 antibody solution. The coupling support used was NHS-activated Sepharose 4 Fast Flow (GE Healthcare Japan Corp.). 10 mL of 1 mM HCl cooled in an ice bath was injected to 1 mL of NHS-activated Sepharose 4 Fast Flow, immediately thereafter mixed with the preliminarily prepared 10 mg/mL PB-1 antibody solution, and mixed by inversion (4° C., overnight) using a rotator (Taitec Corp.) so that the PB-1 antibody was immobilized to the coupling support. Then, 3 mL each of a buffer solution for blocking (0.1 M Tris-HCl, pH 8.0) and a buffer solution for washing (0.1 M sodium acetate, 0.5 M NaCl, pH 5.0) was injected thereto in order, and this operation was repeated three times. Finally, the solvent was replaced by the injection of 10 mL of PBS, followed by storage at 4° C.

(2) Purification of Human Serum Protein Using PB-1 Antibody Column

The purification sample used was human serum (pool) (Cosmo Bio Co., Ltd.). First, 10 mL of the human serum (pool) was diluted 7-fold with a binding buffer solution (0.02 M Tris-HCl, 0.03 mM NaCl, pH 7.4) and purified using 30 mL of SP Sepharose Fast Flow (GE Healthcare Japan Corp.) according to the product's manual. The obtained eluted fraction was dialyzed using a binding buffer solution and then purified using 3 mL of Protein G Sepharose 4 Fast Flow (GE Healthcare Japan Corp.) according to the product's manual to remove IgG. The obtained pass-through fraction was purified as a sample using 1 mL of the PB-1 antibody column. Each fraction obtained by purification was analyzed by electrophoresis (SDS-PAGE) according to a routine method.

Figure 33:
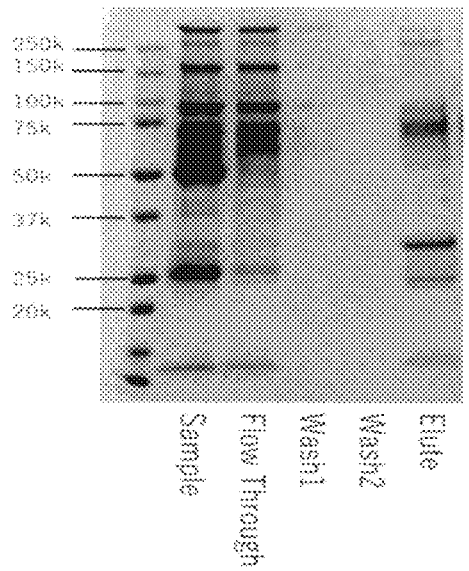
FIG. 33 is a diagram showing results of purifying a sample using a PB-1 antibody column prepared in Example 37, and analyzing each fraction by electrophoresis (SDS-PAGE).

The results of SDS-PAGE are shown in FIG. 33. The sample (in the drawing, Sample) was allowed to flow through the PB-1 antibody column (in the drawing, Flow Through). Then, 25 mL of a binding buffer solution was repetitively injected thereto twice (in the drawing, Wash1 and Wash2). Then, the protein bound to the PB-1 antibody column was eluted with 10 mL of an elution buffer solution (0.1 M glycine, pH 3.0) (in the drawing, Elute). The eluate was immediately neutralized by the addition of 0.4 mL of a neutralization buffer solution (1 M Tris-HCl, pH 9.0). As a result of SDS-PAGE, the majority of foreign proteins was removed, showing that the purity of the purification sample is enhanced.

(3) Western Blotting Using PB-1 Antibody

The protein purified through the PB-1 antibody column was electrophoresed (SDS-PAGE) according to a routine method, electrically transferred to a PVDF membrane, and subjected to Western blotting. The antibody reaction was performed using the PB-1 antibody as a primary antibody and Peroxidase-conjugated AffiniPure Goat Anti-Mouse IgG (H+L) (Jackson ImmunoResearch Laboratories, Inc.) as a secondary antibody. In order to exclude nonspecific signals ascribable to the binding of the secondary antibody, antibody reaction using only the secondary antibody was also performed. Next, color was developed using ECL Western Blotting Detection Reagents (GE Healthcare Japan Corp.) to detect a protein band.

Figure 34:
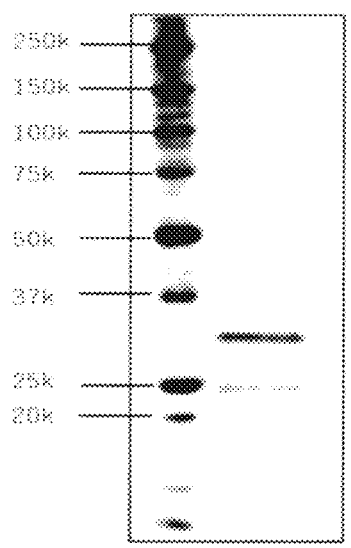
FIG. 34 is a diagram showing results of electrophoresing (SDS-PAGE) a protein purified with the PB-1 antibody column prepared in Example 37, and electrically transferring the protein to a PVDF membrane, followed by Western blotting.

No band was detected in the PVDF membrane reacted with only the secondary antibody. On the other hand, a band was detected only in the PVDF membrane reacted with the PB-1 antibody (FIG. 34). From this result, Western blotting using the PB-1 antibody was shown to be capable of detecting a protein modified with the novel structure in human serum.

SEQUENCE LISTING

PCT_for advanced glycation end products_20190829_175921_31.txt

---

The invention claimed is:

1. A compound represented by formula (I) or (II):

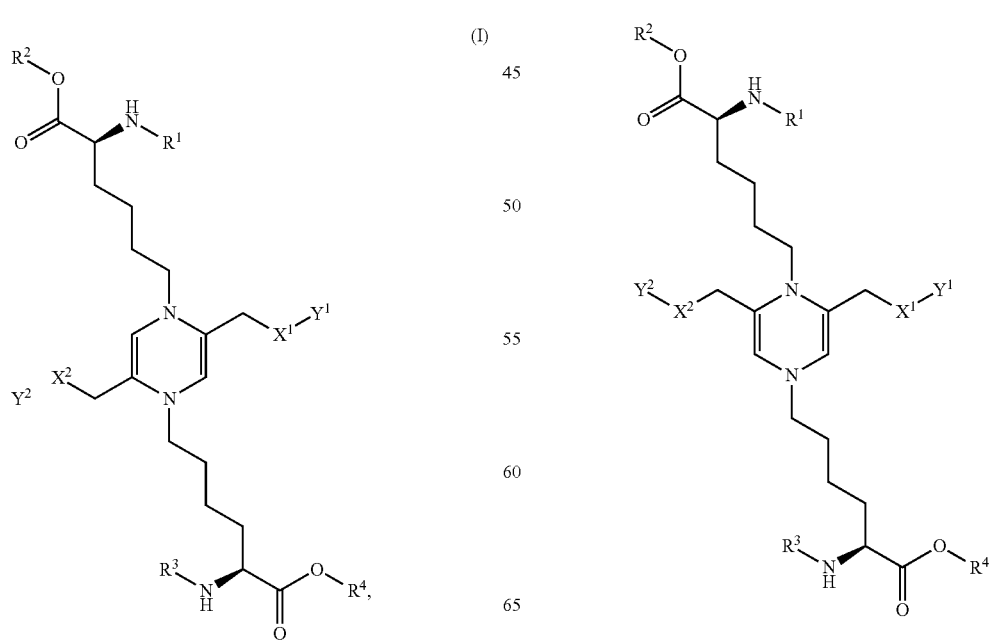

wherein R¹, R², R³ and R⁴ are each independently selected from a hydrogen atom, a protecting group, and a peptide group having 1 to 1000 amino acid residues, X¹ and X² represent —O— or —NH—;

Y¹ and Y² are a hydrogen atom, a protecting group, or a group:

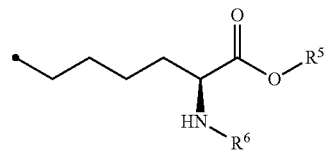

R⁵ and R⁶ are each independently selected from a hydrogen atom, a protecting group, and a peptide group having 1 to 1000 amino acid residues;

or a cationic radical thereof, or a dication thereof or a salt thereof.

2. A method for preparing an antibody, which comprises:

1) reacting lysine in which an amino group at α-position is protected and glyceraldehyde to obtain a reaction mixture;

2) fractionating the reaction mixture to obtain a fraction containing a compound represented by formula (Ia), (Ib), (IIa), or (IIb):

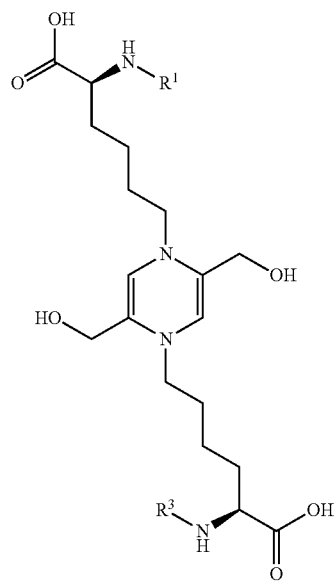

(Ia)

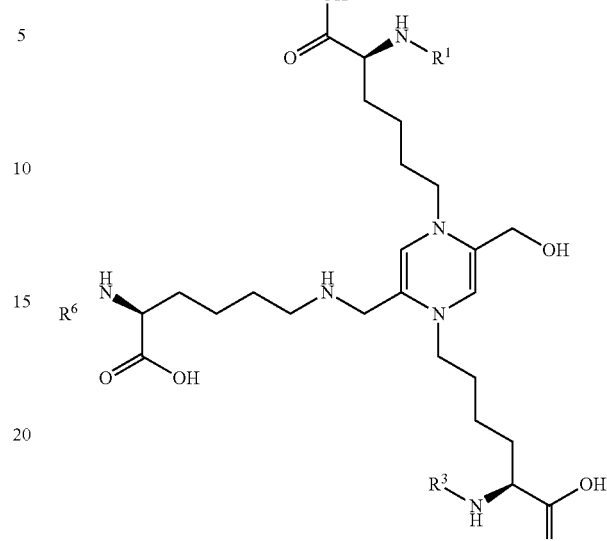

(Ib)

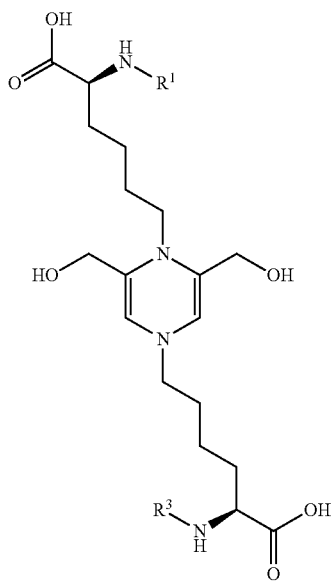

(IIa)

-continued
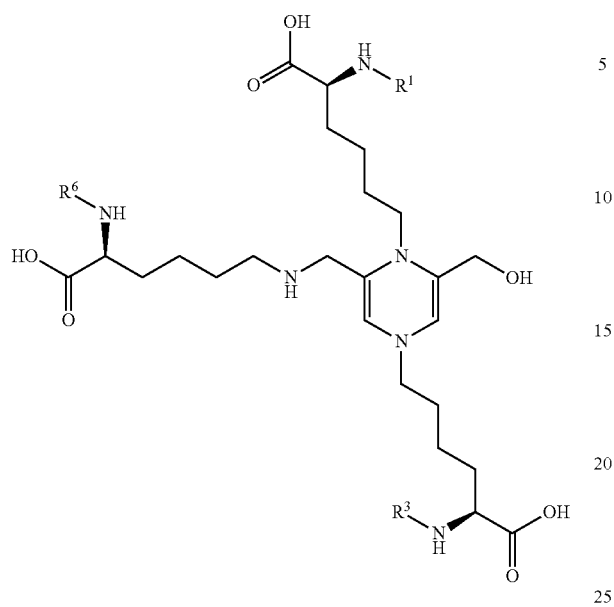
(IIb)
wherein $R^1$, $R^3$, and $R^6$ are protecting groups
3) immunizing an animal using the fraction as an antigen to obtain an antibody.
\* \* \* \* \*

SEQUENCE LISTING

```
<160> NUMBER OF SEQ ID NOS: 22

<210> SEQ ID NO 1
<211> LENGTH: 10
<212> TYPE: PRT
<213> ORGANISM: Mus musculus

<400> SEQUENCE: 1

Gly Phe Thr Phe Ser Ser Tyr Gly Met Ser
1               5                   10

<210> SEQ ID NO 2
<211> LENGTH: 17
<212> TYPE: PRT
<213> ORGANISM: Mus musculus

<400> SEQUENCE: 2

Val Ala Thr Ile Ser Gly Gly Gly Ser Tyr Thr Tyr Tyr Pro Asp Ser
1               5                   10                  15

Val

<210> SEQ ID NO 3
<211> LENGTH: 12
<212> TYPE: PRT
<213> ORGANISM: Mus musculus

<400> SEQUENCE: 3

Arg Gly Ala Tyr Gly Asp Tyr Gly Trp Phe Ala Tyr
1               5                   10

<210> SEQ ID NO 4
```

-continued

```
<211> LENGTH: 121
<212> TYPE: PRT
<213> ORGANISM: Mus musculus

<400> SEQUENCE: 4

Glu Val Met Leu Val Glu Ser Gly Gly Arg Leu Val Lys Pro Gly Gly
1               5                   10                  15

Ser Leu Lys Leu Ser Cys Ala Ala Ser Gly Phe Thr Phe Ser Ser Tyr
                20                  25                  30

Gly Met Ser Trp Val Arg Gln Thr Pro Glu Lys Arg Leu Glu Trp Val
            35                  40                  45

Ala Thr Ile Ser Gly Gly Ser Tyr Thr Tyr Tyr Pro Asp Ser Val
        50                  55                  60

Lys Gly Arg Phe Thr Ile Ser Arg Asp Asn Val Lys Asn Asn Leu Tyr
65                  70                  75                  80

Leu Gln Met Ser Ser Leu Arg Ser Glu Asp Thr Ala Leu Tyr Tyr Cys
                85                  90                  95

Ala Arg Arg Gly Ala Tyr Gly Asp Tyr Gly Trp Phe Ala Tyr Trp Gly
            100                 105                 110

Gln Gly Thr Leu Val Thr Val Ser Ala
        115                 120

<210> SEQ ID NO 5
<211> LENGTH: 11
<212> TYPE: PRT
<213> ORGANISM: Mus musculus

<400> SEQUENCE: 5

Arg Ala Ser Gln Ser Ile Asn Asn Asn Leu His
1               5                   10

<210> SEQ ID NO 6
<211> LENGTH: 7
<212> TYPE: PRT
<213> ORGANISM: Mus musculus

<400> SEQUENCE: 6

Cys Ala Ser Gln Ser Ile Ser
1               5

<210> SEQ ID NO 7
<211> LENGTH: 9
<212> TYPE: PRT
<213> ORGANISM: Mus musculus

<400> SEQUENCE: 7

Gln Gln Ser Asn Ser Trp Pro Leu Thr
1               5

<210> SEQ ID NO 8
<211> LENGTH: 107
<212> TYPE: PRT
<213> ORGANISM: Mus musculus

<400> SEQUENCE: 8

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Asn Asn Asn
                20                  25                  30

Leu His Trp Tyr Gln Gln Lys Ser His Glu Ser Pro Arg Leu Leu Ile
            35                  40                  45
```

```
Lys Cys Ala Ser Gln Ser Ile Ser Gly Ile Pro Ser Arg Phe Ser Gly
         50                  55                  60
Ser Gly Ser Gly Thr Asp Phe Thr Leu Ser Ile Asn Ser Val Glu Thr
 65                  70                  75                  80
Glu Asp Phe Gly Met Tyr Phe Cys Gln Gln Ser Asn Ser Trp Pro Leu
                 85                  90                  95
Thr Phe Gly Ala Gly Thr Lys Leu Glu Leu Lys
            100                 105

<210> SEQ ID NO 9
<211> LENGTH: 19
<212> TYPE: DNA
<213> ORGANISM: Homo sapiens

<400> SEQUENCE: 9
cggctttgct ggggacgat                                                19

<210> SEQ ID NO 10
<211> LENGTH: 21
<212> TYPE: DNA
<213> ORGANISM: Homo sapiens

<400> SEQUENCE: 10 cagggcaac acgaagctca t                                              21

<210> SEQ ID NO 11
<211> LENGTH: 24
<212> TYPE: DNA
<213> ORGANISM: Homo sapiens

<400> SEQUENCE: 11
attgcagtgg ttatcatcgg agtg                                          24

<210> SEQ ID NO 12
<211> LENGTH: 24
<212> TYPE: DNA
<213> ORGANISM: Homo sapiens

<400> SEQUENCE: 12
ctcgttgttg gagttcagaa gtgg                                          24

<210> SEQ ID NO 13
<211> LENGTH: 20
<212> TYPE: DNA
<213> ORGANISM: Homo sapiens

<400> SEQUENCE: 13
ctggaacggt gaaggtgaca                                               20

<210> SEQ ID NO 14
<211> LENGTH: 23
<212> TYPE: DNA
<213> ORGANISM: Homo sapiens

<400> SEQUENCE: 14
aagggacttc ctgtaacaat gca                                           23

<210> SEQ ID NO 15
<211> LENGTH: 10
<212> TYPE: PRT
<213> ORGANISM: Mus musculus
```

```
<400> SEQUENCE: 15

Gly Tyr Ser Phe Thr Gly Tyr Tyr Met His
1               5                   10

<210> SEQ ID NO 16
<211> LENGTH: 17
<212> TYPE: PRT
<213> ORGANISM: Mus musculus

<400> SEQUENCE: 16

Arg Ile Ile Pro Tyr Asn Gly Ala Thr Ser Tyr Asn Gln Asn Phe Lys
1               5                   10                  15
Asp

<210> SEQ ID NO 17
<211> LENGTH: 13
<212> TYPE: PRT
<213> ORGANISM: Mus musculus

<400> SEQUENCE: 17

Ser Arg Tyr Tyr Gly Arg Ala Pro Tyr Tyr Phe Asp Tyr
1               5                   10

<210> SEQ ID NO 18
<211> LENGTH: 122
<212> TYPE: PRT
<213> ORGANISM: Mus musculus

<400> SEQUENCE: 18

Glu Val Arg Leu Gln Gln Ser Gly Pro Glu Leu Val Lys Pro Gly Thr
1               5                   10                  15

Ser Val Lys Ile Ser Cys Lys Ala Ser Gly Tyr Ser Phe Thr Gly Tyr
            20                  25                  30

Tyr Met His Trp Val Lys Gln Ser Pro Val Lys Ser Leu Glu Trp Ile
        35                  40                  45

Gly Arg Ile Ile Pro Tyr Asn Gly Ala Thr Ser Tyr Asn Gln Asn Phe
    50                  55                  60

Lys Asp Lys Ala Ser Leu Thr Val Asp Lys Ser Ser Arg Thr Ala Tyr
65                  70                  75                  80

Met Asp Leu His Ser Leu Thr Ser Glu Asp Ser Ala Val Tyr Tyr Cys
                85                  90                  95

Ala Arg Ser Arg Tyr Tyr Gly Arg Ala Pro Tyr Tyr Phe Asp Tyr Trp
            100                 105                 110

Gly Gln Gly Thr Thr Leu Thr Val Ser Ser
        115                 120

<210> SEQ ID NO 19
<211> LENGTH: 16
<212> TYPE: PRT
<213> ORGANISM: Mus musculus

<400> SEQUENCE: 19

Arg Ser Ser Gln Ser Ile Val His Ser Asn Gly Asn Thr Tyr Leu Glu
1               5                   10                  15

<210> SEQ ID NO 20
<211> LENGTH: 7
<212> TYPE: PRT
<213> ORGANISM: Mus musculus

<400> SEQUENCE: 20
```

```
Lys Val Ser Asn Arg Phe Ser
1               5

<210> SEQ ID NO 21
<211> LENGTH: 9
<212> TYPE: PRT
<213> ORGANISM: Mus musculus

<400> SEQUENCE: 21

Phe Gln Gly Ser His Val Pro Phe Thr
1               5

<210> SEQ ID NO 22
<211> LENGTH: 112
<212> TYPE: PRT
<213> ORGANISM: Mus musculus

<400> SEQUENCE: 22

Asp Val Val Val Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Ile Ser Gly Ser Gly Ser Gly Thr Asp Phe Thr Leu Lys Ile
65                  70                  75                  80

Ser Arg Val Glu Ala Gly Asp Leu Gly Val Tyr Ser Cys Phe Gln Gly
                85                  90                  95

Ser His Val Pro Phe Thr Phe Gly Ser Gly Thr Lys Leu Glu Ile Lys
                100                 105                 110
```